(12) United States Patent
Kauvar et al.

(10) Patent No.: US 10,570,193 B2
(45) Date of Patent: Feb. 25, 2020

(54) BINDING MOIETIES FOR BIOFILM REMEDIATION

(71) Applicant: Trellis Bioscience, LLC, Menlo Park, CA (US)

(72) Inventors: Lawrence M. Kauvar, San Francisco, CA (US); Stefan Ryser, Menlo Park, CA (US); Angeles Estelles, Belmont, CA (US); Reyna J. Simon, Los Gatos, CA (US); Lauren Opremcak Bakaletz, Columbus, OH (US); Steven David Goodman, Columbus, OH (US)

(73) Assignee: Trellis Bioscience, LLC, Redwood City, CA (US)

( * ) Notice: Subject to any disclaimer, the term of this patent is extended or adjusted under 35 U.S.C. 154(b) by 0 days.

(21) Appl. No.: 16/181,260

(22) Filed: Nov. 5, 2018

(65) Prior Publication Data

US 2019/0055304 A1 Feb. 21, 2019

Related U.S. Application Data

(60) Division of application No. 15/144,681, filed on May 2, 2016, now Pat. No. 10,233,234, which is a continuation-in-part of application No. 15/042,061, filed on Feb. 11, 2016, now abandoned, which is a continuation-in-part of application No. 14/789,842, filed on Jul. 1, 2015, now abandoned, which is a continuation-in-part of application No. 14/668,767, filed on Mar. 25, 2015, now abandoned, which is a continuation-in-part of application No. 14/497,147, filed on Sep. 25, 2014, now abandoned.

(60) Provisional application No. 61/926,828, filed on Jan. 13, 2014.

(51) Int. Cl.
| | | |
|---|---|---|
| A01N 63/00 | (2006.01) |
| A61K 48/00 | (2006.01) |
| A61K 39/395 | (2006.01) |
| C07K 16/12 | (2006.01) |
| A61K 39/40 | (2006.01) |
| A01N 63/02 | (2006.01) |
| A61K 45/06 | (2006.01) |
| A61K 49/00 | (2006.01) |
| C07K 14/31 | (2006.01) |
| G01N 33/569 | (2006.01) |
| C12Q 1/18 | (2006.01) |
| G01N 33/566 | (2006.01) |
| A61K 39/00 | (2006.01) |
| C12N 15/86 | (2006.01) |
| A61K 35/12 | (2015.01) |

(52) U.S. Cl.
CPC ......... *C07K 16/1271* (2013.01); *A01N 63/02* (2013.01); *A61K 39/40* (2013.01); *A61K 45/06* (2013.01); *A61K 49/00* (2013.01); *C07K 14/31* (2013.01); *C07K 16/1214* (2013.01); *C07K 16/1228* (2013.01); *C07K 16/1242* (2013.01); *C07K 16/1275* (2013.01); *C12Q 1/18* (2013.01); *G01N 33/566* (2013.01); *G01N 33/56911* (2013.01); *A61K 35/12* (2013.01); *A61K 39/00* (2013.01); *A61K 2039/505* (2013.01); *C07K 2317/21* (2013.01); *C07K 2317/33* (2013.01); *C07K 2317/34* (2013.01); *C07K 2317/76* (2013.01); *C07K 2317/92* (2013.01); *C07K 2319/00* (2013.01); *C12N 15/86* (2013.01); *G01N 2333/195* (2013.01); *G01N 2333/21* (2013.01); *G01N 2333/245* (2013.01); *G01N 2333/26* (2013.01); *G01N 2333/285* (2013.01); *G01N 2469/10* (2013.01)

(58) Field of Classification Search
CPC .............. A61K 2039/522; A61K 38/00; A61K 2039/505; C12N 15/86
See application file for complete search history.

(56) References Cited

U.S. PATENT DOCUMENTS

| | | |
|---|---|---|
| 6,846,651 B2 | 1/2005 | Fleischmann |
| 7,413,868 B2 | 8/2008 | Kauvar |
| 7,939,344 B2 | 5/2011 | Kauvar |
| 8,999,291 B2 | 4/2015 | Goodman |
| 2002/0132753 A1 | 9/2002 | Rosen |
| 2003/0060410 A1 | 3/2003 | Tracey |
| 2003/0099602 A1 | 5/2003 | Levin |

(Continued)

FOREIGN PATENT DOCUMENTS

| | | |
|---|---|---|
| JP | 2005519998 | 7/2005 |
| JP | 2006506441 | 2/2006 |

(Continued)

OTHER PUBLICATIONS

Adams et al., (2007) "Epitope-mapping the immune response of children with otitis media and adults with chronic obstructive pulmonary disease to the PilA protein of nontypeable Haemophilus influenzae type IV pilus," 9th International Symposium on Recent Advances in Otitis Media; St. Pete Beach, FL.

(Continued)

*Primary Examiner* — Gary B Nickol
*Assistant Examiner* — Lakia J Jackson-Tongue
(74) *Attorney, Agent, or Firm* — FisherBroyles, LLP; Victoria L. Boyd; Frank W. Leak

(57) ABSTRACT

Binding agents able to disrupt bacterial biofilms of diverse origin are described, including monoclonal antibodies suitable for administration to a selected species, and antibody mimics including aptamer nucleic acids. Methods to prevent formation of or to dissolve biofilms with these binding agents are also described. Immunogens for eliciting antibodies to disrupt biofilms are also described.

6 Claims, 9 Drawing Sheets

Specification includes a Sequence Listing.

(56) References Cited

U.S. PATENT DOCUMENTS

| | | |
|---|---|---|
| 2003/0229065 A1 | 12/2003 | Levy |
| 2004/0202670 A1 | 10/2004 | Apicella |
| 2005/0049402 A1 | 3/2005 | Babcook |
| 2005/0131222 A1 | 6/2005 | Fleischmann |
| 2005/0221439 A1 | 10/2005 | Bakaletz |
| 2006/0030539 A1 | 2/2006 | Nick |
| 2006/0099207 A1 | 5/2006 | Wu |
| 2006/0121047 A1 | 6/2006 | Tracey |
| 2006/0228384 A1 | 10/2006 | Eldridge |
| 2006/0240045 A1 | 10/2006 | Berthet |
| 2007/0154529 A1 | 7/2007 | Bullerdiek |
| 2007/0264256 A1 | 11/2007 | Bakaletz |
| 2009/0029929 A1 | 1/2009 | Nakajima |
| 2010/0291177 A1 | 11/2010 | Hermans |
| 2011/0236306 A1 | 9/2011 | Goodman |
| 2012/0128701 A1 | 5/2012 | Goodman |
| 2015/0086542 A1 | 3/2015 | Goodman |
| 2015/0086561 A1 | 3/2015 | Kauvar |
| 2015/0166641 A1 | 6/2015 | Goodman |
| 2015/0197558 A1 | 7/2015 | Kauvar |
| 2015/0299298 A1 | 10/2015 | Kauvar |
| 2016/0194384 A1 | 7/2016 | Goodman |

FOREIGN PATENT DOCUMENTS

| | | |
|---|---|---|
| JP | 2006506467 | 2/2006 |
| JP | 2008520552 | 6/2008 |
| JP | 2013529893 | 7/2013 |
| WO | 200047104 | 8/2000 |
| WO | 2003026691 | 4/2003 |
| WO | 2004014418 | 2/2004 |
| WO | 2004044001 | 5/2004 |
| WO | 2004072094 | 8/2004 |
| WO | 2005025604 | 3/2005 |
| WO | 2006017816 | 2/2006 |
| WO | 2006083301 | 8/2006 |
| WO | 2006114805 | 11/2006 |
| WO | 2007001422 | 1/2007 |
| WO | 2011123396 | 10/2011 |
| WO | 2012034090 | 3/2012 |
| WO | 2014201305 | 2/2014 |
| WO | 2015048484 | 4/2015 |

OTHER PUBLICATIONS

Adams, L. et al. (2007) "Epitope-mapping the immune response of children with otitis media and adults with chronic obstructive pulmonary disease to the PilA protein of nontypeable Haemophilus influenzae type IV pilus," 107th General Meeting, American Society for Microbiology; Toronto, ON.
Advisory Action for U.S. Appl. No. 15/078,987, dated Mar. 10, 2017, 3 pages.
Advisory Action for U.S. Appl. No. 15/078,987, dated Mar. 29, 2017, 3 pages.
Andersson, U. et al. (2011) "HMGB1 is a Therapeutic Target for Sterile Inflammation and Infection," Annu. Rev. Immunol. 29:139-162.
Bakaletz, L.O., New strategies to target bacterial biofilms, 28th Annual North American Cystic Fibrosis Conference (NACFC), Atlanta, GA, Oct. 9-11, 2014 (presentation).
Bakaletz, L.O. et al. (1999) "Protection against Development of Otitis Media Induced by Nontypeable Haemophilus influenzae by Both Active and Passive Immunization in a Chinchilla Model of Virus-Bacterium Superinfection," Infecion and Immunity 67(6): 2746-2762.
Bakaletz, LO. et al. (1997) "Relative immunogenicity and efficacy of two synthetic chimeric peptides of fimbrin as vaccinogens against nasopharyngeal colonization by nontypeable Haemophilus influenzae in the chinchilla," Vaccine 15(9):955-961.
Balaetz, LO., Biofilms can be dispersed by focusing the immune system on a common family of bacterial nucleoid associated proteins, 6th ASM Conference on Biofilms, Miami, FL, Sep. 29-Oct. 4, 2012 (presentation).

Barve, M.P. et al. (2003) "Cloning and characterization of the mating type (MAT) locus from *Ascochyta rabiei* (teleomorph: *Didymella rabiei*) and a MAT phylogeny of legume-associated *Ascochyta* spp.," Fungal Genetics and Biology 39(2):151-167.
Bass, J.I.F. et al. (2010) "Extracellular DNA: A Major Proinflammatory Component of Pseudomonas aeruainosa Biofilms," The Journal of Immunology 184:6386-6395.
Beech, Iwona B., et al., "Microbe-surface interactions in biofouling and biocorrosion processes", International MicrobioloQY (2005) 8: 157-168.
Brandstetter et al., "Antibodies directed against Integration Host Factor Mediate Biofilm Clearance from Nasopore®," Laryngoscope (2013) 123(11):2626-2632.
Brockson, M.E. et al. (2014) "Evaluation of the kinetics and mechanism of action of anti-integration host factor-mediated disruption of bacterial biofilms," Molecular Microbiology 93(6)1246-1258: Supplementary Material, 6 pages.
Catlin, B.W., "Extracellular Deoxyribonucleic Acid of Bacteria and a Deoxyribonuclease Inhibitor," Science, vol. 124, pp. 441-442 (Jun. 1956).
Chen et al., Int. J. Mol. Sci. 2013; 14: 18488-18501.
Chen, Christina, et al., "Substrate specificity of Helicobacter pylori histone-like HU protein is determined by insufficient stabilization of DNA flexure points", Biochem J. (2004) 383, pp. 343-351.
Cho, J.H. et al. (2001) "The modulation of the biological activities of mitochondrial histone Abf2p by yeast PKA and its possible role in the regulation of mitochondrial DNA content during glucose repression," Biochimica et Biophysica Acta 1522(3):175-186.
Cohavy, O. et al. (1999) "Identification of a Novel Mycobacterial Histone H1 Homologue (HupB) as an Antigenic Target of pANCA Monoclonal Antibody and Serum Immunoglobulin A from Patients with Cohn's Disease," Infection and Immunity 67(12):6510-6517.
Collarini, Ellen J. et al., "Potent High-Affinity Antibodies for Treatment and Prophylaxis of Respiratory Syncytial Virus Derived from B Cells of Infected Patients", The Journal of Immunology, 2009, 183: 6338-6345.
Dalai, Baolige et al. "Histone-like protein H-NS regulates biofilm formation and virulence of Actinobacillus pleuropheumoniae", Microbial Pathogenesis 46(2009) 128-134.
Donlan et al., "Biofilms: survival mechanisms of clinically relevant microorganisms," Clin. Microbiol. Rev. (2002) 15(2):167-193.
Eboigbodin, Kevin E. et al., "Characterization of the Extracellular Polymeric Substances Produced by *Escherichia coli* Using Infrared Spectroscopic Proteomic, and Aggregation Studies", Biomacromolecules 2008, 9, 686-695.
Estelles, A. et al. (2016) "A High-Affinity Native Human Antibody Disrupts Biofilm from *Staphylococcus aureus* Bacteria and Potentiates Antibiotic Efficacy in a Mouse Implant Infection Model," Antimicrobial Agents and Chemotherapy 60(4):2292-2301.
Estrela, A.B. et al. (2010) "Combining Biofilm-Controlling Compounds and Antibiotics as a Promising New Way to Control Biofilm Infections," Pharmaceuticals 3:1374-1393.
Falciola, L. et al. (1994) "Mutational analysis of the DNA binding domain A of chromosomal protein HMG1," Nucleic Acids Research 22(3):285-292.
Fan, Z. et al. (2002) "HMG2 Interacts with the Nucleosome Assembly Protein SET and is a Target of the Cytotoxic T-Lymphocyte Protease Granzyme A," Molecular and Cellular Biology 22(8):2810-2820.
Final Office Action in U.S. Appl. No. 13/073,782, dated Mar. 27, 2014.
Final Office Action in U.S. Appl. No. 13/229,575, dated Aug. 29, 2013.
Final Office Action in U.S. Appl. No. 13/229,575, dated Sep. 19, 2014.
Final Office Action in U.S. Appl. No. 14/493,051, dated Oct. 7, 2016.
Final Office Action in U.S. Appl. No. 14/535,254, dated Jun. 9, 2017.
Final Office Action in U.S. Appl. No. 14/535,254, dated Mar. 25, 2016.
Final Office Action in U.S. Appl. No. 14/885,800, dated May 29, 2018.

(56) References Cited

OTHER PUBLICATIONS

Final Office Action in U.S. Appl. No. 14/885,800, dated May 4, 2017.
Final Office Action in U.S. Appl. No. 14/967,228, dated Nov. 22, 2017.
Final Rejection for U.S. Appl. No. 15/078,987, dated Dec. 28, 2016, 12 pages.
Garcia-Contreras et al., "Protein Translation and Cell Death: The Role of Rare tRNAs in Biofilm Formation and in Activating Dormant Phage Killer Genes," PLoS ONE (2008) 3(6):e2394, 15 pages.
George, A.M. et al. (2009) "Cystic fibrosis infections: treatment strategies and prospects," FEMS Microbial Lett. 300:153-164.
Gerstel, U. et al. (2003) "Complex Regulation of csgD Promoter Activity by Global Regulatory Proteins," Molecular Microbiology 49(3):639-654.
Goodman et al, "Biofilms can be dispersed by focusing the immune system on a common family of bacterial nucleoid-associated proteins," Mucosal Immunol. (2011) 4(6):625-637.
Goodman, S.D. et al. (1999) "Replacement of Integration Host Factor Protein-induced DNA Bending by Flexible Regions of DNA," The Journal of Biological Chemistry 274(52):37004-37011.
Goodman, S.D., "A new immunotherapeutic approach that disperses biofilms", Banff Conference on Infectious Diseases, Banff, Alberta, Canada, May 18, 2012 (presentation).
Goodman, S.D., Making and breaking biofilms, Ohio Branch American Society for Microbiology Annual Meeting, Columbus, OH, Apr. 11-12, 2014 (presentation).
Goodman, S.D., Nucleoprotein complexes in the extracellular matrix are critical for the structural integrity of bacterial biofilms, 112th General Meeting, American Society for Microbiology, San Francisco, CA, Jun. 18, 2012 (presentation).
Goodman, S.D., The DNABII family of proteins: Diagnostic markers and therapeutic targets of bacterial biofilms, International Congress on Bacteriology and Infectious Disease, Baltimore, MD, Nov. 21, 2013.
Goodman, Steven D. et al. "In Vitro Selection of Integration Host Factor Binding Sites", Journal of Bacteriology, May 1999, pp. 3246-3255.
Govan, J.R. et al. (1996) "Microbial pathogenesis in cystic fibrosis: mucoid Pseudomonas aeruginosa and Burkholderia cepacia," Microbiol. Rev. 60(3):539-574.
Granston, A.E. et al. (1993) "Characterization of a Set of Integration Host Factor Mutants Deficient for DNA Binding," J. Mol. Biol. 234:45-59.
Greenspan, N.S. et al. (1999) "Defining epitopes: It's not as easy as it seems," Nature Biotechnology 17:936-937.
Gustave et al., Biofilms recovered from the sputum of CF patients contain the bacterial protein integration host factor (IHF), 25th Annual North American Cystic Fibrosis Conference, Anaheim, CA, Nov. 3-5, 2011 (poster).
Gustave et al., Biofilms recovered from the sputum of CF patients contain the bacterial protein integration host factor (IHF), Abstract 25th Annual North American Cystic Fibrosis Conference, Anaheim, CA, Nov. 3-5, 2011.
Gustave, J.E. et al. (2013) "Targeting bacterial integration host factor to disrupt biofilms associated with cystic fibrosis," Journal of Cystic Fibrosis 12(4):384-389.
Hall-Stoodley, L. et al. (2008) "Characterization of biofilm matrix, degradation by DNase treatment and evidence of capsule down regulation in Streptococcus pneumoniae clinical isolates," BMC Microbiology 8:173, 16 pages.
Hall-Stoodley, L. et al. (2009) "Evolving concepts in biofilm infections", Cellular Microbiology, 11(7)1034-1043.
Hall-Stoodley, Luanne et al., "Direct Detection of Bacterial Biofilms on the Middle-Ear Mucosa of Children With Chronic Otitis Media", JAMA Jul. 12, 2006; 296(2): 202-2011.
Haluzi, H., et al., "Genes Coding for Integration Host Factor Are Conserve in Gram-Negative Bacteria," Journal of Bacteriology, 173(19), pp. 6297-6299 (Oct. 1991).

Harley, V.R. et al. (2003) "The Molecular Action and Regulation of the Testis-Determining Factors, SRY (Sex-Determining Region on the Y Chromosome) and SOX9 [SRY-Related Hiqh-Mobility Group (HMG) Box 91," Endocrine Reviews 24(4):466-487.
Haruta, I. et al. (2008) "A Possible Role of Histone-Like DNA-Binding Protein of Streptococcus intermedius in the Pathogenesis of Bile Duct Damage in Primary Biliary Cirrhosis," Clinical Immunology 127(2):245-251.
Haruta, I. et al. (2010) "Long-term bacterial exposure can trigger nonsuppurative destructive cholangitis associated with multifocal epithelial inflammation," Laboratory investigation 90:577-588.
Hoyle, B., et al., "Bacterial Resistance to Antibiotics: The Role of Biofilms," Prog. Drug Res., 37, pp. 91-105 (1991).
International Search Report and Written Opinion for PCT/US14/57771, dated Mar. 20, 2015, 12 pages.
International Search Report and Written Opinion for PCT/US2016/024107, dated Jul. 27, 2016, 8 pages.
International Search Report and Written Opinion in PCT International Application No. PCT/US2014/042201, dated Nov. 28, 2014.
Janeway, C.A., et al., "Manipulating the immune response to fight infection," Immunobiology: The Immune System in Health and Disease, 5th ed. (2001 ); retrieved online from https://www.ncbi.nlm.nih.qov/books/NBK27131/.
Jiao, Yongqin et al., "Identification of Biofilm Matrix-Associated Proteins form an Acid Mine Drainage Microbial Community", Applied and Environmental Microbiology, Aug. 2011, vol. 77, No. 15, pp. 5230-5237.
Jodar, L. et al. (2002) "Development of vaccines against meningococcal disease," Lancet 359:1499-1508.
Johnson, R., et al., "Chapter 8: Bending and Compaction of DNA by Proteins," Protein-Nucleic Acid Interactions: Structural Biology, pp. 176-220 (2008).
Jurcisek, Joseph A. et al., "Biofilms Formed by Nontypeable Haemophilus influenza In Vivo Contain both Double-Stranded DNA and Type IV Pilin Protein", Journal of Bacteriology, vol. 189, No. 10, May 2007, pp. 3868-3875.
Jurcisek, Joseph A. et al., "Role of Sialic Acid and Complex Carbohydrate Biosynthesis in Biofilm Formation by Nontypeable Haemophilus influenza in the Chinchilla Middle Ear", Infection and Immunity, vol. 73, No. 6, Jun. 2005, pp. 3210-3218.
Justice, S.S. et al. (2012) "Aberrant Community Architecture and Attenuated Persistence of Uropathogenic Escherichia coli in the Absence of Individual IHF Subunits," PLoS ONE 7(10):e48349, 1-15.
Kamashev, D. et al. (2000) "The histone-like protein HU binds specifically to DNA recombination and repair intermediates," The EMBO Journal 19(23):6527-6535.
Kennedy, B-J. et al. (2000) "Passive Transfer of Antiserum Specific for Immunogens Derived from a Nontypeable Haemophilus influenzae Adhesin and Lipoprotein D Prevents Otitis Media after Heteroloqous Challenqe," Infection and Immunity 68(5):2756-2765.
Kim, D-H. et al. (2014) "Beta-Arm flexibility of HU from Staphylococcus aureus dictates the DNA-binding and recognition mechanism," Acta Cryst. D70:3273-3289.
Kim, NA Young et al. "Proteins Released by Helicobacter pylori In Vitro," Journal of Bacteriology, Nov. 2002, vol. 184, No. 22, pp. 6155-6162.
Kirketerp-Moller, K. et al. (2008) "Distribution, Organization, and Ecology of Bacteria in Chronic Wounds," Journal of Clinical Microbiology 46(8):2717-2722.
Kornblit, B. et al. (2007) "The genetic variation of the human HMG1 gene," Tissue Antigens 70:151-156.
Kyd, J.M. et al. (2003) "Efficacy of the 26-Kilodalton Outer Membrane Protein and Two P5 Fimbrin-Derived Immunogens to Induce Clearance of Nontypeable Haemophilus influenzae from the Rat Middle Ear and Lungs as Well as from the Chinchilla Middle Ear and Nasopharynx," Infection and Immunity 71 (8):4691-4699.
Labbe, E. et al. (2000) "Association of Smads with lymphoid enhancer binding factor 1/T cell-specific factor mediates cooperative signaling by the transforming growth factor-13 and Wnt pathways," Proc. Natl. Acad. Sci. USA 97(15):8358-8363.
Lebeaux, David et al. "From in vitro to in vivo Models of Bacterial Biofilm-Related Infections," Pathogens 2013, 2, 288-356.

(56) References Cited

OTHER PUBLICATIONS

Li, L. et al. (2000) "Retroviral cDNA Integration: Stimulation by HMG I Family Proteins," Journal of Virology 74(23):10965-10974.
Liu, D. et al. (2008) "Histone-like DNA binding protein of *Streptococcus intermedius* induces the expression of pro-inflammatory cytokines in human monocytes via activation of ERK1 /2 and JNK pathways," Cellular Microbiology 10(1 ):262-276.
Liu, D. et al. (2008) "The essentiality and involvement of *Streptococcus intermedius* histone-like DNA-binding protein in bacterial viability and normal growth," Molecular Microbiology 68(5) :1268-1282.
Lunsford, R.D. et al. "DNA-Binding Activities in *Streptococcus gordonii*: Indentification of a Receptor-Nickase and a Histonelike Protein," Current Microbiology vol. 32 (1996), pp. 95-100.
Malhotra et al., "Fine mapping the functional epitopes within integration host factor, a novel immunotherapeutic target for NTH I-induced diseases of the airway," 18th International Symposium on Recent Advances in Otitis Media, National Harbor, MD, Jun. 7-11, 2015 (poster).
Malhotra et al., Defining the functional epitopes of Integration Host Factor (IHF) to develop a novel biofilm-focused immunotherapeutic against nontypeable Haemophilus influenzae-induced chronic and recurrent otitis media, Abst. 18th International Symposium on Recent Advances in Otitis Media, National Harbor, MD, Jun. 7-11, 2015.
Malhotra, et al, Identification of immunoprotective domains within the bacterial DNA-binding protein, integration host factor, 20th Annual Midwest Microbial Pathogenesis Meeting. The Ohio State University, Columbus, OH, Aug. 23-25, 2013 (poster).
Malhotra, et al, Identification of immunoprotective domains within the bacterial DNA-binding protein, integration host factor, Abst. 20th Annual Midwest Microbial Pathogenesis Meeting. The Ohio State University, Columbus, OH, Aug. 23-25, 2013.
Malhotra, et al., Fine mapping the functional epitopes within integration host factor, a novel therapeutic target for nontypeable Haemophilus influenza-induced diseases of the respiratory tract, Abst. 12th Annual AMA Research Symposium, Dallas, TX, Nov. 7, 2014.
Malhotra, et al., Identification of immunoprotective domains within the bacterial DNA-binding protein, integration host factor, Abst. Seventh Extraordinary International Symposium on Recent Advances in Otitis Media, Stockholm, Sweden, Jun. 12, 2013.
Malhotra, et al., Identification of immunoprotective domains within the bacterial DNA-binding protein, integration host factor, Seventh Extraordinary International Symposium on Recent Advances in Otitis Media, Stockholm, Sweden, Jun. 15, 2013 (presentation).
Martinez-Antonio, A. et al. (2008), "Functional organization of *Escherichia coli* transcriptional requlatory network", J. Mol. Biol. 381 :238-247.
Meluleni, G.J. et al. (1995) "Mucoid Pseudomonas aeruginosa Growing in a Biofilm In Vitro are Killed by Opsonic Antibodies to the Mucoid Exopolysaccharide Capsule but Not by Antibodies Produced During Chronic Lung Infection in Cystic Fibrosis Patients," J. Immunology 155:2029-2038.
Mouw, K.W. et al. (2007) "Shaping the Borrelia burgdorferi genome: crystal structure and bindinq properties of the DNA-bendinq protein Hbb," Molecular Microbioloqy 63(5):1319-1330.
Mukherjee, Joy et al. "Quantitative protein expression and cell surface characteristics of *Escherichia coli* MG1655 biofilms," Proteomics 2011, vol. 11,39-351.
Murphy, T.F. et al. (2009) "Microbial Interactions in the Respiratory Tract," The Pediatric Infectious Disease Journal 28:S121-S126.
Murphy, Timothy F. et al. "Biofilm formation by nontypeable Haemophilus influenzae: strain variablitiy, outer membrane antigen expression and role of pili," BMC Microbiology 2002,2:7, 8 pgs.
Nakamura, Y. et al. (2001) "HMG Box A in HMG3 Protein Functions as a Mediator of DNA Structural Alteration Toqether with Box B," J. Biochem. 1129:643-651.

Nash, H.A. et al. (1987) "Overproduction of *Escherichia coli* integration Host Factor, a Protein with Nonidentical Subunits," Journal of Bacteriology 169(9):4124-4127.
NCBI Genebank: P0A6Y1 (Sep. 13, 2005).
Non-Final Office Action for U.S. Appl. No. 14/493,051 dated Mar. 12, 2015.
Non-Final Office Action for U.S. Appl. No. 14/493,051, dated Oct. 8, 2015.
Non-Final Office Action for U.S. Appl. No. 14/535,254, dated Sep. 9, 2015.
Non-Final Office Action in U.S. Appl. No. 13/073,782, dated Jun. 10, 2013.
Non-Final Office Action in U.S. Appl. No. 13/073,782, dated Jun. 25, 2014.
Non-Final Office Action in U.S. Appl. No. 13/229,575, dated Jan. 10, 2013.
Non-Final Office Action in U.S. Appl. No. 13/229,575, dated Mar. 31, 2014.
Non-Final Office Action in U.S. Appl. No. 14/493,051, dated Apr. 28, 2016.
Non-Final Office Action in U.S. Appl. No. 14/493,051, dated Jan. 10, 2017.
Non-Final Office Action in U.S. Appl. No. 14/535,254, dated Jan. 26, 2018.
Non-Final Office Action in U.S. Appl. No. 14/535,254, dated Jul. 10, 2017.
Non-Final Office Action in U.S. Appl. No. 14/885,800, dated Dec. 15, 2017.
Non-Final Office Action in U.S. Appl. No. 14/885,800, dated Oct. 31, 2016.
Non-Final Office Action in U.S. Appl. No. 14/967,228, dated May 19, 2017.
Non-Final Office Action in U.S. Appl. No. 15/078,987, dated Mar. 16, 2018.
Non-final Rejection for U.S. Appl. No. 15/078,987, dated Jul. 14, 2016, 15 pages.
Non-final Rejection for U.S. Appl. No. 15/078,987, dated Jun. 14, 2017, 25 pages.
Notice of Allowability in U.S. Appl. No. 13/073,782, dated Mar. 4, 2015.
Notice of Allowance in U.S. Appl. No. 13/073,782, dated Aug. 19, 2014.
Notice of Allowance in U.S. Appl. No. 14/493,051, dated Apr. 25, 2017.
Notice of Allowance in U.S. Appl. No. 14/493,051, dated Jan. 27, 2017.
Novotny et al., "Structural Stability of Burkholderia cenocepacia Biofilms is Reliant on eDNA Structure and Presence of a Bacterial Nucleic Acid Binding Protein," PLOS One (2013) 8(6) :e67629, 15 pages.
Novotny, L.A. et al. (2000) "Epitope mapping of the Outer Membrane Protein P5-Homologous Fimbrin Adhesin of Nontypeable Haemophilus influenzas," Infection and Immunity 68(4):2119-2128.
Novotny, L.A. et al. (2002) "Detection and characterization of pediatric serum antibody to the OMP PS-homologous adhesin of nontypeable Haemophilus influenzae during acute otitis media," Vaccine 20(29-30):3590-3597.
Novotny, L.A. et al. (2003) "The Fourth Surface-Exposed Region of the Outer Membrane Protein PS-Homologous Adhesin of the Nontypable Haemophilus influenzae is an Immunodominant But Nonprotective Decoying Epitope," The Journal of Immunology 171 (4):1978-1983.
Novotny, L.A. et al. (2006) "Passive immunization with human anti-protein D antibodies induced by polysaccharide protein D conjugates protects chinchillas against otitis media after intranasal challenge with Haemophilus influenzas," Vaccine 24(22):4804-4811.
Novotny, L.A. et al. (2010) "Epitope mapping immunodominant regions of the PilA protein of nontypeable Haemophilus influenzae (NTHI) to facilitate the design of two novel chimeric vaccine candidates," Vaccine 28(1):279-289.

(56) References Cited

OTHER PUBLICATIONS

Oberto, J. et al. (1994) "Histones, HMG, HU, IHF: Meme combat," Biochimie 76:901-908.
Ordway, D.J. et al. (2010) "Evaluation of Standard Chemotherapy in the Guinea Pig Model of Tuberculosis," Antimicrobial Agents and Chemotherapy 54:1820-1833.
Otto, M. (2009) "*Staphylococcus epidermidis*—the 'accidental' pathogen," Nature Reviews Microbiology 7:555-567.
PDB ID: 1 IHF: Rice, P.A., et al. (Aug. 1996), 1 page; retrieved online from http://www.rcsb.org/pdb/explore.do?structureId=IHF.
Pedulla, M.L. et al. (1996) "A novel host factor for integration of mycobacteriophage L5," Proc. Natl. Acad. Sci. USA 93:15411-15416.
Percival, S.L. et al. (2015) "Biofilms and Wounds: An Oveiview of the Evidence," Advances in Wound Care 4(7}:373-381.
Petersen, Fernanda C. et al. "Biofilm Mode of Growth of *Streptococcus intermedius* Favoreed by a Competence-Stimulating Signaling Peptide," Journal of Bateriology, Sep. 2004, vol. 186, No. 18, pp. 6327-6331.
Pethe, Kevin et al. "Mycobacterium smegmatis laminin-binding glycoprotein shares epitopes with Mycobacterium tuberculosis heparin-binding haemagglutinin," Molecular Microbiology (2001) 39(1 ), 89, 99.
Prymula, R. et al. (2006) "Pneumococcal capsular polysaccharides conjugated to protein D for prevention of acute otitis media caused by both *Streptococcus pneumonias* and non-typable Haemophilus influenzae: a randomized double-blind efficacy study," Lancet 367(9512):740-748.
Restriction Requirement in U.S. Appl. No. 13/073,782, dated Feb. 20, 2013.
Restriction Requirement in U.S. Appl. No. 13/229,575, dated Jul. 19, 2012.
Restriction Requirement in U.S. Appl. No. 14/493,051, dated Nov. 7, 2014.
Restriction Requirement in U.S. Appl. No. 14/535,254, dated Mar. 27, 2015.
Rice, P.A. et al. (1996) "Crystal Structure of an IHF-DNA Complex: A Protein-Induced DNA U-Turn," Cell 87(7):1295-1306.
Rudikoff, S. et al. (1982) "Single amino acid substitution altering antigen-binding soecificitv," Proc. Natl. Acad. Sci. USA 79(6}:i979-i983.
Sapi, E. et al. (2012) "Characterization of Biofilm Formation by Borrelia burgdorferi In Vitro," PLOS One 7(10):e44277, 1-11.
Schwartz, K. et al. (2012) "Functional Amyloids Composed of Phenol Soluble Modulins Stabilize *Staphylococcus aureus* Biofilms," PLOS Pathogens 8:e1002744, 1-11.
Segall, Anca M. et al. "Architectural elements in nucleoprotein complexes: interchangeability of specific and non-specific DNA binding proteins," The EMBO Journal vol. 13 No. 19 pp. 4536-4548, 1994.
Shahrooei, Mohammad et al. "Inhibition of *Staphylococcus epidermidis* Biofilm Formation by Rabbit Polyclonal Antibodies against the SesC Protein," Infection and Immunity, Sep. 2009, vol. 77, No. 9, pp. 3670-3678.
Singh, P.K. et al. (2000) "Quorum-sensing signals indicate that cystic fibrosis lungs are infected with bacterial biofilms," Nature 407(12):762-764.

Skolnick, J. et al. (2000) "From genes to protein structure and function: novel applications of computational aooroaches in the genomic era," Trends in Biotechnology 18:34-39.
Smith, J.J. et al. (1996) "Cystic Fibrosis Airway Epithelia Fail to Kill Bacteria Because of Abnormal Airway Surface Fluid," Cell 85:229-236.
Stinson, M.W. et al. (1998) "Streptococcal histone-Like Protein: Primary Structure of hIpA and Protein Binding to Lipoteichoic Acid and Epithelial Cells," Infection and Immunity 66(1):259-265.
Stoltz, D.A. et al. (201 0) "Cystic Fibrosis Pigs Develop Lung Disease and Exhibit Defective Bacterial Eradication at Birth," www.ScienceTranslationMedicine.org 2(29):29ra31, 1-8.
Stros, M. et al. (2007) "The HMG-box: a versatile protein domain occurring in a wide variety of DNA-bindinq proteins," Cell. Mol. Life Sci. 64(19-20):2590-2606.
Sun, Daqian et al. "Inhibition of Biofilm Formation by Monoclonal Antibodies against *Staphylococcus epidermindis* RP62A Accumulation-Associated Protein," Clinical & Diagnostic Laboratory Immunology, Jan. 2005, vol. 12, No. 1, pp. 93-100.
Swinger, Kerren K. et al., "IHF and HU: flexible architects of bent DNA," Current Opinion in Structural Biology 2004, 14: 28-35.
Takeda, Takumi (2012). "Polyhistidine Affinity Chromatography for Purification and Biochemical Analysis of Fungal Cell Wall Degrading Enzymes," Affinity Chromotography, Dr. Sameh Maadelin (Ed.), ISBN:978-953-51-0325-7, In Tech, p. 177-186.
Taudte, S. et al. (2000) "Alanine mutagenesis of high-mobility-group-protein-1 box B (HMG1-B)," Biochem. J. 347:807-814.
Teter, Bruce et al., "DNA Bending and Twisting Properties of Integration Host Factor Determined by DNA Cyclization," Plasmid 43, 73-84 (2000).
Tetz, G.V. et al. (2009) "Effect of DNase and Antibiotics on Biofilm Characteristics," Antimicrobial Aqents and Chemotherapy 53(3):1204-1209.
Thomas, J.O. (2001) "HMG1 and 2: architectural DNA-binding proteins," Biochemical Society Transactions 29(Pt 4):395-401.
U.S. Appl. No. 14/885,800, filed Oct. 2015, Goodman et al.
U.S. Appl. No. 14/967,228, filed Dec. 2015, Goodman et al.
U.S. Office Action on U.S. Appl. No. 14/535,254, dated Aug. 12, 2016.
Van Schaik, Erin J. et al., "DNA Binding: a Novel Function of Pseudomonas aeruginosa Type IV Pili," Journal of Bacteriology, Feb. 2005, vol. 187, No. 4, pp. 1455-1464.
Various prosecution history documents and Information Disclosure Statements for US. Appl. No. 15/078,987, dated Oct. 4, 2017, 28 pages.
Whitchurch, Cynthia B. et al., "Extracellular DNA Required for Bacterial Biofilm Formation," Science vol. 295, Feb. 22, 2002, 2 pgs.
Winters, Bradford D. et al., "Isolation and Characterization of a *Streptococcus pyogenes* Protein that Binds to Basal Laminae of Human Cardiac Muscle," Infection and Immunity, Aug. 1993, vol. 61, No. 8, pp. 3259-3264.
Winther, B. et al. (2009) "Location of Bacterial Biofilm in the Mucus Overlying the Adenoid by Light Microscopy," Head & Neck Surgery 135(12): 1239-1245.
Woischnig, A.K. et al. "High Affinity Native Human Monoclonal Antibody with Broad Cross-Species Biofilm Disrupting Activity" poster presented at IAAC Meeting on Sep. 20, 2015, available at www.trellisbio.com/assets/docs/ICAAC%20Biofilm%20Poster%2020150920.pdf.
Xiong et al., Antimicrobial Agent and Chemotherapy, 2017; 61(10): 1-10.

TRL1068 Epitope  *AARKGRNPQTGKEIDIPA*

TRL1330 Epitope  *AARKGRNPQTGKEIDIPA*

BINDING MOIETIES FOR BIOFILM REMEDIATION

CROSS-REFERENCE TO RELATED APPLICATIONS

This application is a divisional of U.S. Ser. No. 15/144,681, filed 2 May 2016, which is a continuation-in-part of U.S. Ser. No. 14/789,842 filed 1 Jul. 2015, which is a continuation-in-part of U.S. Ser. No. 14/668,767 filed 25 Mar. 2015, which is a continuation-in-part of U.S. Ser. No. 14/497,147 filed 25 Sep. 2014, which claimed priority from provisional application Ser. No. 61/926,828 filed 13 Jan. 2014. This application is also a continuation-in-part of U.S. Ser. No. 15/042,061 filed 11 Feb. 2016. The contents of these documents are incorporated herein by reference.

SUBMISSION OF SEQUENCE LISTING ON ASCII TEXT FILE

The content of the following submission as ASCII text file is incorporated herein by reference in its entirety: a computer readable form (CRF) of the Sequence Listing (file name: 388512013110SeqList.txt, date recorded: 2 Nov. 2018, size: 65,492 bytes).

TECHNICAL FIELD

The invention relates to methods and compositions for preventing formation of or achieving dissolution of biofilms that inhibit immune responses and make bacteria resistant to antibiotics. More specifically, it concerns monoclonal antibodies that are derived from human cells or from transgenic animals expressing human antibody genes or that are humanized forms of antibodies native to other species wherein the affinity for a family of proteins that are implicated in the structural integrity of such biofilms exceeds the affinity of these proteins for biofilm components. Monoclonal antibodies in general and other homogeneous binding moieties with this property are also included.

BACKGROUND ART

It is well understood in the art that bacterial infections may lead to formation of biofilms that protect the bacteria from the immune system and lead them to enter a quiescent, slow growth state that makes them resistant to most antibiotics (Donlan, R. M., et al., *Clin. Microbiol. Rev.* (2002) 15:167-193). The result is persistent, recurrent infections that are very difficult to eliminate. These biofilms include as a major component branched extracellular DNA molecules, whose key role was established by showing that DNAse treatment reduced biofilms (Whitchurch, C. B., et al., *Science* (2002) 295:1487; Petersen, F. C., et al., *J. Bacteriol.* (2004) 186:6327). The higher order meshwork structure of the DNA molecules is achieved by specific proteins generally designated DNABII proteins, with homologs found in most bacterial species, including proteins designated as IHF (integration host factor) and HU (histone like protein) (Swinger, K. K., et al., *Curr. Opin. Struct. Biol.* (2004) 14:28-35; Goodman, S. D., et al., *Mucosal Immunity* (2011) 4:625-637). The substantial homology of these proteins facilitates the cooperative formation of biofilms, a feature that further renders the bacteria problematic from a treatment perspective. Members of this class are known to be present in the extracellular environment (Winters, B. D., et al., *Infect. Immun.* (1993) 61:3259-3264; Lunsford, R. D., et al., *Curr. Microbiol.* (1996) 32:95-100; Kim, N., et al., *J. Bacteriol.* (2002) 184:6155-6162) and are known to force or stabilize bends in DNA, a key feature underlying higher order structure in other contexts (Teter, B., et al., *Plasmid* (2000) 43:73-84). Mutation of the ihfA gene in *E. coli* reduced or eliminated biofilm in vitro (Garcia-Contreras, R. (2008) *PLoS ONE* 3:e2394). The present invention is based on the concept that supplying a binding moiety with sufficiently high affinity for this class of proteins will extract the proteins from the biofilm and thereby provide an effective method of destroying the biofilm by destroying the ability of the protein to bind and hold together the branched DNA. A supplied binding moiety against the DNABII protein may also destroy its ability to bind to other components present in the biofilm.

The binding moieties, of which monoclonal antibodies or fragments thereof are an important embodiment, can be supplied directly to established biofilms or used to coat surfaces to provide an immuno-adsorbent for confining the DNABII protein(s) and thereby suppressing biofilm formation. Applications include treatments of bacterial infections by systemic administration, subcutaneous, topical or inhaled administration, as well as reduction of biofouling that affects pipelines and other industrial equipment. Application to corresponding biofilm associated diseases of animals is also part of the present invention.

PCT publication WO2011/123396 provides an extensive discussion of biofilms and provides for their removal by administering to a subject polypeptides that represent the DNABII protein itself as a whole or in part, thus causing the organism to generate antibodies that can destroy the integrity of the biofilm. This document also provides, in the alternative, supplying the antibodies themselves, either ex vivo to biofilms that exist outside an organism or to a subject to confer passive protection. Antibodies to other biofilm associated proteins have similarly been used to interfere with biofilms (Sun, D., et al., *Clin. Diagn. Lab. Immunol.* (2005) 12:93-100; Shahrooei, M., et al., *Infect. Immun.* (2009) 77:3670-3678; Novotny, L. A., et al., *Vaccine* (2009) 28:279-289).

The WO2011/123396 PCT application describes the use of polyclonal and monoclonal antibodies generated against a particular DNABII protein (*E. coli* integration host factor (IHF)) to treat an animal model of the common ear infection (otitis media) and an animal model for periodontal disease. It also describes generating active immunity by providing the protein, or peptides representing the protein to a subject. The present invention provides improved agents for passive immunity. The epitopes for two such monoclonal antibodies have been identified at the level of individual amino acids and are disclosed herein. One of these antibodies, TRL1068, was disclosed by the present applicants in PCT application US2014/057771. The non-identical but overlapping epitopes identify a region of the protein that is conformational with regard to the linear sequence of the IHF/HU protein, and thereby identifies favorable conformational features for an immunogen intended to generate an immune response with efficacy for interfering with a biofilm. Identification of the conformational nature of the epitope is also useful in the design of screening reagents for discovery of monoclonal antibodies or other homogeneous agents with biofilm disrupting activity and for affinity purification of such agents.

DISCLOSURE OF THE INVENTION

The invention provides homogeneous compositions of binding moieties, such as aptamers, protein mimics of antibodies or monoclonal antibodies or fragments thereof, that are particularly effective in binding DNABII proteins and thus effective in dissolving biofilms. The most significant DNABII proteins are the alpha and beta subunits of IHF and the alpha and beta subunits of HU proteins. In general, gram-positive bacteria have either the HU-alpha subunit or the HU-beta subunit whereas gram-negative bacteria generally have all four. However, there are exceptions—e.g., *H. influenzae* has three of these but not HU-beta. In the strains described herein, *P. aeruginosa* has all four of these subunits whereas *S. aureus* contains only HU-beta.

Thus, the invention in one aspect is directed to a binding moiety such as a monoclonal antibody (mAb) that has affinity for at least one DNABII protein that exceeds the affinity of branched DNA, a component of biofilms, for said protein. Some affinities for non-sequence-specific DNA binding by these proteins are disclosed in Chen, C. et al, *Biochem. J.* (2004) 383:343-351, Aeling, K. A., et al., *J. Biol. Chem.* (2006) 281:39236-39248 and Swinger, K. K., et al., *J. mol. Biol.* (2007) 365:1005-1016. The affinities span a broad range, but have in common the feature of being sufficiently weak that the DNABII protein would be expected to desorb and re-bind to the biofilm over the course of minutes to hours. A high affinity mAb can thereby extract the protein by preventing re-binding, leading to gradual dissolution of the biofilm. Gradual dissolution is useful for avoiding release of large numbers of bacteria at once that could induce a deleterious cytokine storm reaction, and for avoiding release of large fragments of the biofilm that could occlude blood vessels. One class of binding moieties—especially mAb—is that wherein binding is to the conformational epitope in SEQ ID NO:80. It is particularly preferred that any antibodies to be used systemically be compatible with mammalian subjects, especially human subjects or feline, canine, porcine, bovine, ovine, caprine or equine subjects when proposed for use in these subjects. Such native mAbs or mAbs modified to more resemble the selected species—i.e., humanized or "species-ized"—have lower risk of being rejected as foreign proteins, particularly upon repeated administration. Those actually derived from the species of interest have reduced risk of binding to other proteins in the body than mAbs from other sources and thus pose lower toxicity risk. Also preferred is the property of binding with sufficient affinity so as to dissolve or prevent formation of biofilm derived from DNABII proteins originating from at least two different bacterial species. In the case of mAbs, such mAbs may be characterized as an Fv antibody, a bispecific antibody, a chimeric antibody, species-ized antibody or a complete antibody, wherein said complete antibody comprises generic constant regions heterologous to the variable regions thereof.

In some embodiments, the mAbs comprise variable regions encoded by nucleic acid isolated from B cells of a human not immunized with DNABII protein or with a fragment thereof. In some embodiments, the screening is performed by reacting antibodies secreted by said B cells with full-length DNABII protein, especially IHF and/or HU protein.

Specific binding moieties illustrated herein contain at least the CDR regions of the heavy chains, and optionally the light chains of the mAbs TRL1068, TRL1070, TRL1087, TRL1215, TRL1216, TRL1218, TRL1230, TRL1232, TRL1242, TRL1245, TRL1330, TRL1335, TRL1337, TRL1338, TRL1341, TRL1347 and TRL1361. However, other types of binding moieties, such as aptamers, modifications of antibodies such as camel type single-chain antibodies and the like are also included within the scope of the invention. Examples of antibody mimics include scaffolds based on fibronectin, lipocalin, lens crystallin, tetranectin, ankyrin, Protein A (Ig binding domain). Small peptide families may also have antibody-like affinity and specificity, including avian pancreatic peptides and conotoxins. Peptide nucleic acids, and "stapled" (cross-linked) peptides similarly provide the ability to generate high affinity binding agents with well-defined specificity. All of these classes share the property of having a large number of potential binding agents, from which a single homogeneous agent is chosen. Homogeneous agents are preferred drug candidates compared to, for example, polyclonal antisera for both ease of manufacturing and reduced risk of off-target binding activity that could lead to toxicity.

The invention is further directed to a method to treat a biofilm associated with an industrial process by using the binding moieties of the invention either to dissolve biofilms or prevent their formation. In this instance, the species origin of the mAbs is not of concern. These binding moieties may also be applied topically on a subject to dissolve biofilms characteristic of a condition in said subject or to prevent their formation. The binding moieties may also be administered systemically for treatment of biofilms.

Thus, the invention further includes pharmaceutical or veterinary compositions which comprise the binding moiety described above in an amount effective to treat or prophylactically inhibit the formation of biofilm due to infection in animal subjects.

In still other aspects, the invention is directed to recombinant materials and methods to prepare binding moieties of the invention that are proteins, e.g., mAbs, and to improved recombinant methods to prepare DNABII proteins.

In other aspects, the invention is directed to novel expression systems for DNABII proteins to be used as immunogens and to methods to use these DNABII proteins to identify an agent that reverses drug resistance in multiple species of bacteria. In one embodiment, B cells obtained from a human or other mammal not immunized with DNABII protein or fragment thereof are screened by testing the antibodies secreted by said B cells with the full-length protein obtained. Nucleic acid isolated from said cells may then be combined with nucleic acid encoding the relevant constant regions to prepare the mAbs of the invention recombinantly. Alternatively, the variable regions may be prepared as Fv single-chain antibodies, for example.

The invention also relates to specific isolated peptides and peptidomimetics that mimic the conformational epitope defined jointly by studies using TRL1068, TRL1330 and TRL1337, as well as to methods for generating antibodies to DNABII proteins by using these specific peptides or peptidomimetics as immunogens. These peptides may also be used to detect B cells that secrete desired antibodies in individuals that have not been specifically immunized.

Synthetic compounds that mimic the epitope that bind the antibodies of the invention, such as TRL1068, TRL1330 and TRL1337 may also be used to screen libraries of candidate binding moieties to identify those that will successfully dissolve biofilms. The binding moieties may be nucleic acids resulting in suitable aptamers or may be libraries of homologs that can behave as binding moieties such as scaffolds based on ankyrin, tetranectin, and the like.

In still another aspect, the invention is directed to a method to treat human or animal diseases for which biofilm causes drug resistance. Treatments include vaccination with immunogens that mimic the conformational epitope defined by the epitopes for TRL1068, TRL1330 and TRL1337, as well as treating subjects with the resulting sera (or concentrated antigen binding polyclonal antibodies from such sera), or with specific monoclonal antibodies developed from the B cells of such immunized animals. Examples of medical indications include: heart valve endocarditis (for which surgical valve replacement is required in the substantial fraction of cases that cannot be cured by high dose antibiotics due to the resistance associated with biofilm), chronic non-healing wounds (including venous ulcers and diabetic foot ulcers), ear and sinus infections, urinary tract infections, pulmonary infections (including subjects with cystic fibrosis or chronic obstructive pulmonary disease), catheter associated infections (including renal dialysis subjects), subjects with implanted prostheses (including hip and knee replacements), and periodontal disease.

This method is effective in mammalian subjects in general, and thus is also applicable to household pets, including periodontal disease in dogs which is difficult to treat due to biofilm (Kortegaard, H. E., et al., *J. Small Anim. Pract.* (2008) 49:610-616). Similarly, the invention has utility for treating farm animals, including dairy cattle with mastitis due to bacterial infections (Poliana de Castro Melo, et al., *Brazilian J. Microbiology* (2013) 44:119-124). For the veterinary indications in particular, hyperimmunization of donor animals provides a cost effective route to large amounts of serum suitable for use in localized delivery to other members of the same animal species, e.g., to the gums for periodontal disease or to the udders for mastitis. Extraction of antigen binding antibodies from serum provides a more concentrated source of antibodies for this purpose. For such extraction, substantial quantities of the DNABII protein are needed, which can be provided by the recombinant production method disclosed herein. Alternatively, mimics of the conformational epitope can be used for such extraction.

MODES OF CARRYING OUT THE INVENTION

The invention includes various binding moieties of a monoclonal or homogeneous nature that can dissolve biofilms. "Monoclonal" means that the binding moieties can form a homogeneous population analogous to the distinction between monoclonal and polyclonal antibodies. In one important embodiment, the exemplified binding moieties are mAbs or fragments thereof. In most embodiments, the binding moieties have affinity for at least one DNABII protein in the low nanomolar range—i.e., the Kd is in the range of 10 nM-100 nM including the intervening values, such as 25 nM or 50 nM, but may also be <10 nM or less than 100 pM or less than 40 pM as preferred embodiments.

Figure 2:
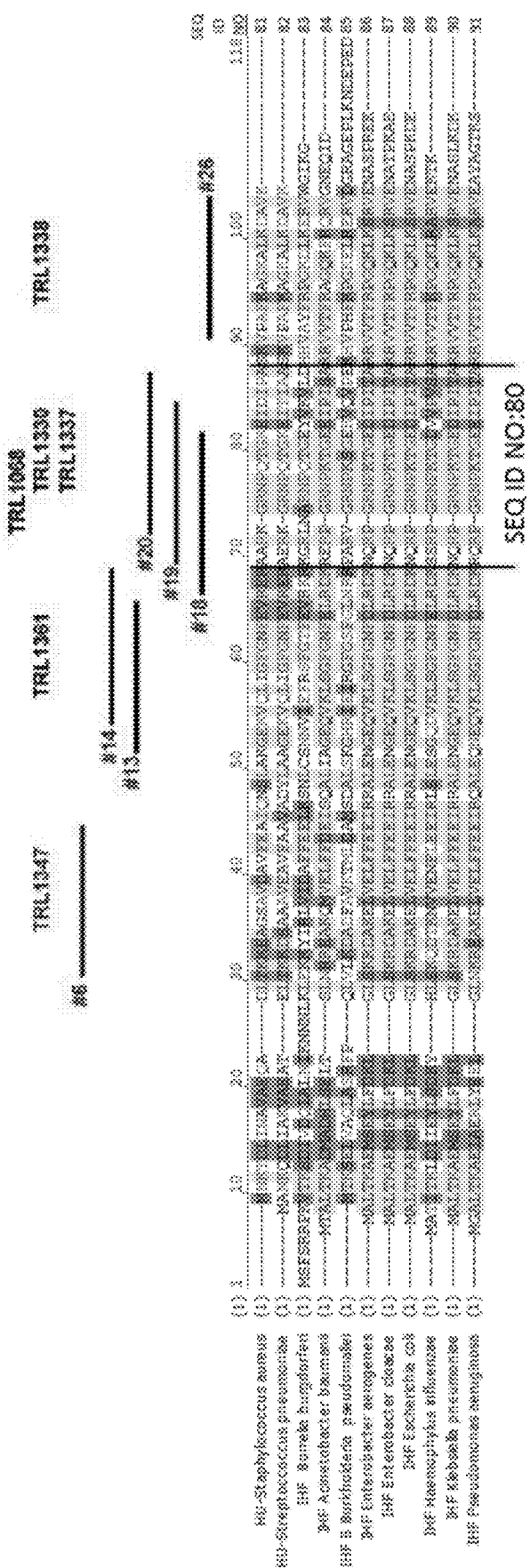
FIG. 2 provides sequences and shows the locations of the empirically defined epitopes of key mAbs of the invention in DNABII (IHF/HU) proteins of various bacterial species SEQ ID NO:81-SEQ ID NO:91.

These affinities should be, in some embodiments, characteristic of the interaction with the biofilm-forming proteins derived from a multiplicity of bacterial species, at least two, three, four or more separate species. In some embodiments, particularly high affinities represented by values less than 100 pM or less than 40 pM are exhibited across at least three species, and in particular wherein these species are *Staphylococcus aureus*, *Pseudomonas aeruginosa*, and *Klebsiella pneumoniae*. However, assurance of binding across multiple species can also be achieved by exhibiting a high affinity with respect to an epitope that is highly conserved across multiple species. As described below, the epitope for both TRL1068 and TRL1330 has been mapped to within residues corresponding to SEQ ID NO:80 of *Staphylococcus aureus*, HU-beta which is in the most highly conserved part of the protein among bacterial species (FIG. 2).

As noted in the examples below, the invention includes a number of specific antibodies that have been shown to bind with high affinity to various epitopes of *Staphylococcus aureus* HU-beta. These include, in addition to TRL1068, mAbs designated TRL1070, TRL1087, TRL1215, TRL1216, TRL1218, TRL1230, TRL1232, TRL1245, TRL1330, TRL1335, TRL1337, TRL1338, TRL1341, TRL1347, TRL1361 and antibodies that compete with each of these for binding to a DNABII protein.

For use in treatment of bacterial infection in humans, the binding moieties of the invention should have at least three characteristics in order to be maximally useful: the binding moiety should be compatible with the treated species—e.g., in the case of monoclonal antibodies for treating humans, either human or humanized. The binding moiety should have an affinity for the biofilm-forming DNABII protein that exceeds the affinity of that protein for other components of the biofilm that includes this DNABII protein, and it should be crossreactive across the DNABII homologs from multiple bacterial species, minimally two or three such species including both Gram positive and Gram negative species, but preferably a greater number, such as four, five or six or more.

Similar characteristics are relevant for use of the binding moieties of the invention for treatment of conditions in other species. In this case, the antibodies are compatible with the species in question. Thus, the antibodies may be derived from feline, canine, equine, bovine, caprine, ovine or porcine species or may be adapted from antibodies of other animals. Analogous to "humanized," these antibodies could be called "species-ized" so that the relevant species is adequately addressed. Alternatively, a functionally restricted polyclonal antibody preparation can be prepared by generation of antibodies in serum of subjects immunized with peptides that mimic the conformational epitope defined by human mAbs TRL1068, TRL1330 and TRL1337, with further narrowing of the specificity accomplished by affinity purification using either intact DNABII protein or an epitope mimic. This approach is more appropriate for veterinary indications than for human use. Hyperimmunization of animals to generate the serum is ethically acceptable, but is not feasible for humans; and the risk of adverse events from a polyclonal antiserum is more acceptable for treatment of animals than for treatment of humans. Indeed, as exemplified below, suitable B cells can be screened for antibodies immunoreactive with full-length DNABII proteins in humans that have not been immunized with either the DNABII protein itself or with a fragment thereof. In addition to antisera per se, specific monoclonal antibodies can be prepared by screening B cells of the subject for secretion of antibodies that are immunoreactive with, for example, the full-length protein in question which contains the epitope from which the mimic was derived. Concurrent screening with more than one DNABII protein can assist in identifying mAbs that show cross-species binding. Nucleic acid contained in successful B cells can then be extracted and used to prepare monoclonal antibodies recombinantly.

As the illustrative antibodies disclosed herein in the examples below contain variable regions that are derived from humans, and constant regions which are cloned independently of said variable regions but are also derived from humans, these antibodies offer particular advantages for repeated use in humans. When the subject to be administered the mAb is non-human, it is advantageous for repeated use to administer native mAbs similarly derived from that species. Alternatively, an equivalent of the human variable regions, optionally fused to an Fc region from the host species to be treated, may be used. This variable region may be, in some embodiments, an Fab portion or a single-chain antibody containing CDR regions from both the heavy and light chains or heavy chain only. Bispecific forms of these variable regions equivalents can also be constructed, with numerous constructs described in the literature. Although the typical "mAb" will be a protein or polypeptide ("proteins," "polypeptide" and "peptide" are used interchangeably herein without regard to length) for use in subjects, the mAbs may also be supplied via delivery of nucleic acids that then generate the proteins by in situ translation in cells of the subject. In addition, nucleic acid molecules that mimic the binding characteristics of these polypeptides or proteins can be constructed—i.e., aptamers can be constructed to bind molecules that are identified as described below by their ability to mimic the binding moieties. Successful mimicry of these aptamers for the protein-based binding moieties can be verified both biochemically and functionally to confirm that the affinity of the aptamer is sufficient for therapeutic efficacy. In light of the well-defined conformationally constrained region that includes the epitopes for TRL1068, TRL1330 and TRL1337, preparation of such aptamers is straightforward using well established methods (Lin, H., et al., *Biomicrofluidics* (2014) 8:041501).

In more detail, in one embodiment, the aptamers or other binding moieties such as alternative antibody scaffolds can be identified by screening libraries comprising candidate aptamers or alternative binding moieties with mimics of epitopes that bind, specifically, the mAbs of the invention shown to be successful herein—e.g., TRL1068 or TRL1330. In one embodiment, for example, TRL1068 can itself be used to screen libraries of candidate mimics and compounds that successfully bind TRL1068 can then, in turn, be used to screen libraries of candidate aptamers or alternative binding moieties.

With respect to protein-based monoclonal binding moieties, in addition to typical monoclonal antibodies or fragments thereof that are immunologically specific for the same antigen, various forms of other scaffolding, including single-chain antibody forms such as those derived from camel, llama or shark could be used as well as antibody mimics based on other scaffolds such as fibronectin, lipocalin, lens crystallin, tetranectin, ankyrin, Protein A (Ig binding domain), or the like. Short structured peptides may also be used if they provide sufficient affinity and specificity, e.g., peptides based on inherently stable structures such as conotoxins or avian pancreatic peptides, or peptidomimetics that achieve stable structures by crosslinking and/or use of non-natural amino acids (Josephson, K., et al., *J. Am. Chem. Soc.* (2005) 127:11727-11725). In general, "monoclonal antibody (mAb)" includes all of the foregoing. As for aptamers, generation of such molecules is straightforward using well established methods.

As used herein, the term "antibody" includes immunoreactive fragments of traditional antibodies even if, on occasion, "fragments" are mentioned redundantly. The antibodies, thus, include Fab, F(ab')$_2$, F$_v$ fragments, single-chain antibodies which contain substantially only variable regions, bispecific antibodies and their various fragmented forms that still retain immunospecificity and proteins in general that mimic the activity of "natural" antibodies by comprising amino acid sequences or modified amino acid sequences (i.e., pseudopeptides) that approximate the activity of variable regions of more traditional naturally occurring antibodies.

In particular, in the case of embodiments which are monoclonal antibodies, fully human antibodies which are, however, distinct from those actually found in nature, are typically prepared recombinantly by constructing nucleic acids that encode a generic form of the constant region of heavy and/or light chain and further encode heterologous variable regions that are representative of human antibodies. Other forms of such modified mAbs include single-chain antibodies such that the variable regions of heavy and light chain are directly bound without some or all of the constant regions. Also included are bispecific antibodies which contain a heavy and light chain pair derived from one antibody source and a heavy and light chain pair derived from a different antibody source. Similarly, since light chains are often interchangeable without destroying specificity, antibodies composed of a heavy chain variable region that determines the specificity of the antibody combined with a heterologous light chain variable region are included within the scope of the invention. Chimeric antibodies with constant and variable regions derived, for example, from different species are also included.

For the variable regions of mAbs, as is well known, the critical amino acid sequences are the CDR sequences arranged on a framework which framework can vary without necessarily affecting specificity or decreasing affinity to an unacceptable level. Definition of these CDR regions is accomplished by art-known methods. Specifically, the most commonly used method for identifying the relevant CDR regions is that of Kabat as disclosed in Wu, T. T., et al., *J. Exp. Med.* (1970) 132:211-250 and in the book Kabat, E. A., et al. (1983) *Sequence of Proteins of Immunological Interest*, Bethesda National Institute of Health, 323 pages. Another similar and commonly employed method is that of Chothia, published in Chothia, C., et al., *J. Mol. Biol.* (1987) 196: 901-917 and in Chothia, C., et al., *Nature* (1989) 342:877-883. An additional modification has been suggested by Abhinandan, K. R., et al., *Mol. Immunol.* (2008) 45:3832-3839. The present invention includes the CDR regions as defined by any of these systems or other recognized systems known in the art.

The specificities of the binding of the mAbs of the invention are defined, as noted, by the CDR regions mostly those of the heavy chain, but complemented by those of the light chain as well (the light chains being somewhat interchangeable). Therefore, the mAbs of the invention may contain the three CDR regions of a heavy chain and optionally the three CDR's of a light chain that matches it. The invention also includes binding agents that bind to the same epitopes as those that actually contain these CDR regions. Thus, for example, also included are aptamers that have the same binding specificity—i.e., bind to the same epitopes as do the mAbs that actually contain the CDR regions. Because binding affinity is also determined by the manner in which the CDR's are arranged on a framework, the mAbs of the invention may contain complete variable regions of the heavy chain containing the three relevant CDR's as well as, optionally, the complete light chain variable region comprising the three CDR's associated with the light chain complementing the heavy chain in question. This is true with respect to the mAbs that are immunospecific for a single epitope as well as for bispecific antibodies or binding moieties that are able to bind two separate epitopes, for example, divergent DNABII proteins from two bacterial species.

The mAbs of the invention may be produced recombinantly using known techniques. Thus, with regard to the novel antibodies described herein, the invention also relates to nucleic acid molecules comprising nucleotide sequence encoding them, as well as vectors or expression systems that comprise these nucleotide sequences, cells containing expression systems or vectors for expression of these nucleotide sequences and methods to produce the binding moieties by culturing these cells and recovering the binding moieties produced. Any type of cell typically used in recombinant methods can be employed including prokaryotes, yeast, mammalian cells, insect cells and plant cells. Also included are human cells (e.g., muscle cells or lymphocytes) transformed with a recombinant molecule that encodes the novel antibodies.

Typically, expression systems for the proteinaceous binding moieties of the invention include a nucleic acid encoding said protein coupled to control sequences for expression. In many embodiments, the control sequences are heterologous to the nucleic acid encoding the protein.

Bispecific binding moieties may be formed by covalently linking two different binding moieties with different specificities. For example, the CDR regions of the heavy and optionally light chain derived from one monospecific mAb may be coupled through any suitable linking means to peptides comprising the CDR regions of the heavy chain sequence and optionally light chain of a second mAb. If the linkage is through an amino acid sequence, the bispecific binding moieties can be produced recombinantly and the nucleic acid encoding the entire bispecific entity expressed recombinantly. As was the case for the binding moieties with a single specificity, the invention also includes the possibility of binding moieties that bind to one or both of the same epitopes as the bispecific antibody or binding entity/binding moiety that actually contains the CDR regions.

The invention further includes bispecific constructs which comprise the complete heavy and light chain sequences or the complete heavy chain sequence and at least the CDR's of the light chains or the CDR's of the heavy chains and the complete sequence of the light chains.

The invention is also directed to nucleic acids encoding the bispecific moieties and to recombinant methods for their production, as described above.

Multiple technologies now exist for making a single antibody-like molecule that incorporates antigen specificity domains from two separate antibodies (bi-specific antibody). Thus, a single antibody with very broad strain reactivity can be constructed using the Fab domains of individual antibodies with broad reactivity to diverse homologs. Suitable technologies have been described by MacroGenics (Rockville, Md.), Micromet (Bethesda, Md.) and Merrimac (Cambridge, Mass.). (See, e.g., Orcutt, K. D., et al., *Protein Eng. Des. Sel.* (2010) 23:221-228; Fitzgerald, J., et al., *MAbs.* (2011) 1:3; Baeuerle, P. A., et al., *Cancer Res.* (2009) 69:4941-4944.)

The invention is also directed to pharmaceutical and veterinary compositions which comprise as active ingredients the binding moieties of the invention. The compositions contain suitable physiologically compatible excipients such as buffers and other simple excipients. The compositions may include additional active ingredients as well, in particular antibiotics. It is often useful to combine the binding moiety of the invention with an antibiotic appropriate to a condition to be addressed since the efficacy of most antibiotics is greater against the planktonic state of the bacteria than against the sessile, biofilm embedded state. Additional active ingredients may also include immunostimulants and/or antipyrogenics and analgesics.

The binding moieties of the invention may also be used in diagnosis by administering them to a subject and observing any complexation with any biofilm present in the subject. In this embodiment the binding moieties are typically labeled with an observable label, such as a fluorescent or chemiluminescent compound in a manner analogous to labeling with bacteria that produce luciferase for non-invasive detection as described in Chang, H. M., et al., *J. Vis. Exp.* (2011) 10.3791/2547. The assay may also be performed on tissues obtained from the subject. The presence of a biofilm is detected in this manner if it is present, and the progress of treatment may also be monitored by measuring the complexation over time. The identity of the infectious agent may also be established by employing binding moieties that are specific for a particular strain or species of infectious agent. For diagnostic purposes, it is particularly favorable to target epitopes that are not sterically occluded when the protein is complexed with DNA. For example the epitope of TRL1361 has been determined to lie outside the contact sites with DNA. Antibodies such as this also provide the opportunity to construct sandwich immunoassays, wherein one antibody is used to capture the antigen and a second antibody that binds at a different site is used to detect the captured antigen.

Such assays provide high specificity and are common in the field of diagnostics, with particular utility in a multiplexed assay to reduce the effect of antibody cross-reactivity to other antigens.

The invention also includes a method for identifying suitable immunogens for use to generate antibodies which method includes assessing the binding of the binding moieties of the invention, such as mAbs described above, to a candidate peptide or other epitope mimicking molecule. This is an effective method, not only to identify suitable immunogens, but also to identify compounds that can be used as a basis for designing aptamers that mimic the binding moieties of the invention. The method is grounded in the fact that if a vaccine immunogen cannot bind to an optimally effective mAb, it is unlikely to be able to induce such antibodies. Conversely, an immunogen that is a faithful inverse of the optimal mAb provides a useful template for constructing a mimic of the optimal mAb. In its simplest form, this method employs a binding moiety such as one of the mAbs of the invention as an assay component and tests the ability of the binding moiety to bind to a candidate immunogen in a library of said candidates. The invention further includes identification of the conformationally restricted region defined by the overlap of the epitopes for TRL1068, TRL1330 and TRL1337 as a particularly favorable starting point for such immunogen optimization.

Thus, the binding moieties of the invention may be used in high throughput assays to identify from combinatorial libraries of compounds or peptides or other substances those substances that bind with high affinity to the binding moieties of the invention. General techniques for screening combinatorial or other libraries are well known: Glokler, J., et al., *Molecules* (2010) 15:2478-2490. It may be advantageous to establish affinity criteria by which effective candidate immunogens or other binding partners of the binding moieties of the invention can be selected. The binding moiety, then, can become a template for the design of an aptamer that will bind an epitope of the DNABII protein, preferably across a number of species, but which contains too few nucleotides to act as a structural component in a biofilm. Thus, the resulting aptamers are composed of only 25 or less oligonucleotides, preferably 10-20 nucleotides which are sufficient to effect binding, but not sufficient to behave as structural components for biofilms. A corresponding number of individual monomers would be characteristic of nucleic acid mimics, such as peptide nucleic acids as well.

In one particular example, the immunogen discussed above could be a peptide that represents an epitope to which the binding moiety is tightly bound. The binding moiety may be an mAb, and this is particularly favorable if the binding moiety or mAb is crossreactive with regard to the DNABII protein across a number of species. The epitope then represents a template which can form the basis for forming aptamers—i.e., short species of DNA or suitable DNA analogs such as peptide nucleic acids which can then behave as agents to bind the DNABII proteins thus preventing these proteins from forming the biofilms that would result from interaction with longer forms of DNA. Such chemically sturdy mimics could be used, for example, to coat pipes in industrial settings thus permitting sequestering of DNABII proteins to prevent biofilm formation. Due to the lower immunogenicity, mAbs are generally preferable as pharmaceuticals, but such aptamer mimics are also potentially useful as pharmaceuticals, again, by virtue of their ability to prevent binding of DNABII proteins to longer forms of DNA for formation of biofilms.

In addition, the ability of the binding moieties of the invention to overcome drug resistance in a variety of bacteria can be assessed by testing the binding moieties of the invention against a panel or library of DNABII proteins from a multiplicity of microbial species. Binding moieties that are able to bind effectively a multiplicity of such proteins are thus identified as suitable not only for dissolving biofilms in general, but also as effective against a variety of microbial strains. It is also useful to identify binding moieties that have utility in acidic environments wherein the affinity of a candidate binding moiety for a DNABII protein over a range of pH conditions is tested and moieties with a low nanomolar affinity at pH 4.5 are identified as having utility in acidic environments.

The binding moieties of the invention are also verified to have an affinity with respect to at least one DNABII protein greater than the affinity of a biofilm component for the DNABII protein which comprises comparing the affinity of the binding moiety for the DNABII protein versus the affinity of a component of the biofilm, typically branched DNA, for the DNABII protein. This can be done in a competitive assay, or the affinities can be determined independently.

The DNABII proteins used in these assays may be prepared in mammalian cells at relatively high yield, thereby overcoming difficulties in expressing these proteins in bacteria. Specifically, the full-length DNABII proteins of the invention can be prepared for any purpose, including as reagents for screening B cells for antibody secretion by culturing mammalian cells comprising suitable expression vectors that include nucleic acids encoding the full-length forms of these proteins. One aspect of the invention is the successful production of full-length DNABII proteins by recombinant production in mammalian cell culture.

All of the assays above involve assessing binding of two prospective binding partners in a variety of formats.

A multitude of assay types are available for assessing successful binding of two prospective binding partners. For example, one of the binding partners can be bound to a solid support and the other labeled with a radioactive substance, fluorescent substance or a colorimetric substance and the binding of the label to the solid support is tested after removing unbound label. The assay can, of course, work either way with the binding moiety attached to the solid support and a candidate immunogen or DNABII protein labeled or vice versa where the candidate is bound to solid support and the binding moiety is labeled. Alternatively, a complex could be detected by chromatographic or electrophoretic means based on molecular weight such as SDS-page. The detectable label in the context of the binding assay can be added at any point. Thus, if, for example, the mAb or other binding moiety is attached to a solid support the candidate immunogen can be added and tested for binding by supplying a labeled component that is specific for the candidate immunogen. Hundreds of assay formats for detecting binding are known in the art, including, in the case where both components are proteins, the yeast two-hybrid assay.

In addition to this straightforward application of the utility of the binding moieties of the invention, the identification of a suitable powerful immunogen can be determined in a more sophisticated series of experiments wherein a panel of mAbs against the DNABII protein is obtained and ranked in order by efficacy. A full suite of antibodies or other binding moieties can be prepared against all possible epitopes by assessing whether additional binding moieties compete for binding with the previous panel of members. The epitopes for representative binding mAbs for each member of the complete suite can be accomplished by binding to a peptide array representing the possible overlapping epitopes of the immunogen or by X-ray crystallography, NMR or cryo-electron microscopy. An optimal vaccine antigen would retain the spatial and chemical properties of the optimal epitope defined as that recognized by the most efficacious mAbs as compared to less efficacious mAbs but does not necessarily need to be a linear peptide. It may contain non-natural amino acids or other crosslinking motifs.

Thus, even beyond the specific mAbs set forth herein, optimal immunogens can be obtained, which not only are useful in active vaccines, but also as targets for selecting aptamers. Specifically, in addition to the peptide of SEQ ID NO:80, positions 5-20 of peptides of SEQ ID NOS:71-73 and 75-79 are identified.

Another aspect of the invention is a method to prepare higher yields of the bacterial/microbial DNABII proteins which are typically difficult to express at high levels in bacteria possibly due to toxicity to those cells. The standard method for preparation of these proteins is described by Nash, H. A., et al., *J. Bacteriol* (1987) 169:4124-4127 who showed that the IHF of *E. coli* could be effectively prepared if both chains of said protein (IHF alpha and IHF beta) are produced in the same transformant. Applicants have found that they are able to obtain higher yields, as much as 5-10 mg/l of IHF, by producing homodimers transiently in the mammalian cell line HEK293 using a widely available expression vector. Similar results are obtained for DNABII proteins in general. The expression of bacterial proteins that are toxic at high levels in bacteria is conveniently achieved in mammalian cells especially for those without glycosylation sites that would result in modification of the proteins when thus expressed. If tagged with a polyhistidine, purification of the resulting protein can be readily achieved.

Applications

The binding moieties of the invention including antibodies are useful in therapy and prophylaxis for any subject that is susceptible to infection that results in a biofilm. Thus, various mammals, such as bovine, ovine and other mammalian subjects including horses and household pets and humans will benefit from the prophylactic and therapeutic use of these mAbs.

The binding moieties of the invention may be administered in a variety of ways. The peptides based on CDR regions of antibodies, including bispecific and single chain types or alternate scaffold types, may be administered directly as veterinary or pharmaceutical compositions with typical excipients. Compositions that comprise micelles or other nanoparticles of various types may be useful for extending the duration of treatment. Aptamers that behave as binding agents similar to mAbs can be administered in the same manner. Further, the binding agent may be conjugated to any of the solid supports known in the literature, such as PEG, agarose or a dextran, to function as an immunosorbent for extracting DNABII from a biofilm. Alternatively, the peptide-based mAbs may be administered as the encoding nucleic acids either as naked RNA or DNA or as vector or as expression constructs. The vectors may be non-replicating viral vectors such as adeno associated virus vectors (AAV) or the encoding nucleic acid sequence may be chemically or physically delivered into cells (Suskovitch, T. J., and Alter, G., *Expert Rev Vaccines* (2015) 14:205-219). Use of nucleic acids as drugs as opposed to their protein counterparts is helpful in controlling production costs.

These are administered in a variety of protocols, including intravenous, subcutaneous, intramuscular, topical (particularly for chronic non-healing wounds and periodontal disease), inhaled and oral or by suppository. Similar routes of administration can be used with regard to the binding moieties themselves. One useful way to administer the nucleic acid-based forms of either the binding moieties themselves (aptamers) or those encoding the protein form of binding moieties is through a needleless approach such as the agro-jet needle-free injector described in US2001/0171260.

The peptides that include the epitopes of the high affinity, cross-species binding human mAbs against DNABII proteins as described herein are also useful as active components of vaccines to stimulate immunogenic responses which will generate antibodies in situ for disruption of biofilms. The types of administration of these immunogens or peptidyl mimetics that are similarly effective are similar to those for the administration of binding moieties, including various types of antibodies, etc. Liposomal compositions that comprise micelles or other nanoparticles of various types may also be used to enhance immunogenicity. The peptidomimetics may themselves be in the form of aptamers or alternative structures that mimic the immunogenic peptides described herein. For those immunogens, however, that are proteins or peptides, the administration may be in the form of encoding nucleic acids in such form as will produce these proteins in situ. The formulation, routes of administration, and dosages are determined conventionally by the skilled artisan.

As shown in the examples below, two antibodies of the invention, TRL1068, TRL1330 and TRL1337 have particularly favorable affinity and specificity characteristics for the DNABII protein. Therefore, immunogens that bind these specific antibodies will be particularly powerful in generating effective antisera. By analyzing overlapping peptides and alanine replacements, it has been found that the epitopes for both of these highly binding antibodies are conformational epitopes located on a short anti-parallel beta sheet connected by a loop (a "beta hairpin"). These are shown in FIG. 4. Since these structures are now known, it is well within the skill of the art to construct peptidyl mimetics which preserve the conformation of the sequence, for example by crosslinking to lock in the conformation, and render it more effective than simply the linear peptide representing the epitope itself and to substitute, for example, non-natural amino acids or other than peptide bonds to render the immunogen more stable and resistant to hydrolysis. It is also possible to design alternative non-peptide mimics including peptide nucleic acids that have essentially the same shape and binding characteristics as the now identified immunogen. Focusing on the short stretch of beta sheet defined herein is advantageous for constructing epitope mimics.

As set forth in Example 2 below, as the epitopes to which TRL1068 and TRL1330 bind are in the form of a conformational epitope, methods are available in the art to provide peptidomimetics that are useful as immunogens. Such methods are disclosed in (Jimenez, M. A., *Methods Mol. Biol.* (2014) 1216:15-52), including design of artificial cross-linkers to stabilize the structure (Celentano, V., et al., *Chem. Commun* (*Camb.*) (2012) 48:762-764). Mimetics of this type of structure have been generated that mimic the binding of HIV Tat protein to RNA with low nM affinity (Athanassiou, Z., et al., *Biochemistry* (2007) 46:741-751), and a beta hairpin mimic has been described that binds to VEGF receptor-2 with low nM affinity (Patel, S., et al., *Protein Eng. Des. Sel*. (2013) 26:307-315). Construction of mimics is also described in Schmidt, J., et al., *Bioorganic. Med. Chem.*

(2013) 21:5806-5810 and in Lesniak, W. G., et al., *Mol. Pharm.* (2015) 12:941-953. Briefly, small libraries of cross-linked or cyclic compounds based on the structure of the beta hairpin can be constructed and evaluated for structure/activity relationships by means of competition assays wherein the stabilized beta hairpin structure that includes the epitopes is used to compete with candidate peptidomimetics binding to the relevant antibody, e.g., TRL1068. Those candidates that successfully compete with the native epitope are selected as suitable immunogens.

The types of conditions for which the administration either of the vaccine type for active generation of antibodies for biofilm control or for passive treatment by administering the antibodies, per se, include any condition that is characterized by or associated with the formation of biofilms. These conditions include: heart valve endocarditis, both native and implanted (for which a substantial fraction of cases cannot be cured by high dose antibiotics due to the resistance associated with biofilm), chronic non-healing wounds (including venous ulcers and diabetic foot ulcers), ear and sinus infections, urinary tract infections, pulmonary infections (including subjects with cystic fibrosis or chronic obstructive pulmonary disease), catheter associated infections (including renal dialysis subjects), subjects with implanted prostheses (including hip and knee replacements), and periodontal disease.

One particular condition for which biofilms have been implicated is Lyme disease. It has been shown that the relevant bacteria can form a biofilm in vitro and this is thought to be a substantive contributor to the prolonged course of the disease and resistance to antibiotics. The incidence is more than 30,000 cases per year in the U.S. An alignment of the HU (single gene) from *Borrelia burgdorferi* which is the causative bacteria shows high similarity to other IHF/HU genes in the putative epitope. Thus, the treatment of Lyme disease specifically as an indication is a part of the invention. The isolation of *B. burgdorferi* genes encoding HU was described by Tilly, K., et al., *Microbiol*. (1996) 142:2471-2479 and characterization of the biofilm formed by these organisms in vitro was described by Sapi, E., et al., *PLoS* 1 (2013) 7:e1848277. Similar biofilms have been observed in vivo by Sapi, E., et al., *Eur. J. Microbiol. and Immunol*. (2016) 6(1):9-24.

For use in diagnosis, the binding moieties can be used to detect biofilms in vivo by administering them to a subject or in vitro using tissue obtained from the subject. Detection of complexation demonstrates the presence of biofilm. Detection is facilitated by conjugating the binding moiety to a label, such as a fluorescent, chemiluminescent or radioactive label, or in the case of in vitro testing, with an enzyme label. Many such fluorescent, chemiluminescent, radioactive and enzyme labels are well known in the art. Treatment course can also be monitored by measuring the disappearance of biofilm over time. The diagnostic approach enabled by the invention is much less complex than current methods for, for example, endocarditis, where the current diagnostic is trans-esophageal echocardiogram. In addition, the detection/quantitation method can be used in evaluating the effectiveness of compounds in dissolving or inhibiting the formation of biofilms in laboratory settings. Conjugates of the binding moieties of the invention with detectable labels are generally useful in detection and/or quantitation of biofilms in a variety of contexts.

A particularly useful antibody for imaging is an antibody that binds to an epitope on the DNABII protein that does not interact with DNA since the binding will not require competition with DNA for association with the biofilm. As shown in Example 2 below, TRL1361 is such an antibody and is particularly useful in the detection methods set forth in the previous paragraph.

In addition, since it is now clear that antibodies are available that bind different epitope sites, sandwich assays become available wherein, for example, TRL1068 or TRL1330 or an antibody that binds an epitope other than that bound by TRL1361 is used as either the capture or labeling antibody and TRL1361 is used as the opposite member—for example, wherein TRL1361 is used as a capture antibody and TRL1068 is provided with a label.

As noted above, the binding moieties of the invention are not limited in their utility to therapeutic (or diagnostic) uses, but can be employed in any context where a biofilm is a problem, such as pipelines or other industrial settings. The mode of application of these binding moieties to the biofilms in these situations, again, is conventional.

For example, surfaces associated with an industrial or other setting can be coated with the binding moieties of the invention including the aptamers described above. This effects absorption of the DNABII protein and prevents formation of biofilms. The binding moieties of the invention may also be applied to the biofilms directly to effect dissolution.

The following examples are offered to illustrate but not to limit the invention.

Example 1

Preparation of Antibodies

Human peripheral blood mononuclear cells (PBMC's) were obtained from anonymized blood bank donors, under informed consent. The cells were subjected to the CellSpot™ assay, a micro-assay that detects cells that secrete antibodies that bind a defined antigen, to determine their ability to bind the DNABII protein derived from one or more bacterial species. The DNABII protein used to screen was full length DNABII prepared in mammalian cells. The full length proteins used were HU from *Staphylococcus aureus*; IHF from *Klebsiella pneuomoniae*; and IHF from *Haemophilus influenzae*. The CellSpot™ assay is described in U.S. Pat. Nos. 7,413,868 and 7,939,344. After isolating the B cells from whole blood, they were stimulated with cytokines and mitogens to initiate a brief period of proliferation and antibody secretion (lasting ~5 days) and plated for subjection to the assays; the encoding nucleic acids for the variable regions were extracted and used to produce the antibodies recombinantly following fusion of the variable region encoding DNA to DNA cloned independently that codes for the constant region of the antibody.

Antibodies were selected from over 5 million B cells based on binding to at least one of the DNABII proteins screened. These antibodies: TRL1068, TRL1070, TRL1087, TRL1215, TRL1216, TRL1218, TRL1230, TRL1232, TRL1242, TRL1245, TRL1330, TRL1335, TRL1337, TRL1338, TRL1341, TRL1347 and TRL1361 were characterized by affinity as measured by adsorption ELISA.

This result establishes the feasibility of a focused screen to isolate high affinity, cross-strain binding antibodies. Recovery of such antibodies from human blood is unexpected, since no immunogen was provided, and the low frequency of such mAbs underscores the unpredictability of their presence. As described in PCT WO2011/123396 (FIG. 13), IHF complexed to DNA induces a robust immune response that is directed towards specific regions of IHF that are not protective whereas the immune response to IHF not complexed to DNA induced the formation of highly protective antibodies. The natural state of the protein is in the form of a complex with DNA; that is, the protein is a limiting factor for biofilm formation since addition of exogenous protein increases the amount of biofilm formed (Devaraj, A., et al., *Mol. Microbiol.* (2015 Mar. 11) doi: 10.1111/mmi.12994. Epub ahead of print). Thus, as described in PCT WO2011/123396 the sites that induce a protective response are normally masked by DNA. Despite these facts, several of the mAbs described here that were cloned from human blood bind to sites that are presumed to be in contact with DNA. No immunization with isolated IHF or peptides thereof was required to stimulate the production of such antibodies.

TRL1068 heavy chain variable region has the amino acid sequence:

(SEQ ID NO: 1)
QVQLVESGPGLVKPSETLSLTCRVSGDSNRPSYWSWIRQAPGKAMEWIGY

VYDSGVTIYNPSLKGRVTISLDTSKTRFSLKLTSVIAADTAVYYCARERF

DRTSYKSWWGQGTQVTVSS;

TRL1068 light chain variable region has the amino acid sequence:

(SEQ ID NO: 2)
DIVLTQAPGTLSLSPGDRATLSCRASQRLGGTSLAWYQHRSGQAPRLILY

GTSNRATDTPDRFSGSGSGTDFVLTISSLEPEDFAVYYCQQYGSPPYTFG

QGTTLDIK;

TRL1070 heavy chain variable region has the amino acid sequence:

(SEQ ID NO: 3)
QVQLVQSGGTLVQPGGSLRLSCAASGFTFSYYSMSWVRQAPGKGLEWVAN

IKHDGTERNYVDSVKGRFTISRDNSEKSLYLQMNSLRAEDTAVYYCAKYY

YGAGTNYPLKYWGQGTRVTVSS;

TRL1070 light chain kappa variable region has the amino acid sequence:

(SEQ ID NO: 4)
DILMTQSPSSLSASVGDRVTITCRASQGIRNDLGWYQQKPGKAPKLLIYA

ASSLQSGVPSRFSGSGSGTDFTLTISSLQPEDFATYYCLQDYNYPLTFGG

GTKVEIKR;

TRL1087 heavy chain variable region has the amino acid sequence:

(SEQ ID NO: 5)
QVQLLESGPGLVRPSDTLSLTCTFSADLSTNAYWTWIRQPPGKGLEWIGY

MSHSGGRDYNPSFNRRVTISVDTSKNQVFLRLTSVTSADTAVYFCVREVG

SYYDYWGQGILVTVSS;

TRL1087 light chain kappa variable region has the amino acid sequence:

(SEQ ID NO: 6)
DIEMTQSPSSLSASVGDRITITCRASQGISTWLAWYQQKPGKAPKSLIFS

TSSLHSGVPSKFSGSGSGTDFTLTITNLQPEDFATYYCQQKWETPYSFGQ

GTKLDMIR;

TRL1215 heavy chain variable region has the amino acid sequence:

(SEQ ID NO: 7)
QVQLVESGTEVKNPGASVKVSCTASGYKFDEYGVSWVRQSPGQGLEWMGW

ISVYNGKTNYSQNFQGRLTLTTETSTDTAYMELTSLRPDDTAVYYCATDK

NWFDPWGPGTLVTVSS;

TRL1215 light chain lambda variable region has the amino acid sequence:

(SEQ ID NO: 8)
DIVMTQSPSASGSPGQSITISCTGTNTDYNYVSWYQHHPGKAPKVIIYDV

KKRPSGVPSRFSGSRSGNTATLTVSGLQTEDEADYYCVSYADNNHYVFGS

GTKVTVL;

TRL1216 heavy chain variable region has the amino acid sequence:

(SEQ ID NO: 9)
QVQLVESGGGVVQPGGSLRVSCAASAFSFRDYGIHWVRQAPGKGLQWVAV

ISHDGGKKFYADSVRGRFTISRDNSENTLYLQMNSLRSDDTAVYYCARLV

ASCSGSTCTTQPAAFDIWGPGTLVTVSS;

TRL1216 light chain lambda variable region has the amino acid sequence:

(SEQ ID NO: 10)
DIMLTQPPSVSVSPGQTARITCSGDALPKKYTYWYQQKSGQAPVLLIYED

RKRPSEIPERFSAFTSWTTATLTITGAQVRDEADYYCYSTDISGDIGVFG

GGTKLTVL;

TRL1218 heavy chain variable region has the amino acid sequence:

(SEQ ID NO: 11)
QVQLLESGADMVQPGRSLRLSCAASGFNFRTYAMHWVRQAPGKGLEWVAV

MSHDGYTKYYSDSVRGQFTISRDNSKNTLYLQMNNLRPDDTAIYYCARGL

TGLSVGFDYWGQGTLVTVSS;

TRL1218 light chain lambda variable region has the amino acid sequence:

(SEQ ID NO: 12)
DIVLTQSASVSGSPGQSITISCTGTSSDVGGYNYVSWYQQHPGKAPKLMI

YDVTTRPSGVSDRFSGSKSGNTASLTISGLQAEDEADYYCSSYSSGSTPA

LFGGGTQLTVL;

TRL1230 heavy chain variable region has the amino acid sequence:

(SEQ ID NO: 13)
QVQLVQSGGGLVKPGGSLRLSCGASGFNLSSYSMNWVRQAPGKGLEWVSS

ISSRSSYIYYADSVQGRFTISRDNAKNSLYLQMNSLRAEDTAIYYCARVS

PSTYYYYGMDVWGQGTTVTVSS;

TRL1230 light chain lambda variable region has the amino acid sequence:

(SEQ ID NO: 14)
DIVLTQPSSVSVSPGQTARITCSGDELPKQYAYWYQQKPGQAPVLVIYKD

NERPSGIPERFSGSSSGTTVTLTISGVQAEDEADYYCQSADSSGTYVVFG

GGTKLTVL;

TRL1232 heavy chain variable region has the amino acid sequence:

(SEQ ID NO: 15)
QVQLVESGAEVKKPGALVKVSCKASGYTFSGYYMHWVRQAPGQGLEWMGW

INPKSGGTKYAQKFQGRVTMTRDTSISTAYMELSRLRSDDTAVYFCARGG

PSNLERFLERLQPRYSYDDKYAMDVWGQGTTVTVSS;

TRL1232 light chain kappa variable region has the amino acid sequence:

(SEQ ID NO: 16)
DIVMTQSPGTLSLSPGARATLSCRASQSVSSIYLAWYQQKPGQAPRLLIF

GASSRATGIPDRFSGSGSGTDFTLTISRLEPEDFAVYYCQQYGSSPYTFG

QGTKLEIKR;

TRL1242 heavy chain variable region has the amino acid sequence:

(SEQ ID NO: 17)
QVQLVQSGTEVKKPGESLKISCEGSRYNFARYWIGWVRQMPGKGLDWMGI

IYPGDSDTRYSPSFQGQVSISADKSISTAYLQWNSLKASDTAMYYCARLG

SELGVVSDYYFDSWGQGTLVTVSS;

TRL1242 light chain kappa variable region has the amino acid sequence:

(SEQ ID NO: 18)
DIVLTQSPDSLAVSLGERATINCKSSQSVLDRSNNKNCVAWYQQKPGQPP

KLLIYRAATRESGVPDRFSGSGSGTDFSLTISSLQAEDVAVYFCQQYYSI

PNTFGQGTKLEIKR;

TRL1245 heavy chain variable region has the amino acid sequence:

(SEQ ID NO: 19)
QVQLVESGGGLVKAGGSLRLSCVASGFTFSDYYMSWIRQAPGKGLEWISF

ISSSGDTIFYADSVKGRFTVSRDSAKNSLYLQMNSLKVEDTAVYYCARKG

VSDEELLRFWGQGTLVTVSS;

TRL1245 light chain variable region has the amino acid sequence:

(SEQ ID NO: 20)
DIVLTQDPSVSVSPGQTARITCSGDALPKKYAYWYQQKSGQAPVLVIYED

TKRPSGIPERFSGSSSGTVATLTISGAQVEDEADYYCYSTDSSGNQRVFG

GGTKLTVL;

TRL1330 heavy chain variable region has the amino acid sequence:

(SEQ ID NO: 21)
QVQLVESGTEVKNPGASVKVSCTASGYKFDEYGVSWVRQSPGQGLEWMGW

ISVYNGKTNYSQNFQGRLTLTTETSTDTAYMELTSLRPDDTAVYYCATDK

NWFDPWGPGTLVTVSS;

TRL1330 light chain variable region has the amino acid sequence:

(SEQ ID NO: 22)
DIVLTQSPSASGSPGQSITISCTGTNTDYNYVSWYQHHPGKAPKVIIYDV

KKRPSGVPSRFSGSRSGNTATLTVSGLQTEDEADYYCVSYADNNHYVFGS

GTKVTVL;

TRL1335 heavy chain variable region has the amino acid sequence:

(SEQ ID NO: 23)
QVQLVESGAEVKKPGESLKISCKGSGYNFTSYWIGWVRQMPGKGLEWMGV

IYPDDSDTRYSPSFKGQVTISADKSISTAFLQWSSLKASDTAVYHCARPP

DSWGQGTLVTVSS;

TRL1335 light chain variable region has the amino acid sequence:

(SEQ ID NO: 24)
DIVMTQSPATLSVSPGERATLSCRASQSVSSNLAWYQQKPGLAPRLLIVG

ASNRATGIPARFSGSGSGTEFTLTISSLQSEDFAFYYCQQYNNWPFTFGP

GTKVDVKR;

TRL1337 heavy chain variable region has the amino acid sequence:

(SEQ ID NO: 25)
QVQLLESGPGLVKPSETPSLTCTVSGGSIRSYYWSWIRQPPGKGLEWIGY

IYYSGSTNYNPSLKSRVTISVDMSKNQFSLKLSSVTAADTAMYYCARVYG

GSGSYDFDYWGQGTLVTVSS;

TRL1337 light chain variable region has the amino acid sequence:

(SEQ ID NO: 26)
DIVLTQSPSASGSPGQSVTISCTGTSSDVGGYNYVSWYQQLPGKAPKLMI

YEVTKRPSGVPDRFSGSKSGNTASLTVSGLQAEDEADYYCSSFAGSNNHV

VFGGGTKLTVL;

TRL1338 heavy chain variable region has the amino acid sequence:

(SEQ ID NO: 27)
QVQLTLRESGPTLVKPTQTLTLTCTFSGFSLSTNGVGVGWIRQPPGKALE
WLAIIYWDDDKRYSPSLKSRLTITKDTSKNQVVLTLTNMDPVDTGTYYCA
HILGASNYWTGYLRYYFDYWGQGTLVTVST;

TRL1338 light chain variable region has the amino acid sequence:

(SEQ ID NO: 28)
DIEMTQSPSVSVSPGQTARITCSGEPLAKQYAYWYQQKSGQAPVVVIYKD
TERPSGIPERFSGSSSGTTVTLTISGVQAEDEADYHCESGDSSGTYPVFG
GGTKLTVL;

TRL1341 heavy chain variable region has the amino acid sequence:

(SEQ ID NO: 29)
QVQLQESGGGLVQPGGSLKLSCAASGFIFSGSTMEIWVRQASGKGLEWVG
RIRSKTNNYATAYAASVKGRFTISRDDSKNTAYLQMNSLKTEDTAVYYCI
SLPGGYSSGQGTLVTVSS;

TRL1341 light chain variable region has the amino acid sequence:

(SEQ ID NO: 30)
DIMLTQPPSVSVSPGQTARITCSGDALPKKYTYWYQQKSGQAPVLVIYED
SKRPSEIPERFSAFTSWTTATLTITGAQVGDEADYYCYSTDITGDIGVFG
GGTKLTVL;

TRL1347 heavy chain variable region has the amino acid sequence:

(SEQ ID NO: 31)
QVQLVQSGGGLVQPGGSLKVSCVGSGFTFSASTIHWVRQASGKGLEWVGR
IRSKANNYATVSAASLKGRFTISRDDSKNTAYLQVNSLKIEDTAIYYCTR
PTACGDRVCWHGAWGQGTQVTVSP;

TRL1347 light chain variable region has the amino acid sequence:

(SEQ ID NO: 32)
DIVLTQSPSASGTPGQRVTISCSGSRSNLGNNNVNWYQQLPGTAPKLLIF
DNNERPSGVPGRFSGSKSGTSASLAISGLRSEDEADYYCASWDDSLNGWV
FGGGTKVTVL;

and

TRL1361 heavy chain variable region has the amino acid sequence:

(SEQ ID NO: 33)
QVQLVESGGGLAQPGGSLRLSCAASGFIFNTYAMGWVRQAPGKGLEWVST
VSAPGAGTYYTDSVKGRFIISRDNSKNILYLQMNRLRVEDTAVYYCARDQ
GGPAVAGARIFDYWGQGALVTVSS;

TRL1361 light chain variable region has the amino acid sequence:

(SEQ ID NO: 34)
DIVLTQSPLSLSVTPGQPASISCKSSQSLLRSDGKTYLCWYLQKPGQPPQ
LLIYEVSNRVSGVPDRFSGSGSGTDFTLKISRVEAEDVGVYYCMQSIQLR
TFGQGTKVEIKR.

The encoding nucleotide sequences for the variable regions of the antibodies of the invention and are set forth in the sequence listing as follows:

```
TRL1068: Heavy Chain: (SEQ ID NO: 35); Light Chain: (SEQ ID NO: 36)
TRL1070: Heavy Chain: (SEQ ID NO: 37); Light Chain: (SEQ ID NO: 38)
TRL1087: Heavy Chain: (SEQ ID NO: 39); Light Chain: (SEQ ID NO: 40)
TRL1215: Heavy Chain: (SEQ ID NO: 41); Light Chain: (SEQ ID NO: 42)
TRL1216: Heavy Chain: (SEQ ID NO: 43); Light Chain: (SEQ ID NO: 44)
TRL1218: Heavy Chain: (SEQ ID NO: 45); Light Chain: (SEQ ID NO: 46)
TRL1230: Heavy Chain: (SEQ ID NO: 47); Light Chain: (SEQ ID NO: 48)
TRL1232: Heavy Chain: (SEQ ID NO: 49); Light Chain: (SEQ ID NO: 50)
TRL1242: Heavy Chain: (SEQ ID NO: 51); Light Chain: (SEQ ID NO: 52)
TRL1245: Heavy Chain: (SEQ ID NO: 53); Light Chain: (SEQ ID NO: 54)
TRL1330: Heavy Chain: (SEQ ID NO: 55); and codon optimized (SEQ ID NO: 56);
Light Chain: (SEQ ID NO: 57); and codon optimized (SEQ ID NO: 58)
TRL1335: Heavy Chain: (SEQ ID NO: 59); Light Chain: (SEQ ID NO: 60)
TRL1337: Heavy Chain: (SEQ ID NO: 61); Light Chain: (SEQ ID NO: 62)
TRL1338: Heavy Chain: (SEQ ID NO: 63); Light Chain: (SEQ ID NO: 64)
TRL1341: Heavy Chain: (SEQ ID NO: 65); Light Chain: (SEQ ID NO: 66)
```

-continued

TRL1347: Heavy Chain: (SEQ ID NO: 67); Light Chain: (SEQ ID NO: 68)

TRL1361: Heavy Chain: (SEQ ID NO: 69); Light Chain: (SEQ ID NO: 70).

Example 2

Epitope Mapping

Figure 1:
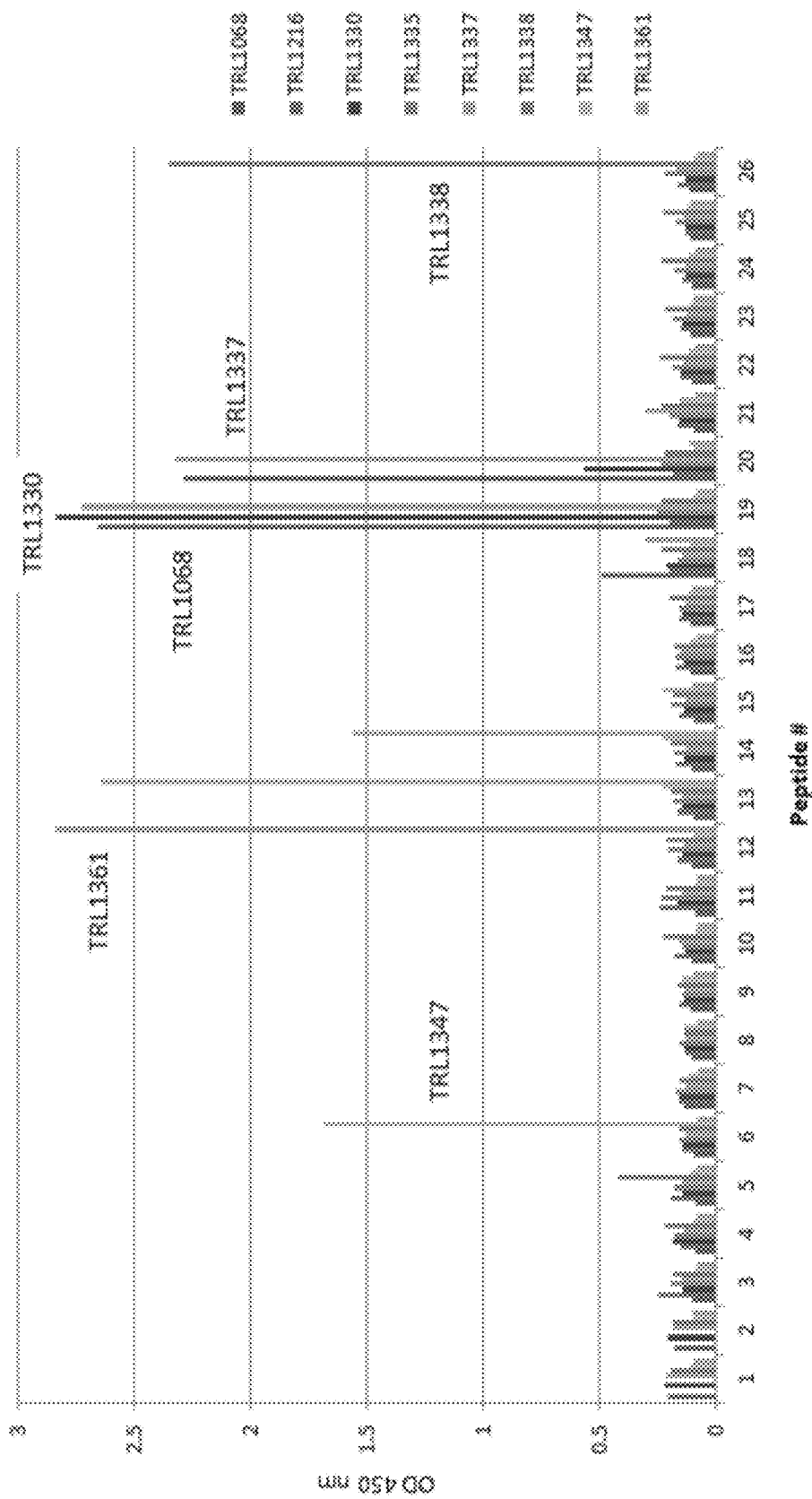
FIG. 1 shows ELISA results for various mAbs with respect to binding to a set of overlapping peptides derived from *S. aureus* DNABII protein, HU-beta, identifying multiple regions susceptible to antibody recognition.

A set of 26 overlapping 15-mer peptides (offset by 3 residues) from the HU-beta of *Staphylococcus aureus* was synthesized, each with a biotin at the N-terminus (followed by a short linker comprising SGSG). Peptides were dissolved in DMSO (15-20 mg/mL), diluted 1:1000 in PBS and bound to streptavidin coated plates in duplicate, to detect binding by the mAbs. These results are shown in FIG. 1.

TRL1068 and TRL1337 bound to peptides 19, SGSG AARKGRNPQTGKEID (SEQ ID NO:71) and 20, SGSG KGRNPQTGKEIDIPA (SEQ ID NO:72) strongly, and weakly to peptide 18, SGSG RERAARKGRNPQTGK (SEQ ID NO:73). TRL1330 bound strongly only to peptide 19. The epitope is thereby identified as within KGRNPQTGKEIDI (SEQ ID NO:74).

TRL1338 binds strongly only to peptide 26, SGSGVPAFKAGKALKDAVK (SEQ ID NO:75). TRL1361 binds at a very different site, with strong binding to peptides 12 and 13 in the set, i.e., SGSG SLAKGEKVQLIGFGN (SEQ ID NO:76) and SGSG KGEKVQLIGFGNFEV (SEQ ID NO:77), and less strongly to peptide 14, SGSG KVQLIGFGNFEVRER (SEQ ID NO:78). TRL1347 bound moderately to peptide 6, SGSG TKKEAGSAVDAVFES (SEQ ID NO:79).

TRL1335 binds to none of the 26 peptides; however, TRL1335 binds to the DNABII proteins from Pa and Sa. It is evident from these results that TRL1335 binds to a conformational epitope. TRL1338 also binds strongly to Pa and Sa. TRL1337 binds very strongly to the DNABII protein from Sa.

Figure 3:
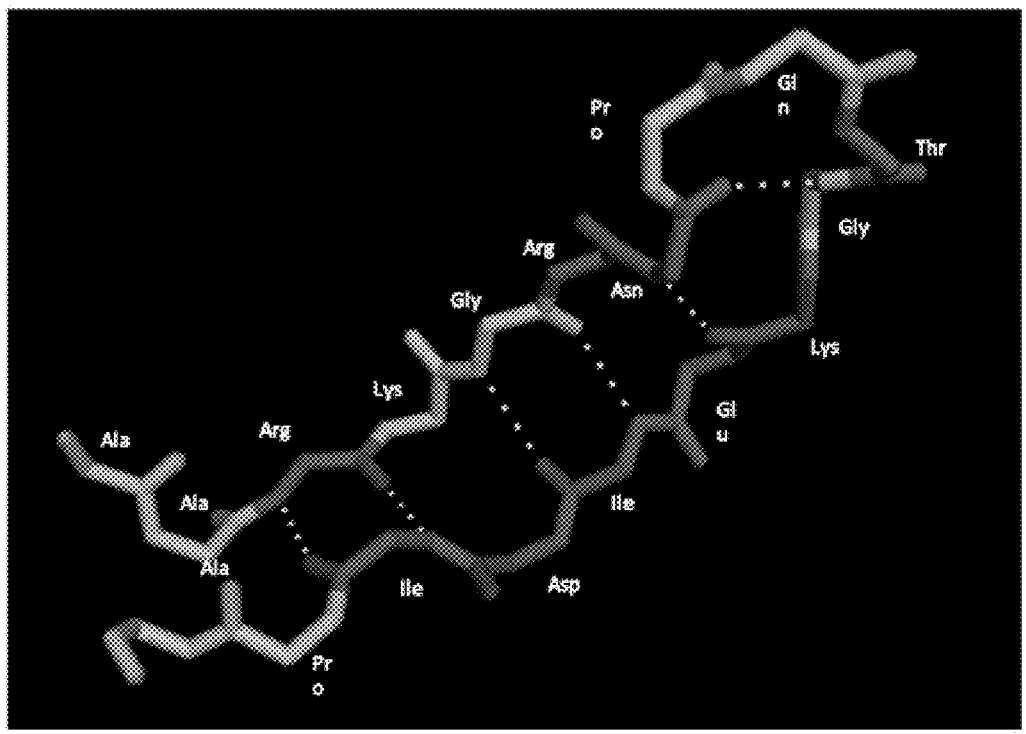
FIG. 3 shows that the key residues within the empirically defined epitope represented by SEQ ID NO:80 required for binding, as determined by alanine substitution at each residue, reside on an anti-parallel beta sheet conformationally restricted region of the protein.
Figure 3:
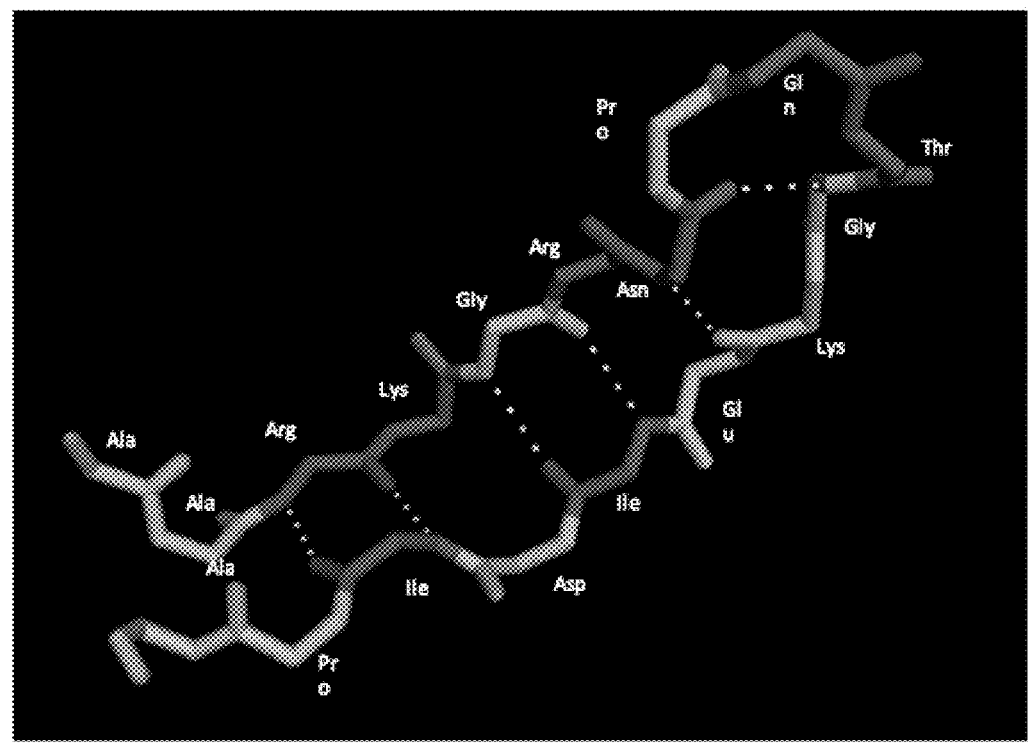

The epitope represented by SEQ ID NO:71 and SEQ ID NO:72 was then mapped more precisely using 12-mer peptides offset by one residue across the region defined by peptides 19 and 20 of the 3-residue offset set. Further, alanine scanning was conducted across this region, substituting alanine for the native amino acid at each residue in turn. As shown in FIG. 3, the epitope for both TRL1068 AARKGRNPQTGEKEIDIPA (SEQ ID NO:80) and TRL1330 AARKGRNPQTGEKEIDIPA (SEQ ID NO:80) comprises as particularly important the residues (underlined) in the linear sequence, which form a conformational epitope that is a beta-hairpin (anti-parallel beta sheet) structure. This structure has been extensively studied and peptidomimetics for such structures have been prepared. Such beta-hairpin structures can be synthesized chemically in high yields and can be cyclized to stabilize the conformation and to improve proteolytic stability. The definition of the epitopes for TRL1068 and TRL1330 at high resolution thereby enables design of peptidomimetics suitable for use as immunogens and as competing binding agents. These mAbs further provide a useful way to measure likely utility of variants of the beta hairpin structure. Only those variants that retain high affinity binding to at least one of these reference mAbs are likely to be able to induce an immune response that provides the biofilm interfering activity of the reference mAbs.

As illustrated in FIG. 2, the region of the IHF or HU protein that corresponds to SEQ ID NO:80 is substantially conserved across multiple clinically important bacterial species. Structural modeling of IHF or HU from multiple species has confirmed that the homology is high, particularly in the DNA binding region (Swinger, K. K., et al., *Current Opinion in Structural Biology* (2004) 14:28-35). Peptides that only partially overlap with this optimal region are less likely to fold spontaneously into the relevant three dimensional conformation and will be more difficult to chemically crosslink in order to lock in that conformation. Optimizing the fidelity to the native protein in this manner is advantageous for both mAb discovery and for use of the peptide as an immunogen.

Computational construction of IHF from *E. coli* shows that this epitope is partially masked by DNA when bound. However, if exposed, these portions of the proteins may generate antibodies of high affinity capable of binding them and thus preventing the formation of biofilm or causing an established biofilm to lose structural integrity as the DNABII protein is sequestered by the antibody. Other sites on the DNABII protein not involved in binding DNA may also suffice to achieve extraction of the protein out of the biofilm based on higher affinity binding by the mAb as compared to the protein's affinity for components of the biofilm.

Example 3

Determination of Affinity

For practice of the assay method, ~1 mg of DNABII protein was required. DNABII protein is difficult to express in bacteria (since it has a dual function involving gene regulation, apparently leading to toxicity to bacteria when expressed at high levels). Obtaining sufficient material for mAb discovery from bacterial sources is thus difficult. The protein was therefore expressed in HEK293 (mammalian) cells, with a poly-histidine tag to enable easy purification. The homologs from *Staphylococcus aureus* (Sa), *Pseudomonas aeruginosa* (Pa), *Klebsiella pneumoniae* (Kp), *Acinetobacter baumannii* (Ab) and *Haemophilus influenzae* (Hi) were all prepared in this manner. These five are of particular utility since they span a substantial portion of the diversity in sequences of the DNABII family.

Antibodies TRL1068, 1330, 1333, 1337 and 1338 among them bind to these proteins. Four of these, Sa, Kp, Ab, and Pa are members of the clinically problematic ESKAPE set, which are *Enterobacter aerogenes, Staphylococcus aureus, Klebsiella pneumoniae, Acinetobacter baumannii, Pseudomonas aeruginosa* and *Escherichia coli.*

The ELISA assays were conducted as follows:

Plates were coated with 1 ug/ml of antigen in PBS overnight at 4° C.

Washed 4 times in PBS/0.05% Tween® 20.

Blocked in 3% BSA/PBS and stored until ready to use.

Washed 4 times in PBS/0.05% Tween® 20.

Incubated for 1 hr with serial dilutions of anti-DNABII mAb in blocking buffer.

Washed 4 times in PBS/0.05% Tween® 20.

Incubated for 1 hr in 1 ug/ml of HRP-conjugated goat anti human IgG Fc in blocking buffer.

Washed 4 times in PBS/0.05% Tween® 20.

Developed in TMB peroxidase substrate and color stopped with stop solution with affinity estimated as the half-maximal binding concentration.

Figure 4:
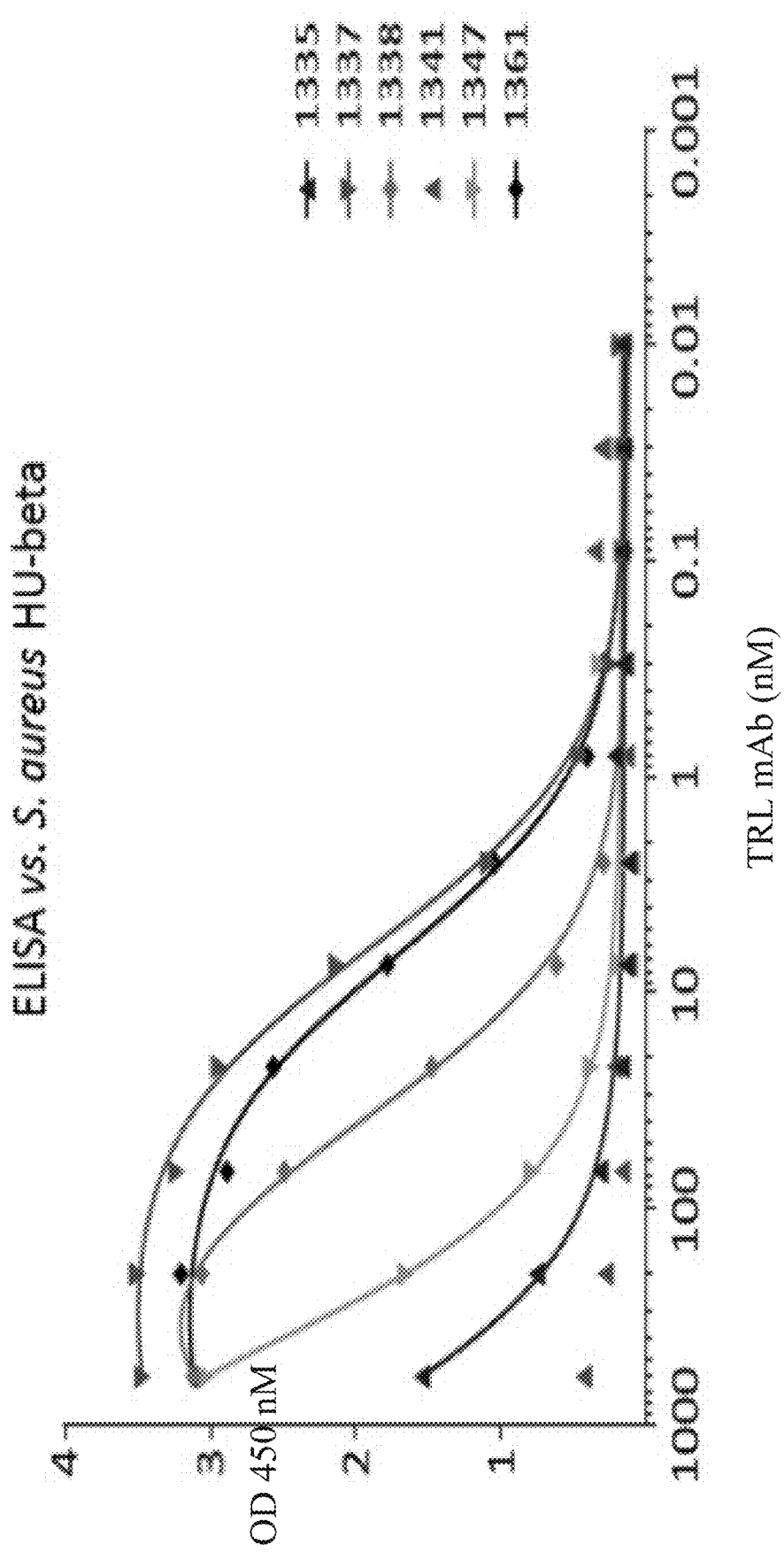
FIG. 4 shows binding for various mAbs to the full length DNABII protein, HU-beta, from *S. aureus*.

The fitted curves from the ELISA points give a mid-point value that represents an estimate of the affinity constant. The results for antibodies TRL's 1335, 1337, 1338, 1341, 1347 and 1361 in binding to HU-beta of *S. aureus* are shown in FIG. 4 and are summarized as follows.

| TRL | affinity to HU Sa |
|---|---|
| 1335 | >1 μM |
| 1337 | 6 nM |
| 1338 | 42 nM |
| 1341 | >1 μm |
| 1347 | >500 nM |
| 1361 | 6.6 nM |

Figure 5A:
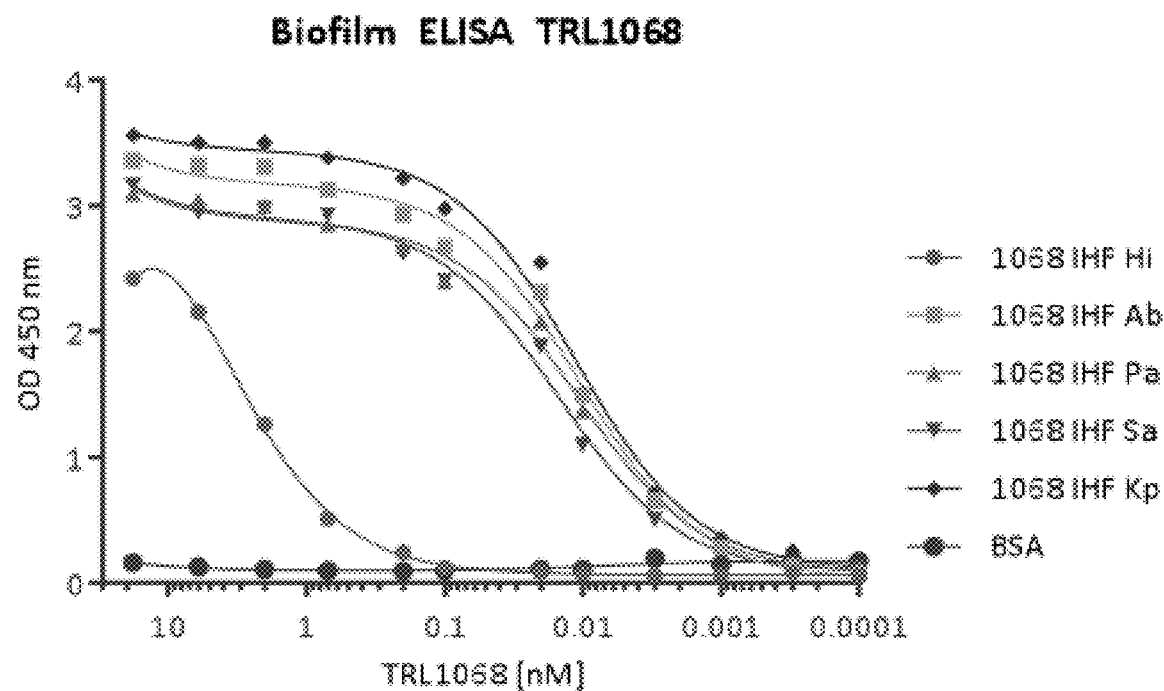
FIGS. 5A and 5B show the results of ELISA assays to determine affinity of TRL1068 and TRL1330 for biofilm forming proteins derived from different bacterial strains.
Figure 5B:
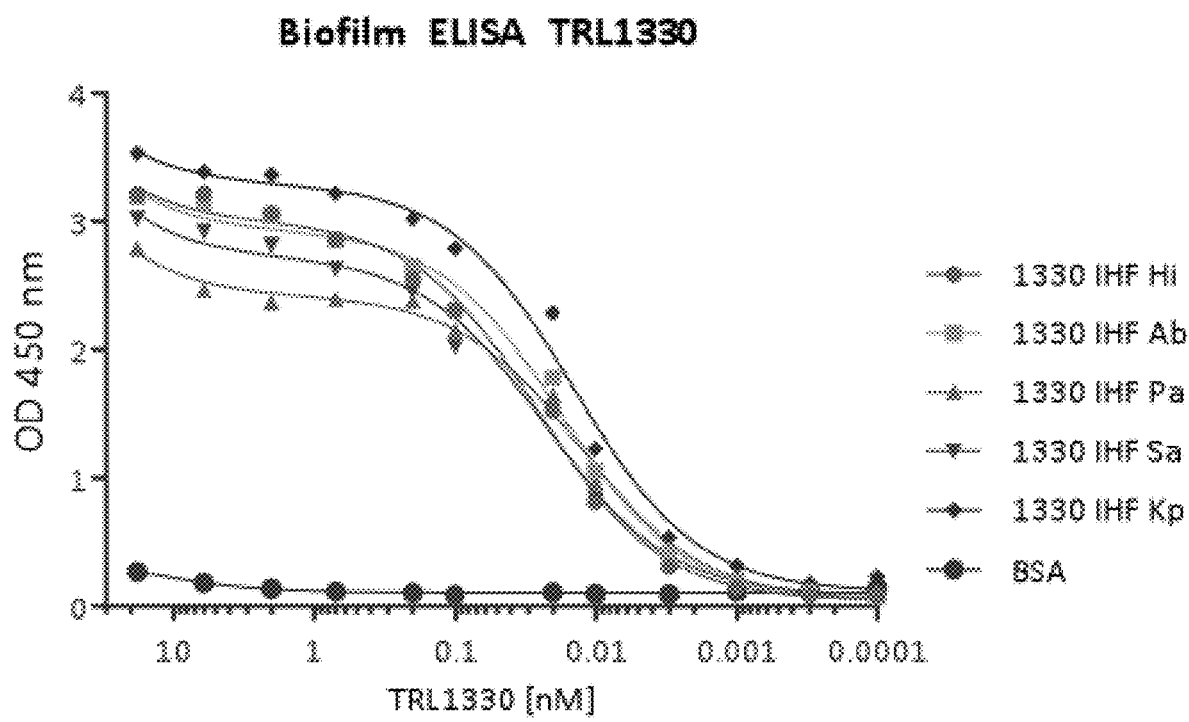

The results for TRL1068 and 1330 are shown in FIGS. 5A-5B and are as follows:

| Antigen | TRL1068 Affinity (pM) | TRL1330 Affinity (pM) |
|---|---|---|
| *P. aeruginosa* | 11 | 13 |
| *S. aureus* | 15 | 23 |
| *K. pneumoniae* | 11 | 14 |
| *H. influenzae* | 5,000 | 26 |
| *Acinetobacter baumannii* | 10 | 17 |

Although TRL1337 bound the same peptides used for epitope mapping in Example 2 as did TRL1068 and TRL1330, among the five full-length DNABII proteins tested, TRL1337 bound only that of *S. aureus*. This result is further evidence for some conformational character to the epitopes.

Example 4

In Vitro Bioactivity Assessment

Figure 6A:
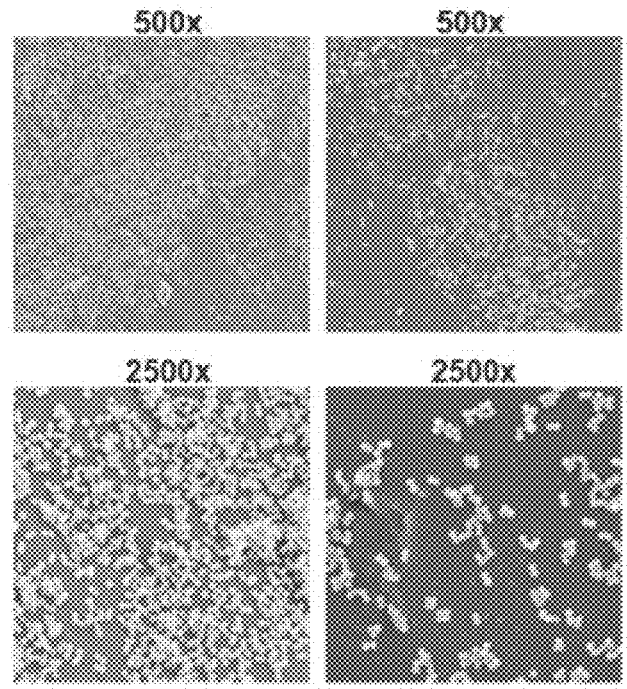
FIG. 6A shows *Staphylococcus aureus* (Sa) biofilm treated for 12 hours with a no antibody control (growth control) or with TRL1068 at 1.2 µg/mL (~7 nM), a native human mAb against a conserved epitope on DNABII proteins. TRL1068 caused dissolution of the biofilm, as evident at both low (500×) and high (2500×) magnification (scanning electron microscope images).
Figure 6B:
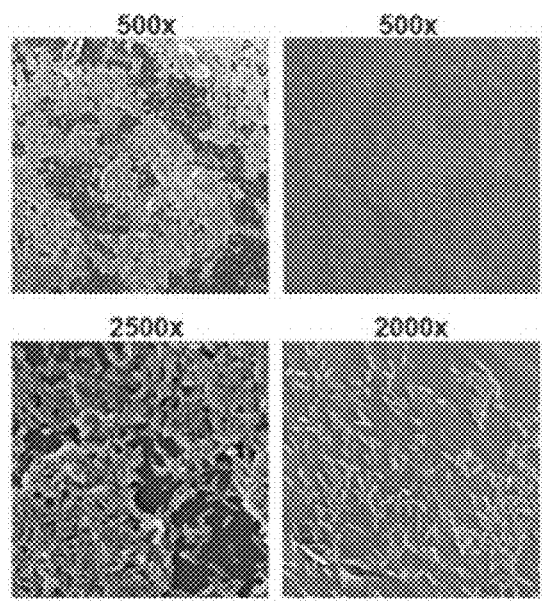
FIG. 6B shows the parallel experiment on *Pseudomonas aeruginosa* (Pa) biofilm.

TRL1068 was tested for bioactivity using a commercial assay from Innovotech (Edmonton, Alberta; Canada). Biofilms were formed in multiple replicates on plastic pegs in a 96-well microplate format exposed to media including *Pseudomonas aeruginosa* (ATCC 27853) or *Staphylococcus aureus* (ATCC 29213). Following biofilm formation, the pegs were treated in different wells with saline or an isotype matched non-binding antibody control or with TRL1068 at 1.2 μg/mL (~10 nM) for 12 hours. As evident in the scanning electron micrographs of the treated surfaces in FIGS. 6A and 6B, TRL1068 was highly effective at dissolving the biofilm as compared to the growth controls. These results establish that the mAb can degrade the biofilm, thereby removing the attached bacteria. It further shows that TRL1068 is active against biofilms produced by both gram-positive and gram-negative bacteria. Such broad spectrum activity is rarely achieved by conventional antibiotics.

TRL1330 and TRL1361 were subjected to similar assays and provided similar results. TRL1330 was active against both *Pseudomonas aeruginosa* and *Staphylococcus aureus* and TRL1361 only against *Staphylococcus aureus*.

Example 5 pH Dependence

Figure 7A:
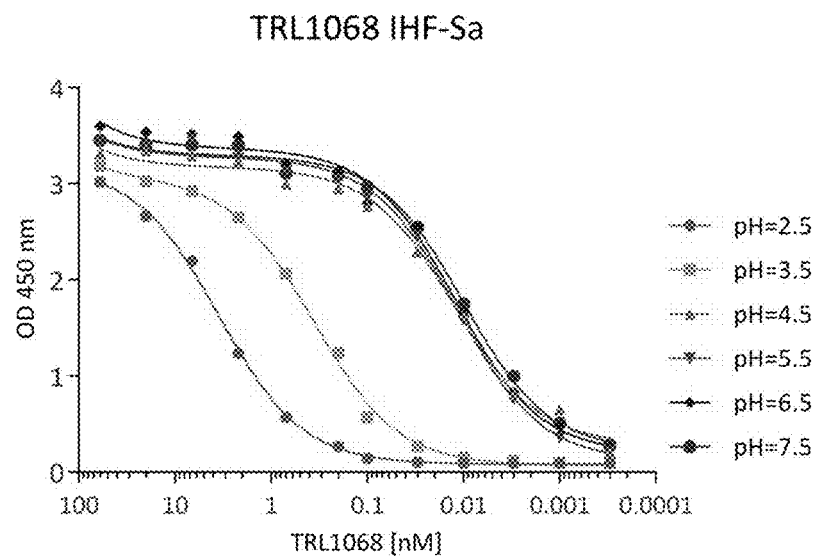
FIGS. 7A-7C show the results of ELISA assays to determine affinity of TRL1068 as a function of pH for binding to HU-beta from *Staphylococcus aureus* and IHF-alpha from *Pseudomonas aeruginosa* and *Klebsiella pneumoniae* respectively. As shown, the binding activity is consistent in the range of pH 4.5-pH 7.5 but drops off as the pH is lowered to 3.5 or 2.5.
Figure 7B:
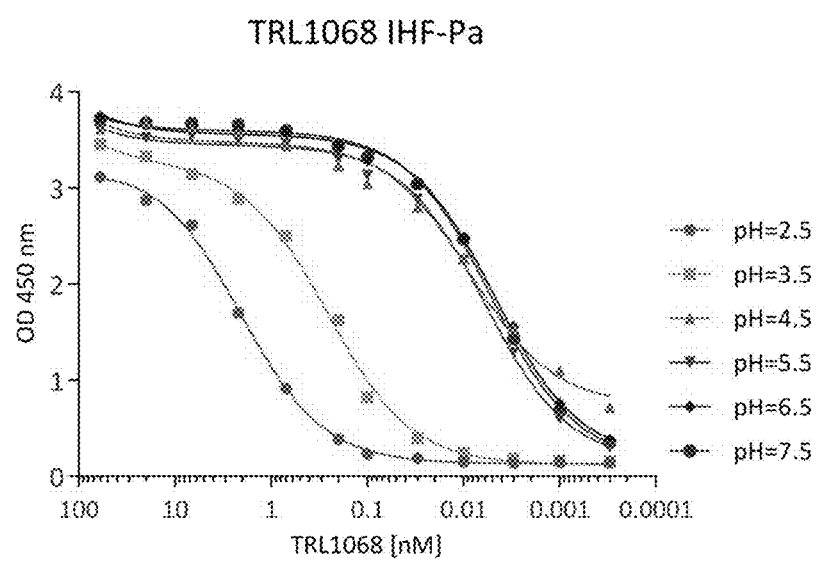
Figure 7C:
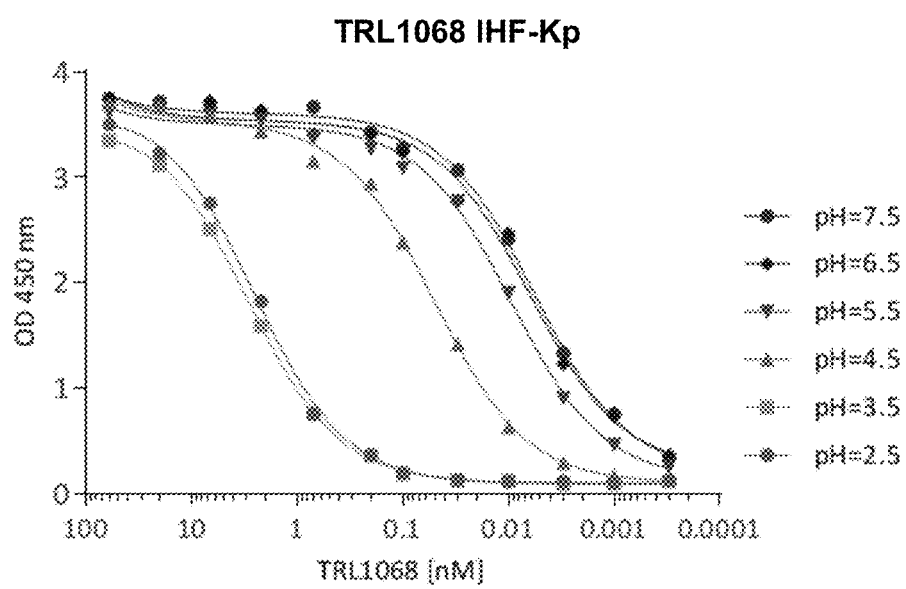

The high affinity binding of TRL1068 was shown to be retained even as the pH was decreased from physiological (pH 7.5) to pH 4.5, as shown below. FIGS. 7A-7C show the results for TRL1068 assessed against three different DNABII homologs. In other studies, no significant change in binding was seen at higher pH up to 8.5.

| | TRL1068 Affinity (nM) | | |
|---|---|---|---|
| pH | Sa | Kp | Pa |
| 7.5 | 0.010 | 0.006 | 0.005 |
| 6.5 | 0.012 | 0.006 | 0.005 |
| 5.5 | 0.012 | 0.009 | 0.006 |
| 4.5 | 0.012 | 0.050 | 0.009 |
| 3.5 | 0.36 | 3.0 | 0.26 |
| 2.5 | 3.5 | 2.6 | 2.1 |

Similarly, TRL1330 subjected to similar assays provides similar results.

This is important since the local micro-environment of infected tissues is often at lower pH than in healthy tissues.

Example 6

In Vivo Bioactivity Assessments

Figure 8A:
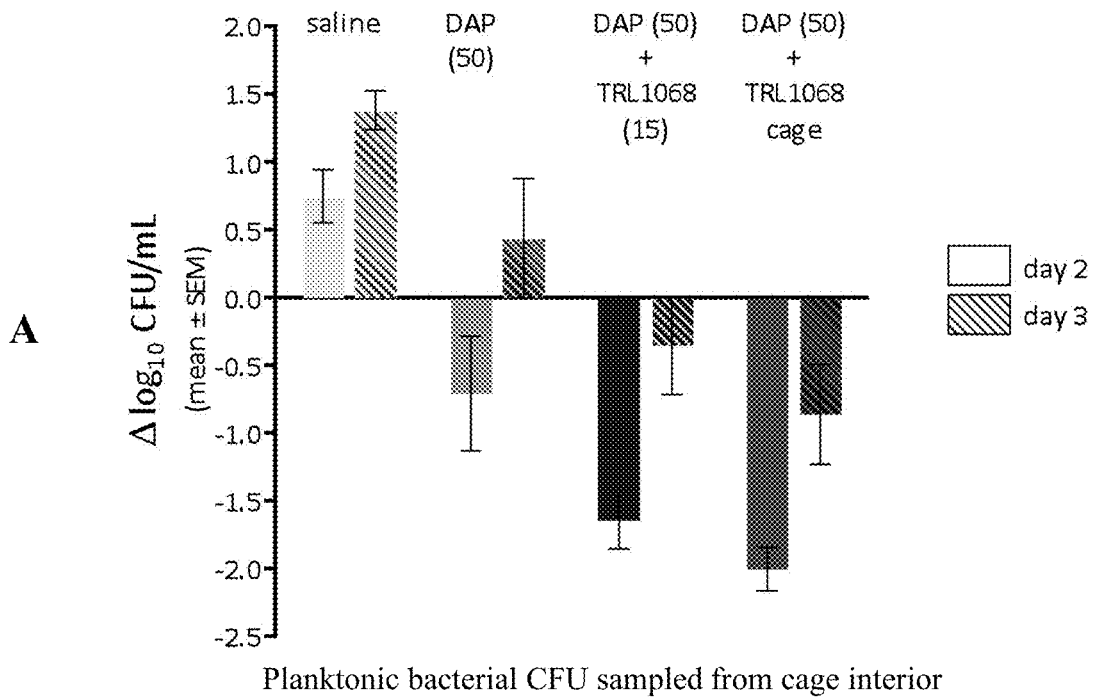
FIG. 8A shows the reduction in planktonic bacteria (released from the biofilm) and FIG. 8B shows the reduction in adherent bacteria (still retained in the biofilm) following post-infection treatment with TRL1068 in a murine model for established infection on a plastic implant. The mAb treatment combined with a standard antibiotic, daptomycin (DAP) is compared to treatment with DAP alone. Marked reduction in bacterial counts for the combination therapy is evident. TRL1068 was administered systemically at 15 mg/kg or by direct injection into the lumen of the implanted plastic perforated cage. Similar intra-cage antibody concentration was achieved for both routes of administration.
Figure 8B:
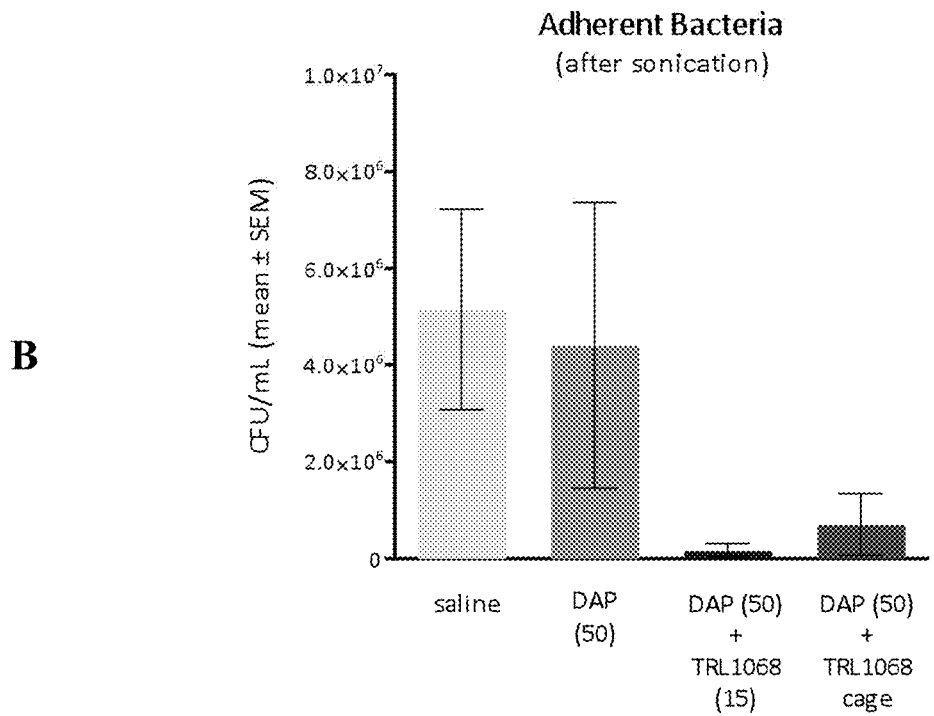

Several animal models exist for evaluation of activity. For example, as described by investigators at University Hospital Basel (Switzerland), a model for biofilm on implanted prostheses involves implanting Teflon® tissue cages (Angst+Pfister; Zurich, Switzerland) subcutaneously in BALB/c mice. Sterile perforated cylindrical Teflon® tissue cages, 8.5×1×30 mm, 1.9 mL volume (Angst+Pfister AG, Zurich, Switzerland), were implanted subcutaneously into anesthetized mice. Upon complete wound healing (two weeks), the mice were anesthetized and the cages tested for sterility by plating percutaneously aspirated tissue cage fluid (TCF) on Columbia sheep blood agar plates. To simulate a perioperative infection, 700 colony-forming units (CFU) of MRSA (ATCC 43300) were injected into each cage (day 0). After 24 hours, the interior of the cage becomes coated with a biofilm. Treatment groups (given intraperitoneally (i.p.) starting 24 hours after the biofilm was formed): saline control, antibiotic alone (daptomycin (DAP), 50 mg/kg), or antibiotic in combination with TRL1068 (15 mg/kg). On days 2 and 3, the fluid within the tissue cage (TCF) was aspirated and plated to determine CFU of planktonic bacteria. At the end of the experiment, the animals were sacrificed and the implanted cage recovered. Following sonication to release the adherent bacteria, the level of infection was again assessed as CFU per cage. As expected, the bacteria in the cage were only partially reduced by daptomycin alone. By contrast, TRL1068 in combination with daptomycin significantly reduced the bacteria inside the cages on day 2 (P<0.01). Additionally, TRL1068 in combination with daptomycin significantly reduced adherent bacteria inside the cage (P<0.02). See FIG. 8. Since daptomycin concentration in the body decreases substantially over 24 hours, a second experiment was conducted in which TRL1068 and daptomycin were administered by i.p. injection daily for 3 days. Similar efficacy at day 2 was observed, measuring the planktonic bacteria in the cage fluid. At sacrifice, the remaining adherent bacteria level was again measured. A 2 log reduction was observed for the TRL1068 treated animals, an improvement over the 1 log reduction seen with only 1 dose of daptomycin. This result is consistent with continuous erosion of the biofilm, releasing bacteria that can be killed by daptomycin more effectively than when they are embedded in the biofilm. Longer exposure to the antibody (over 5 days) was even more effective. Finally, including a pre-infection dose of TRL1068 in the regimen (including DAP+TRL1068 over 5 days) was highly effective at eliminating the biofilm. These results are described in: Estelles, A., et al., *Antimicrobial Agents Chemother*. (2016) 60(4):2292-2301.

A second example is a model that involves inducing biofilm on heart valves, mimicking native valve endocarditis (Tattevin, P., et al., *Antimicrob Agents Chemother* (2013) 57:1157). New Zealand white rabbits are anesthetized. The right carotid artery is cut and a polyethylene catheter is positioned across the aortic valve and secured in place. Twenty four hours later, 1 mL of saline plus $8 \times 10^7$ CFU of *S. aureus* is injected through the catheter, which induces a biofilm infection in 95% of the animals. Drugs (anti-biofilm and antibiotic) are administered i.v. and efficacy is evaluated after 4 days by tissue pathology and blood bacterial levels.

A third example is a rat model for valve infective endocarditis (IE). TRL1068 was evaluated in a catheter-induced aortic valve IE rat model (Xiong, Y. Q., et al., *Antimicrob Agents Chemother*. (2005) 49:3114-3121. Rats were infected with a clinical isolate (MRSA strain 300-169; associated with persistent bacteremia). Animals were treated with 6 days of vancomycin (n=8; VAN: 120 mg/kg, SC, bid) alone or in combination with TRL1068 (n=10) or isotype control antibody (n=8); each at 15 mg/kg, i.v., QD on days 1 and 4. MRSA burden in cardiac vegetations, intracardiac catheter, kidney, spleen and liver was quantified at sacrifice on day 7 (mean $\log_{10}$ CFU/g tissue ±SD). MRSA densities in vegetations showed ≥1.75 log reduction in the TRL1068+VAN arm vs. isotype control+VAN arm (P<0.001). Significant reduction in CFU's was also observed for intracardiac catheters, kidneys, spleens and livers (P<0.05) for the VAN+TRL1068 arm vs. both VAN+isotype and isotype alone arms. A trend towards mortality reduction in the VAN+TRL1068 arm was also observed (P=0.09). Similarly, TRL1330 is subjected to these assays to provide similar results.

Embodiments of the Invention

The various embodiments of the invention include a monoclonal binding moiety that has affinity for at least one DNABII protein that exceeds the affinity of said DNABII protein for components of a biofilm that includes said DNABII protein, and includes embodiments wherein the binding moiety is a monoclonal antibody (mAb), an aptamer, a non-Ig scaffold or a structured short peptide, and those wherein said binding moiety binds an epitope on said DNABII protein that is conserved across bacterial species, and combinations of these features.

This embodiment includes those embodiments wherein binding moiety is an mAb and the mAb is an Fv antibody, a bispecific antibody, a chimeric antibody, species-ized antibody or a complete antibody comprising generic constant regions heterologous to variable regions, and those wherein the biofilm component is branched DNA, and/or wherein the DNABII protein is IHF or a subunit thereof, or is HU protein or a subunit thereof, and those wherein said binding moiety dissolves biofilm derived from at least two bacterial species including both Gram positive and Gram negative species, including those wherein said species are *S. aureus, P. aeruginosa, A. baumannii* and *K. pneumoniae*, and those wherein the binding moiety has affinity for biofilm-forming protein from at least three bacterial species at least as strong as 100 pM, including those wherein species are selected from *S. aureus, P. aeruginosa, A. baumannii* and *K. pneumoniae*, and wherein said affinity is at least as strong as 40 pM, and wherein said species are *S. aureus, P. aeruginosa, A. baumannii* and *K. pneumoniae*.

Any of these embodiments may be mAbs which are humanized mAbs or modified to be compatible with a feline, canine, equine, bovine, porcine, caprine or ovine species or wherein the variable and constant regions of said mAbs are human, feline, canine, equine, bovine, porcine, caprine or ovine.

Specific embodiments of the invention include binding moieties which are mAb or antigen binding fragments wherein the variable region comprises (a) the CDR regions of the heavy chain of TRL1068 (SEQ ID NO:1); or (b) the CDR regions of the heavy chain of TRL1070 (SEQ ID NO:3); or (c) the CDR regions of the heavy chain of TRL1087 (SEQ ID NO:5); or (d) the CDR regions of the heavy chain of TRL1215 (SEQ ID NO:7); or (e) the CDR regions of the heavy chain of TRL1216 (SEQ ID NO:9); or (f) the CDR regions of the heavy chain of TRL1218 (SEQ ID NO:11); or (g) the CDR regions of the heavy chain of TRL1230 (SEQ ID NO:13); or (h) the CDR regions of the heavy chain of TRL1232 (SEQ ID NO:15); or (i) the CDR regions of the heavy chain of TRL1242 (SEQ ID NO:17); or (j) the CDR regions of the heavy chain of TRL1245 (SEQ ID NO:19); or (k) the CDR regions of the heavy chain of TRL1330 (SEQ ID NO:21); or (l) the CDR regions of the heavy chain of TRL1335 (SEQ ID NO:23); or (m) the CDR regions of the heavy chain of TRL1337 (SEQ ID NO:25); or (n) the CDR regions of the heavy chain of TRL1338 (SEQ ID NO:27); or (o) the CDR regions of the heavy chain of TRL1341 (SEQ ID NO:29); or (p) the CDR regions of the heavy chain of TRL1347 (SEQ ID NO:31); or (q) the CDR regions of the heavy chain of TRL1361 (SEQ ID NO:33), or mAb or antigen binding fragments that compete for binding DNABII protein with mAb or fragments comprising these CDR regions.

With respect to the mAb in the previous paragraph, in some embodiments the mAb of (a) further comprises the CDR regions of the light chain of TRL1068 (SEQ ID NO:2); or the mAb of (b) further comprises the CDR regions of the light chain of TRL1070 (SEQ ID NO:4); or the mAb of (c) further comprises the CDR regions of the light chain of TRL1087 (SEQ ID NO:6); or the mAb of (d) further comprises the CDR regions of the light chain of TRL1215 (SEQ ID NO:8); or the mAb of (e) further comprises the CDR regions of the light chain of TRL1216 (SEQ ID NO:10); or the mAb of (f) further comprises the CDR regions of the light chain of TRL1218 (SEQ ID NO:12); or the mAb of (g) further comprises the CDR regions of the light chain of TRL1230 (SEQ ID NO:14); or the mAb of (h) further comprises the CDR regions of the light chain of TRL1232 (SEQ ID NO:16); or the mAb of (i) further comprises the CDR regions of the light chain of TRL1242 (SEQ ID NO:18); or the mAb of (j) further comprises the CDR regions of the light chain of TRL1245 (SEQ ID NO:20); or the mAb of (k) further comprises the CDR regions of the light chain of TRL1330 (SEQ ID NO:22); or the mAb of (l) further comprises the CDR regions of the light chain of TRL1335 (SEQ ID NO:24); or the mAb of (m) further comprises the CDR regions of the light chain of TRL1337 (SEQ ID NO:26); or the mAb of (n) further comprises the CDR regions of the light chain of TRL1338 (SEQ ID NO:28); or the mAb of (o) further comprises the CDR regions of the light chain of TRL1341 (SEQ ID NO:30); or the mAb of (p) further comprises the CDR regions of the light chain of TRL1347 (SEQ ID NO:32); or the mAb of (q) further comprises the CDR regions of the light chain of TRL1361 (SEQ ID NO:34), or mAb or antigen binding fragments that compete for binding DNABII protein with mAb or fragments comprising these CDR regions.

More specific embodiments are mAbs or, antigen binding fragments thereof which comprise (a) the variable region of the heavy chain of TRL1068 (SEQ ID NO:1); or (b) the variable region of the heavy chain of TRL1070 (SEQ ID NO:3); or (c) the variable region of the heavy chain of TRL1087 (SEQ ID NO:5); or (d) the variable region of the heavy chain of TRL1215 (SEQ ID NO:7); or (e) the variable region of the heavy chain of TRL1216 (SEQ ID NO:9); or (f) the variable region of the heavy chain of TRL1218 (SEQ ID NO:11); or (g) the variable region of the heavy chain of TRL1230 (SEQ ID NO:13); or (h) the variable region of the heavy chain of TRL1232 (SEQ ID NO:15); or (i) the variable region of the heavy chain of TRL1242 (SEQ ID NO:17); or (j) the variable region of the heavy chain of TRL1245 (SEQ ID NO:19); or (k) the variable region of the heavy chain of TRL1330 (SEQ ID NO:21); or (l) the variable region of the heavy chain of TRL1335 (SEQ ID NO:23); or (m) the variable region of the heavy chain of TRL1337 (SEQ ID NO:25); or (n) the variable region of the heavy chain of TRL1338 (SEQ ID NO:27); or (o) the variable region of the heavy chain of TRL1341 (SEQ ID NO:29); or (p) the variable region of the heavy chain of TRL1347 (SEQ ID NO:31); or (q) the variable region of the heavy chain of TRL1361 (SEQ ID NO:33), or mAb or antigen binding fragments that compete for binding DNABII protein with mAb or fragments comprising these variable regions; and in particular wherein the mAb of (a) further comprises the variable region of the light chain of TRL1068 (SEQ ID NO:2); or the mAb of (b) further comprises the variable region of the light chain of TRL1070 (SEQ ID NO:4); or the mAb of (c) further comprises the variable region of the light chain of TRL1087 (SEQ ID NO:6); or the mAb of (d) further comprises the variable region of the light chain of TRL1215 (SEQ ID NO:8); or the mAb of (e) further comprises the variable region of the light chain of TRL1216 (SEQ ID NO:10); or the mAb of (f) further comprises the variable region of the light chain of TRL1218 (SEQ ID NO:12); or the mAb of (g) further comprises the variable region of the light chain of TRL1230 (SEQ ID NO:14); or the mAb of (h) further comprises the variable region of the light chain of TRL1232 (SEQ ID NO:16); or the mAb of (i) further comprises the variable region of the light chain of TRL1242 (SEQ ID NO:18); or the mAb of (j) further comprises the variable region of the light chain of TRL1245 (SEQ ID NO:20); or the mAb of (k) further comprises the variable region of the light chain of TRL1330 (SEQ ID NO:22); or the mAb of (l) further comprises the variable region of the light chain of TRL1335 (SEQ ID NO:24); or the mAb of (m) further comprises the variable region of the light chain of TRL1337 (SEQ ID NO:26); or the mAb of (n) further comprises the variable region of the light chain of TRL1338 (SEQ ID NO:28); or the mAb of (o) further comprises the variable region of the light chain of TRL1341 (SEQ ID NO:30); or the mAb of (p) further comprises the variable region of the light chain of TRL1347 (SEQ ID NO:32); or the mAb of (q) further comprises the variable region of the light chain of TRL1361 (SEQ ID NO:34), or mAb or antigen binding fragments that compete for binding DNABII protein with mAb or fragments comprising these variable regions.

Each binding moiety, including the mAbs of the invention, binds to an epitope that is conserved with respect to a DNABII protein derived from at least two or three or more species of bacteria. The epitope may be linear or conformational, and conservation of the epitope is determined simply by the ability of the binding moiety to successfully bind the relevant portion of the DNABII protein. Even for conformational epitopes, the portion may constitute a limited region of the protein, and it is thus possible to identify conservation of the epitope by review of the sequences of these proteins and selecting regions of homology.

The invention also includes pharmaceutical or veterinary compositions for treatment in a subject of a condition in said subject characterized by formation of biofilms which comprises as active ingredient the monoclonal binding moiety as set forth in any of the foregoing embodiments in an amount effective to prevent or inhibit or dissolve a biofilm characteristic of said condition, said composition further including a suitable pharmaceutical excipient, including those pharmaceutical or veterinary compositions which further include at least one antibiotic, and/or further include at least one additional active ingredient.

The invention also includes a method to treat a condition in a subject characterized by the formation of a biofilm in said subject or to detect the formation of a biofilm in said subject, which method comprises treating said subject with a binding moiety which is a monoclonal antibody (mAb), an aptamer, a non-Ig scaffold or a structured short peptide, or wherein said binding moiety has affinity for at least one DNABII protein that exceeds the affinity of said DNABII protein for components of a biofilm that includes said DNABII protein;

wherein said binding moiety binds an epitope on said DNABII protein that is conserved across bacterial species; and wherein when the biofilm is to be detected, the method further comprises observing complexation of said binding moiety with any biofilm present, such as by employing a labeled binding moiety such as a radioisotope, a dye, a fluorescent moiety or an enzyme substrate.

Such conditions may be heart valve endocarditis, chronic non-healing wounds, including venous ulcers and diabetic foot ulcers, ear infections, sinus infections, urinary tract infections, pulmonary infections, cystic fibrosis, chronic obstructive pulmonary disease, catheter-associated infections, infections associated with implanted prostheses, periodontal disease, and Lyme disease.

In particular embodiments of these methods, the subject is human and the binding moiety is an mAb which is a human or humanized mAb; in particular wherein said binding moiety dissolves biofilm derived from at least three bacterial species. Such species may be selected from *S. aureus, P. aeruginosa, A. baumannii* and *K. pneumoniae*.

In some embodiments of these methods, the binding moiety has affinity for biofilm-forming protein from at least three bacterial species at least as strong as 100 pM, wherein, in some embodiments, said species are *S. aureus, P. aeruginosa, A. baumannii* and *K. pneumoniae*.

In other embodiments, the binding moiety has affinity for biofilm-forming protein from at least three bacterial species at least as strong as 40 pM, in particular wherein said species are *S. aureus, P. aeruginosa, A. baumannii* and *K. pneumoniae*.

Particularly useful in the methods of the invention are those wherein the binding moiety is an mAb or an antigen binding fragment thereof and wherein the variable region of said mAb comprises (a) the CDR regions of the heavy chain of TRL1068 (SEQ ID NO:1); or
(b) the CDR regions of the heavy chain of TRL1070 (SEQ ID NO:3); or
(c) the CDR regions of the heavy chain of TRL1087 (SEQ ID NO:5); or
(d) the CDR regions of the heavy chain of TRL1215 (SEQ ID NO:7); or
(e) the CDR regions of the heavy chain of TRL1216 (SEQ ID NO:9); or
(f) the CDR regions of the heavy chain of TRL1218 (SEQ ID NO:11); or
(g) the CDR regions of the heavy chain of TRL1230 (SEQ ID NO:13); or
(h) the CDR regions of the heavy chain of TRL1232 (SEQ ID NO:15); or
(i) the CDR regions of the heavy chain of TRL1242 (SEQ ID NO:17); or
(j) the CDR regions of the heavy chain of TRL1245 (SEQ ID NO:19); or
(k) the CDR regions of the heavy chain of TRL1330 (SEQ ID NO:21); or
(l) the CDR regions of the heavy chain of TRL1335 (SEQ ID NO:23); or
(m) the CDR regions of the heavy chain of TRL1337 (SEQ ID NO:25); or
(n) the CDR regions of the heavy chain of TRL1338 (SEQ ID NO:27); or
(o) the CDR regions of the heavy chain of TRL1341 (SEQ ID NO:29); or
(p) the CDR regions of the heavy chain of TRL1347 (SEQ ID NO:31); or
(q) the CDR regions of the heavy chain of TRL1361 (SEQ ID NO:33), or mAb or antigen binding fragments that compete for binding DNABII protein with mAb or fragments comprising these CDR regions; and including said mAb or fragment and in particular wherein the mAb of (a) further comprises the CDR regions of the light chain of TRL1068 (SEQ ID NO:2); or
the mAb of (b) further comprises the CDR regions of the light chain of TRL1070 (SEQ ID NO:4); or
the mAb of (c) further comprises the CDR regions of the light chain of TRL1087 (SEQ ID NO:6); or
the mAb of (d) further comprises the CDR regions of the light chain of TRL1215 (SEQ ID NO:8); or
the mAb of (e) further comprises the CDR regions of the light chain of TRL1216 (SEQ ID NO:10); or
the mAb of (f) further comprises the CDR regions of the light chain of TRL1218 (SEQ ID NO:12); or
the mAb of (g) further comprises the CDR regions of the light chain of TRL1230 (SEQ ID NO:14); or
the mAb of (h) further comprises the CDR regions of the light chain of TRL1232 (SEQ ID NO:16); or
the mAb of (i) further comprises the CDR regions of the light chain of TRL1242 (SEQ ID NO:18); or
the mAb of (j) further comprises the CDR regions of the light chain of TRL1245 (SEQ ID NO:20); or
the mAb of (k) further comprises the CDR regions of the light chain of TRL1330 (SEQ ID NO:22); or
the mAb of (l) further comprises the CDR regions of the light chain of TRL1335 (SEQ ID NO:24); or
the mAb of (m) further comprises the CDR regions of the light chain of TRL1337 (SEQ ID NO:26); or
the mAb of (n) further comprises the CDR regions of the light chain of TRL1338 (SEQ ID NO:28); or
the mAb of (o) further comprises the CDR regions of the light chain of TRL1341 (SEQ ID NO:30); or
the mAb of (p) further comprises the CDR regions of the light chain of TRL1347 (SEQ ID NO:32); or
the mAb of (q) further comprises the CDR regions of the light chain of TRL1361 (SEQ ID NO:34), or mAb or antigen binding fragments that compete for binding DNABII protein with mAb or fragments comprising these CDR regions.

In more specific embodiments of the invention methods, the subject is human and said mAb or antigen-binding fragment comprises (a) the variable region of the heavy chain of TRL1068 (SEQ ID NO:1); or
(b) the variable region of the heavy chain of TRL1070 (SEQ ID NO:3); or
(c) the variable region of the heavy chain of TRL1087 (SEQ ID NO:5); or
(d) the variable region of the heavy chain of TRL1215 (SEQ ID NO:7); or
(e) the variable region of the heavy chain of TRL1216 (SEQ ID NO:9); or
(f) the variable region of the heavy chain of TRL1218 (SEQ ID NO:11); or
(g) the variable region of the heavy chain of TRL1230 (SEQ ID NO:13); or
(h) the variable region of the heavy chain of TRL1232 (SEQ ID NO:15); or
(i) the variable region of the heavy chain of TRL1242 (SEQ ID NO:17); or
(j) the variable region of the heavy chain of TRL1245 (SEQ ID NO:19); or
(k) the variable region of the heavy chain of TRL1330 (SEQ ID NO:21); or
(l) the variable region of the heavy chain of TRL1335 (SEQ ID NO:23); or
(m) the variable region of the heavy chain of TRL1337 (SEQ ID NO:25); or
(n) the variable region of the heavy chain of TRL1338 (SEQ ID NO:27); or (o) the variable region of the heavy chain of TRL1341 (SEQ ID NO:29); or (p) the variable region of the heavy chain of TRL1347 (SEQ ID NO:31); or (q) the variable region of the heavy chain of TRL1361 (SEQ ID NO:33), or mAb or antigen binding fragments that compete for binding DNABII protein with mAb or fragments comprising these variable regions; and in particular wherein the mAb of (a) further comprises the variable region of the light chain of TRL1068 (SEQ ID NO:2); or the mAb of (b) further comprises the variable region of the light chain of TRL1070 (SEQ ID NO:4); or the mAb of (c) further comprises the variable region of the light chain of TRL1087 (SEQ ID NO:6); or the mAb of (d) further comprises the variable region of the light chain of TRL1215 (SEQ ID NO:8); or the mAb of (e) further comprises the variable region of the light chain of TRL1216 (SEQ ID NO:10); or the mAb of (f) further comprises the variable region of the light chain of TRL1218 (SEQ ID NO:12); or the mAb of (g) further comprises the variable region of the light chain of TRL1230 (SEQ ID NO:14); or the mAb of (h) further comprises the variable region of the light chain of TRL1232 (SEQ ID NO:16); or the mAb of (i) further comprises the variable region of the light chain of TRL1242 (SEQ ID NO:18); or the mAb of (j) further comprises the variable region of the light chain of TRL1245 (SEQ ID NO:20); or the mAb of (k) further comprises the variable region of the light chain of TRL1330 (SEQ ID NO:22); or the mAb of (l) further comprises the variable region of the light chain of TRL1335 (SEQ ID NO:24); or the mAb of (m) further comprises the variable region of the light chain of TRL1337 (SEQ ID NO:26); or the mAb of (m) further comprises the variable region of the light chain of TRL1338 (SEQ ID NO:28); or the mAb of (o) further comprises the variable region of the light chain of TRL1341 (SEQ ID NO:30); or the mAb of (p) further comprises the variable region of the light chain of TRL1347 (SEQ ID NO:32); or the mAb of (q) further comprises the variable region of the light chain of TRL1361 (SEQ ID NO:34), or mAb or antigen binding fragments that compete for binding DNABII protein with mAb or fragments comprising these variable regions.

As shown in Example 2, mAbs have been prepared that bind to a conformational epitope comprised in SEQ ID NO:80.

In other embodiments, the invention includes recombinant expression systems for producing any of the binding moieties listed above in cases wherein said binding moiety is a protein, wherein said expression system comprises a nucleotide sequence encoding said protein operably linked to heterologous control sequences for expression, and the invention also includes recombinant host cells that have been modified to contain these expression systems and methods to prepare any of the proteinaceous binding moieties set forth above which method comprises culturing these cells.

In other embodiments, the invention includes methods to prevent formation of or to dissolve a biofilm associated with an industrial or other non-physiological process which method comprises treating a surface susceptible to or containing a biofilm with any of the binding moieties described above.

The invention further includes methods to prepare an aptamer nucleic acid or nucleic acid mimic which method comprises preparing a nucleic acid or peptide-nucleic acid consisting of 10-25 nucleotides that specifically binds a specific binding partner to any of the monoclonal binding moieties set forth above; especially when the specific binding partner is an epitope of a DNABII protein, and/or said epitope is conserved across at least three bacterial species.

The invention also includes an aptamer nucleic acid or peptide nucleic acid mimic prepared by the foregoing method.

Pharmaceutical or veterinary compositions for treatment in a subject of a condition in said subject characterized by formation of biofilms which comprises as active ingredient the above aptamer in an amount effective to prevent or inhibit or dissolve a biofilm characteristic of said condition said composition further including a suitable pharmaceutical excipient, are also included.

The invention also includes a surface in an industrial or other non-biological setting coated with any of the binding moieties described above or with the above aptamer described.

In another aspect, the invention includes a synthetic compound that mimics the epitope to which TRL1068, TRL1330 or TRL1337, especially TRL1068 or TRL1330 binds, wherein the synthetic compound mimics the conformational epitope contained in SEQ ID NO:80. In some embodiments, the epitope comprises the sequence RNPQT (positions 6-10 of SEQ ID NO:80) from the HU-beta of S. aureus to which TRL1068 binds or that comprises the sequence KGRNPQTGKEI (positions 6-14 of SEQ ID NO:80) from IHF of S. aureus HU-beta to which TRL1330 binds. The invention further includes a method to obtain antisera effective to dissolve biofilm which method comprises immunizing a subject with this synthetic compound and recovering antiserum from said subject, as well as the polyclonal antiserum or monoclonal antibodies derived therefrom obtained from this subject.

The mimics themselves can be verified by their ability to bind to the antibodies of the invention, especially TRL1068, TRL1330, TRL1337 or TRL1361. The mimics then, in turn, may be used to identify binding moieties from libraries of nucleic acids or other molecules that are candidate binding agents, resulting in aptamers or other peptide-based or small molecule-based binding moieties.

The invention also includes a method to treat biofilm-related conditions in a subject, which method comprises administering to said subject the antiserum or these monoclonal antibodies.

The invention is also directed to a method to image a biofilm which method comprises treating the biofilm with a monoclonal antibody or antigen-binding fragment thereof that binds specifically to an epitope within positions 5-20 of SEQ ID NO:76 or positions 5-20 of SEQ ID NO:77 or of SEQ ID NO:78 or to a peptidomimetic of any of these, said antibody conjugated to an observable label, and obtaining an image based on said label, and also includes a method to measure the level of a DNABII protein which method comprises subjecting a sample in which said DNABII protein is to be detected to a sandwich assay in which one antibody or antigen-binding fragment thereof comprising said sandwich binds an epitope within positions 5-20 of SEQ ID NO:76 or positions 5-20 of SEQ ID NO:77 or positions 5-20 of SEQ ID NO:78 and the other antibody or antigen-binding fragment thereof in said sandwich binds to an epitope within positions 5-20 of any of SEQ ID NOS:71-75 and 79-80 or to a peptidomimetic of any of these.

The invention includes, specifically an mAb, which mAb is an Fv antibody, a bispecific antibody, a chimeric antibody, species-ized antibody or a complete antibody, wherein said complete antibody comprises generic constant regions heterologous to variable regions, which mAb competes with TRL1335, TRL1338, TRL1341, TRL1347 or TRL1361 for binding to a DNABII protein, in particular wherein the variable region comprises (a) the CDR regions of the heavy chain of TRL1335 (SEQ ID NO:23); or (b) the CDR regions of the heavy chain of TRL1338 (SEQ ID NO:27); or (c) the CDR regions of the heavy chain of TRL1341 (SEQ ID NO:29); or (d) the CDR regions of the heavy chain of TRL1347 (SEQ ID NO:31); or (e) the CDR regions of the heavy chain of TRL1361 (SEQ ID NO:35), or more specifically wherein the mAb of (a) further comprises the CDR regions of the light chain of TRL1335 (SEQ ID NO:24); or the mAb of (b) further comprises the CDR regions of the light chain of TRL1338 (SEQ ID NO:28); or the mAb of (c) further comprises the CDR regions of the light chain of TRL1341 (SEQ ID NO:30); or the mAb of (d) further comprises the CDR regions of the light chain of TRL1347 (SEQ ID NO:32); or the mAb of (e) further comprises the CDR regions of the light chain of TRL1361 (SEQ ID NO:34).

The invention also includes recombinant host cells that have been modified to contain a recombinant expression system wherein said expression system comprises one or more nucleotide sequences encoding one of the mAb's set forth above operably linked to one or more heterologous control sequences for expression, and in particular wherein said mAb comprises a variable region encoded by nucleic acid isolated from B cells of a human not immunized with DNABII protein or with a fragment thereof, as well as a method to prepare an mAb that binds a DNABII protein which method comprises culturing these cells.

The invention further includes a method to prevent formation of, or to dissolve a biofilm associated with, a non-physiological process which method comprises treating a surface associated with said process susceptible to, or containing a, biofilm with an effective amount of the foregoing mAbs, and a non-physiological surface coated with one or more of these mAbs.

The invention claimed is:

1. Recombinant host cells that have been modified to contain a recombinant expression system for producing an mAb or antigen binding fragment thereof wherein said expression system comprises one or more nucleotide sequences encoding at least the variable regions of said mAb operably linked to one or more heterologous control sequences for expression wherein
   the variable region of said mAb comprises the heavy and light chain variable regions of i) TRL1068 (SEQ ID NO:1 and SEQ ID NO: 2) or ii) of TRL1330 (SEQ ID NO:21 and SEQ ID NO: 22) or iii) of TRL1337 (SEQ ID NO:25 and SEQ ID NO: 26).

2. The recombinant host cells of claim 1 wherein said mAb comprises the variable region of the heavy and light chain of TRL1068 (SEQ ID NO:1 and SEQ ID NO: 2).

3. A method to prepare an mAb that binds a DNABII protein which method comprises culturing the cells of claim 1 and recovering said mAb.

4. A method to prepare an mAb that binds a DNABII protein which method comprises culturing the cells of claim 2 and recovering said mAb.

5. A recombinant expression system for producing an mAb or antigen-binding fragment thereof wherein said expression system comprises one or more nucleotide sequences encoding said at least the variable regions of said mAb operably linked to one or more heterologous control sequences for expression wherein
   the variable region of said mAb comprises the heavy and light chain variable regions of i) TRL1068 (SEQ ID NO:1 and SEQ ID NO: 2) or ii) of TRL1330 (SEQ ID NO:21 and SEQ ID NO: 22) or iii) of TRL1337 (SEQ ID NO:25 and SEQ ID NO: 26).

6. The recombinant expression system of claim 5 wherein the variable region of said mAb comprises the heavy and light chain variable regions of TRL1068 (SEQ ID NO:1 and SEQ ID NO: 2).

* * * * *

SEQUENCE LISTING

```
<160> NUMBER OF SEQ ID NOS: 91

<210> SEQ ID NO 1
<211> LENGTH: 119
<212> TYPE: PRT
<213> ORGANISM: Homo sapiens

<400> SEQUENCE: 1

Gln Val Gln Leu Val Glu Ser Gly Pro Gly Leu Val Lys Pro Ser Glu
1               5                   10                  15

Thr Leu Ser Leu Thr Cys Arg Val Ser Gly Asp Ser Asn Arg Pro Ser
            20                  25                  30

Tyr Trp Ser Trp Ile Arg Gln Ala Pro Gly Lys Ala Met Glu Trp Ile
        35                  40                  45

Gly Tyr Val Tyr Asp Ser Gly Val Thr Ile Tyr Asn Pro Ser Leu Lys
    50                  55                  60

Gly Arg Val Thr Ile Ser Leu Asp Thr Ser Lys Thr Arg Phe Ser Leu
65                  70                  75                  80

Lys Leu Thr Ser Val Ile Ala Ala Asp Thr Ala Val Tyr Tyr Cys Ala
                85                  90                  95

Arg Glu Arg Phe Asp Arg Thr Ser Tyr Lys Ser Trp Trp Gly Gln Gly
                100                 105                 110

Thr Gln Val Thr Val Ser Ser
        115

<210> SEQ ID NO 2
<211> LENGTH: 108
<212> TYPE: PRT
<213> ORGANISM: Homo sapiens

<400> SEQUENCE: 2

Asp Ile Val Leu Thr Gln Ala Pro Gly Thr Leu Ser Leu Ser Pro Gly
1               5                   10                  15

Asp Arg Ala Thr Leu Ser Cys Arg Ala Ser Gln Arg Leu Gly Gly Thr
            20                  25                  30
```

```
Ser Leu Ala Trp Tyr Gln His Arg Ser Gly Gln Ala Pro Arg Leu Ile
            35                  40                  45

Leu Tyr Gly Thr Ser Asn Arg Ala Thr Asp Thr Pro Asp Arg Phe Ser
        50                  55                  60

Gly Ser Gly Ser Gly Thr Asp Phe Val Leu Thr Ile Ser Ser Leu Glu
65                  70                  75                  80

Pro Glu Asp Phe Ala Val Tyr Tyr Cys Gln Gln Tyr Gly Ser Pro Pro
                85                  90                  95

Tyr Thr Phe Gly Gln Gly Thr Thr Leu Asp Ile Lys
                100                 105
```

<210> SEQ ID NO 3
<211> LENGTH: 122
<212> TYPE: PRT
<213> ORGANISM: Homo sapiens

<400> SEQUENCE: 3

```
Gln Val Gln Leu Val Gln Ser Gly Gly Thr Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ser Met Ser Trp Val Arg Gln Ala Pro Gly Lys Gly Leu Glu Trp Val
        35                  40                  45

Ala Asn Ile Lys His Asp Gly Thr Glu Arg Asn Tyr Val Asp Ser Val
    50                  55                  60

Lys Gly Arg Phe Thr Ile Ser Arg Asp Asn Ser Glu Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Tyr Tyr Tyr Gly Ala Gly Thr Asn Tyr Pro Leu Lys Tyr Trp
                100                 105                 110

Gly Gln Gly Thr Arg Val Thr Val Ser Ser
            115                 120
```

<210> SEQ ID NO 4
<211> LENGTH: 108
<212> TYPE: PRT
<213> ORGANISM: Homo sapiens

<400> SEQUENCE: 4

```
Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Leu
                85                  90                  95

Thr Phe Gly Gly Gly Thr Lys Val Glu Ile Lys Arg
                100                 105
```

<210> SEQ ID NO 5
<211> LENGTH: 116
<212> TYPE: PRT
<213> ORGANISM: Homo sapiens

<400> SEQUENCE: 5

Gln Val Gln Leu Leu Glu Ser Gly Pro Gly Leu Val Arg Pro Ser Asp
1               5                   10                  15

Thr Leu Ser Leu Thr Cys Thr Phe Ser Ala Asp Leu Ser Thr Asn Ala
            20                  25                  30

Tyr Trp Thr Trp Ile Arg Gln Pro Pro Gly Lys Gly Leu Glu Trp Ile
        35                  40                  45

Gly Tyr Met Ser His Ser Gly Gly Arg Asp Tyr Asn Pro Ser Phe Asn
    50                  55                  60

Arg Arg Val Thr Ile Ser Val Asp Thr Ser Lys Asn Gln Val Phe Leu
65                  70                  75                  80

Arg Leu Thr Ser Val Thr Ser Ala Asp Thr Ala Val Tyr Phe Cys Val
                85                  90                  95

Arg Glu Val Gly Ser Tyr Tyr Asp Tyr Trp Gly Gln Gly Ile Leu Val
            100                 105                 110

Thr Val Ser Ser
        115

<210> SEQ ID NO 6
<211> LENGTH: 108
<212> TYPE: PRT
<213> ORGANISM: Homo sapiens

<400> SEQUENCE: 6

Asp Ile Glu Met Thr Gln Ser Pro Ser Ser Leu Ser Ala Ser Val Gly
1               5                   10                  15

Asp Arg Ile Thr Ile Thr Cys Arg Ala Ser Gln Gly Ile Ser Thr Trp
            20                  25                  30

Leu Ala Trp Tyr Gln Gln Lys Pro Gly Lys Ala Pro Lys Ser Leu Ile
        35                  40                  45

Phe Ser Thr Ser Leu His Ser Gly Val Pro Ser Lys Phe Ser Gly
    50                  55                  60

Ser Gly Ser Gly Thr Asp Phe Thr Leu Thr Ile Thr Asn Leu Gln Pro
65                  70                  75                  80

Glu Asp Phe Ala Thr Tyr Tyr Cys Gln Gln Lys Trp Glu Thr Pro Tyr
                85                  90                  95

Ser Phe Gly Gln Gly Thr Lys Leu Asp Met Ile Arg
            100                 105

<210> SEQ ID NO 7
<211> LENGTH: 116
<212> TYPE: PRT
<213> ORGANISM: Homo sapiens

<400> SEQUENCE: 7

Gln Val Gln Leu Val Glu Ser Gly Thr Glu Val Lys Asn Pro Gly Ala
1               5                   10                  15

Ser Val Lys Val Ser Cys Thr Ala Ser Gly Tyr Lys Phe Asp Glu Tyr
            20                  25                  30

Gly Val Ser Trp Val Arg Gln Ser Pro Gly Gln Gly Leu Glu Trp Met
        35                  40                  45

Gly Trp Ile Ser Val Tyr Asn Gly Lys Thr Asn Tyr Ser Gln Asn Phe
    50                  55                  60

-continued

Gln Gly Arg Leu Thr Leu Thr Thr Glu Thr Ser Thr Asp Thr Ala Tyr
65                  70                  75                  80

Met Glu Leu Thr Ser Leu Arg Pro Asp Asp Thr Ala Val Tyr Tyr Cys
                85                  90                  95

Ala Thr Asp Lys Asn Trp Phe Asp Pro Trp Gly Pro Gly Thr Leu Val
            100                 105                 110

Thr Val Ser Ser
            115

<210> SEQ ID NO 8
<211> LENGTH: 107
<212> TYPE: PRT
<213> ORGANISM: Homo sapiens

<400> SEQUENCE: 8

Asp Ile Val Met Thr Gln Ser Pro Ser Ala Ser Gly Ser Pro Gly Gln
1               5                   10                  15

Ser Ile Thr Ile Ser Cys Thr Gly Thr Asn Thr Asp Tyr Asn Tyr Val
            20                  25                  30

Ser Trp Tyr Gln His His Pro Gly Lys Ala Pro Lys Val Ile Ile Tyr
        35                  40                  45

Asp Val Lys Lys Arg Pro Ser Gly Val Pro Ser Arg Phe Ser Gly Ser
    50                  55                  60

Arg Ser Gly Asn Thr Ala Thr Leu Thr Val Ser Gly Leu Gln Thr Glu
65                  70                  75                  80

Asp Glu Ala Asp Tyr Tyr Cys Val Ser Tyr Ala Asp Asn Asn His Tyr
                85                  90                  95

Val Phe Gly Ser Gly Thr Lys Val Thr Val Leu
            100                 105

<210> SEQ ID NO 9
<211> LENGTH: 128
<212> TYPE: PRT
<213> ORGANISM: Homo sapiens

<400> SEQUENCE: 9

Gln Val Gln Leu Val Glu Ser Gly Gly Gly Val Val Gln Pro Gly Gly
1               5                   10                  15

Ser Leu Arg Val Ser Cys Ala Ala Ser Ala Phe Ser Phe Arg Asp Tyr
            20                  25                  30

Gly Ile His Trp Val Arg Gln Ala Pro Gly Lys Gly Leu Gln Trp Val
        35                  40                  45

Ala Val Ile Ser His Asp Gly Lys Lys Phe Tyr Ala Asp Ser Val
    50                  55                  60

Arg Gly Arg Phe Thr Ile Ser Arg Asp Asn Ser Glu Asn Thr Leu Tyr
65                  70                  75                  80

Leu Gln Met Asn Ser Leu Arg Ser Asp Asp Thr Ala Val Tyr Tyr Cys
                85                  90                  95

Ala Arg Leu Val Ala Ser Cys Ser Gly Ser Thr Cys Thr Thr Gln Pro
            100                 105                 110

Ala Ala Phe Asp Ile Trp Gly Pro Gly Thr Leu Val Thr Val Ser Ser
        115                 120                 125

<210> SEQ ID NO 10
<211> LENGTH: 108
<212> TYPE: PRT
<213> ORGANISM: Homo sapiens -continued

<400> SEQUENCE: 10

Asp Ile Met Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Thr
            20                  25                  30

Tyr Trp Tyr Gln Gln Lys Ser Gly Gln Ala Pro Val Leu Leu Ile Tyr
        35                  40                  45

Glu Asp Arg Lys Arg Pro Ser Glu Ile Pro Glu Arg Phe Ser Ala Phe
    50                  55                  60

Thr Ser Trp Thr Thr Ala Thr Leu Thr Ile Thr Gly Ala Gln Val Arg
65                  70                  75                  80

Asp Glu Ala Asp Tyr Tyr Cys Tyr Ser Thr Asp Ile Ser Gly Asp Ile
                85                  90                  95

Gly Val Phe Gly Gly Gly Thr Lys Leu Thr Val Leu
            100                 105

<210> SEQ ID NO 11
<211> LENGTH: 120
<212> TYPE: PRT
<213> ORGANISM: Homo sapiens

<400> SEQUENCE: 11

Gln Val Gln Leu Leu Glu Ser Gly Ala Asp Met Val Gln Pro Gly Arg
1               5                   10                  15

Ser Leu Arg Leu Ser Cys Ala Ala Ser Gly Phe Asn Phe Arg Thr Tyr
            20                  25                  30

Ala Met His Trp Val Arg Gln Ala Pro Gly Lys Gly Leu Glu Trp Val
        35                  40                  45

Ala Val Met Ser His Asp Gly Tyr Thr Lys Tyr Tyr Ser Asp Ser Val
    50                  55                  60

Arg Gly Gln Phe Thr Ile Ser Arg Asp Asn Ser Lys Asn Thr Leu Tyr
65                  70                  75                  80

Leu Gln Met Asn Asn Leu Arg Pro Asp Asp Thr Ala Ile Tyr Tyr Cys
                85                  90                  95

Ala Arg Gly Leu Thr Gly Leu Ser Val Gly Phe Asp Tyr Trp Gly Gln
            100                 105                 110

Gly Thr Leu Val Thr Val Ser Ser
        115                 120

<210> SEQ ID NO 12
<211> LENGTH: 111
<212> TYPE: PRT
<213> ORGANISM: Homo sapiens

<400> SEQUENCE: 12

Asp Ile Val Leu Thr Gln Ser Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Thr Thr Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

```
Gln Ala Glu Asp Glu Ala Asp Tyr Tyr Cys Ser Ser Tyr Ser Ser Gly
                85                  90                  95

Ser Thr Pro Ala Leu Phe Gly Gly Gly Thr Gln Leu Thr Val Leu
            100                 105                 110

<210> SEQ ID NO 13
<211> LENGTH: 122
<212> TYPE: PRT
<213> ORGANISM: Homo sapiens

<400> SEQUENCE: 13

Gln Val Gln Leu Val Gln Ser Gly Gly Gly Leu Val Lys Pro Gly Gly
1               5                   10                  15

Ser Leu Arg Leu Ser Cys Gly Ala Ser Gly Phe Asn Leu Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Arg Ser Ser Tyr Ile Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Val Ser Pro Ser Thr Tyr Tyr Tyr Tyr Gly Met Asp Val Trp
            100                 105                 110

Gly Gln Gly Thr Thr Val Thr Val Ser Ser
            115                 120

<210> SEQ ID NO 14
<211> LENGTH: 108
<212> TYPE: PRT
<213> ORGANISM: Homo sapiens

<400> SEQUENCE: 14

Asp Ile Val Leu Thr Gln Pro Ser Ser Val Ser Val Ser Pro Gly Gln
1               5                   10                  15

Thr Ala Arg Ile Thr Cys Ser Gly Asp Glu Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Asn Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Val Val Phe Gly Gly Gly Thr Lys Leu Thr Val Leu
            100                 105

<210> SEQ ID NO 15
<211> LENGTH: 136
<212> TYPE: PRT
<213> ORGANISM: Homo sapiens
```

-continued

```
<400> SEQUENCE: 15

Gln Val Gln Leu Val Glu Ser Gly Ala Glu Val Lys Lys Pro Gly Ala
1               5                   10                  15

Leu Val Lys Val Ser Cys Lys Ala Ser Gly Tyr Thr Phe Ser Gly Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Gly Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Ala Arg Gly Gly Pro Ser Asn Leu Glu Arg Phe Leu Glu Arg Leu Gln
            100                 105                 110

Pro Arg Tyr Ser Tyr Asp Asp Lys Tyr Ala Met Asp Val Trp Gly Gln
        115                 120                 125

Gly Thr Thr Val Thr Val Ser Ser
    130                 135

<210> SEQ ID NO 16
<211> LENGTH: 109
<212> TYPE: PRT
<213> ORGANISM: Homo sapiens

<400> SEQUENCE: 16

Asp Ile Val Met Thr Gln Ser Pro Gly Thr Leu Ser Leu Ser Pro Gly
1               5                   10                  15

Ala Arg Ala Thr Leu Ser Cys Arg Ala Ser Gln Ser Val Ser Ser Ile
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys Arg
            100                 105

<210> SEQ ID NO 17
<211> LENGTH: 124
<212> TYPE: PRT
<213> ORGANISM: Homo sapiens

<400> SEQUENCE: 17

Gln Val Gln Leu Val Gln Ser Gly Thr Glu Val Lys Lys Pro Gly Glu
1               5                   10                  15

Ser Leu Lys Ile Ser Cys Glu Gly Ser Arg Tyr Asn Phe Ala Arg Tyr
            20                  25                  30

Trp Ile Gly Trp Val Arg Gln Met Pro Gly Lys Gly Leu Asp Trp Met
        35                  40                  45
```

Gly Ile Ile Tyr Pro Gly Asp Ser Asp Thr Arg Tyr Ser Pro Ser Phe
        50                  55                  60

Gln Gly Gln Val Ser Ile Ser Ala Asp Lys Ser Ile Ser Thr Ala Tyr
65                  70                  75                  80

Leu Gln Trp Asn Ser Leu Lys Ala Ser Asp Thr Ala Met Tyr Tyr Cys
                85                  90                  95

Ala Arg Leu Gly Ser Glu Leu Gly Val Val Ser Asp Tyr Tyr Phe Asp
            100                 105                 110

Ser Trp Gly Gln Gly Thr Leu Val Thr Val Ser Ser
            115                 120

<210> SEQ ID NO 18
<211> LENGTH: 114
<212> TYPE: PRT
<213> ORGANISM: Homo sapiens

<400> SEQUENCE: 18

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Asp Arg
            20                  25                  30

Ser Asn Asn Lys Asn Cys Val Ala Trp Tyr Gln Gln Lys Pro Gly Gln
        35                  40                  45

Pro Pro Lys Leu Leu Ile Tyr Arg Ala Ala Thr Arg Glu Ser Gly Val
    50                  55                  60

Pro Asp Arg Phe Ser Gly Ser Gly Ser Gly Thr Asp Phe Ser Leu Thr
65                  70                  75                  80

Ile Ser Ser Leu Gln Ala Glu Asp Val Ala Val Tyr Phe Cys Gln Gln
                85                  90                  95

Tyr Tyr Ser Ile Pro Asn Thr Phe Gly Gln Gly Thr Lys Leu Glu Ile
            100                 105                 110

Lys Arg

<210> SEQ ID NO 19
<211> LENGTH: 120
<212> TYPE: PRT
<213> ORGANISM: Homo sapiens

<400> SEQUENCE: 19

Gln Val Gln Leu Val Glu Ser Gly Gly Gly Leu Val Lys Ala Gly Gly
1               5                   10                  15

Ser Leu Arg Leu Ser Cys Val Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser Phe Ile Ser Ser Ser Gly Asp Thr Ile Phe Tyr Ala Asp Ser Val
    50                  55                  60

Lys Gly Arg Phe Thr Val Ser Arg Asp Ser Ala Lys Asn Ser Leu Tyr
65                  70                  75                  80

Leu Gln Met Asn Ser Leu Lys Val Glu Asp Thr Ala Val Tyr Tyr Cys
                85                  90                  95

Ala Arg Lys Gly Val Ser Asp Glu Glu Leu Leu Arg Phe Trp Gly Gln
            100                 105                 110

Gly Thr Leu Val Thr Val Ser Ser
            115                 120

```
<210> SEQ ID NO 20
<211> LENGTH: 108
<212> TYPE: PRT
<213> ORGANISM: Homo sapiens

<400> SEQUENCE: 20

Asp Ile Val Leu Thr Gln Asp Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Thr Lys Arg Pro Ser Gly Ile Pro Glu Arg Phe Ser Gly Ser
50                  55                  60

Ser Ser Gly Thr Val Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn Gln
                85                  90                  95

Arg Val Phe Gly Gly Gly Thr Lys Leu Thr Val Leu
            100                 105

<210> SEQ ID NO 21
<211> LENGTH: 116
<212> TYPE: PRT
<213> ORGANISM: Homo sapiens

<400> SEQUENCE: 21

Gln Val Gln Leu Val Glu Ser Gly Thr Glu Val Lys Asn Pro Gly Ala
1               5                   10                  15

Ser Val Lys Val Ser Cys Thr Ala Ser Gly Tyr Lys Phe Asp Glu Tyr
            20                  25                  30

Gly Val Ser Trp Val Arg Gln Ser Pro Gly Gln Gly Leu Glu Trp Met
        35                  40                  45

Gly Trp Ile Ser Val Tyr Asn Gly Lys Thr Asn Tyr Ser Gln Asn Phe
50                  55                  60

Gln Gly Arg Leu Thr Leu Thr Thr Glu Thr Ser Thr Asp Thr Ala Tyr
65                  70                  75                  80

Met Glu Leu Thr Ser Leu Arg Pro Asp Asp Thr Ala Val Tyr Tyr Cys
                85                  90                  95

Ala Thr Asp Lys Asn Trp Phe Asp Pro Trp Gly Pro Gly Thr Leu Val
            100                 105                 110

Thr Val Ser Ser
        115

<210> SEQ ID NO 22
<211> LENGTH: 107
<212> TYPE: PRT
<213> ORGANISM: Homo sapiens

<400> SEQUENCE: 22

Asp Ile Val Leu Thr Gln Ser Pro Ser Ala Ser Gly Ser Pro Gly Gln
1               5                   10                  15

Ser Ile Thr Ile Ser Cys Thr Gly Thr Asn Thr Asp Tyr Asn Tyr Val
            20                  25                  30

Ser Trp Tyr Gln His Pro Gly Lys Ala Pro Lys Val Ile Ile Tyr
        35                  40                  45
```

```
Asp Val Lys Lys Arg Pro Ser Gly Val Pro Ser Arg Phe Ser Gly Ser
        50                  55                  60
Arg Ser Gly Asn Thr Ala Thr Leu Thr Val Ser Gly Leu Gln Thr Glu
 65                  70                  75                  80
Asp Glu Ala Asp Tyr Tyr Cys Val Ser Tyr Ala Asp Asn Asn His Tyr
                 85                  90                  95
Val Phe Gly Ser Gly Thr Lys Val Thr Val Leu
                100                 105
```

<210> SEQ ID NO 23
<211> LENGTH: 113
<212> TYPE: PRT
<213> ORGANISM: Homo sapiens

<400> SEQUENCE: 23

```
Gln Val Gln Leu Val Glu Ser Gly Ala Glu Val Lys Lys Pro Gly Glu
 1               5                  10                  15
Ser Leu Lys Ile Ser Cys Lys Gly Ser Gly Tyr Asn Phe Thr Ser Tyr
                20                  25                  30
Trp Ile Gly Trp Val Arg Gln Met Pro Gly Lys Gly Leu Glu Trp Met
             35                  40                  45
Gly Val Ile Tyr Pro Asp Asp Ser Asp Thr Arg Tyr Ser Pro Ser Phe
 50                  55                  60
Lys Gly Gln Val Thr Ile Ser Ala Asp Lys Ser Ile Ser Thr Ala Phe
 65                  70                  75                  80
Leu Gln Trp Ser Ser Leu Lys Ala Ser Asp Thr Ala Val Tyr His Cys
                 85                  90                  95
Ala Arg Pro Pro Asp Ser Trp Gly Gln Gly Thr Leu Val Thr Val Ser
                100                 105                 110
Ser
```

<210> SEQ ID NO 24
<211> LENGTH: 108
<212> TYPE: PRT
<213> ORGANISM: Homo sapiens

<400> SEQUENCE: 24

```
Asp Ile Val Met Thr Gln Ser Pro Ala Thr Leu Ser Val Ser Pro Gly
 1               5                  10                  15
Glu Arg Ala Thr Leu Ser Cys Arg Ala Ser Gln Ser Val Ser Ser Asn
                20                  25                  30
Leu Ala Trp Tyr Gln Gln Lys Pro Gly Leu Ala Pro Arg Leu Leu Ile
             35                  40                  45
Val Gly Ala Ser Asn Arg Ala Thr Gly Ile Pro Ala Arg Phe Ser Gly
 50                  55                  60
Ser Gly Ser Gly Thr Glu Phe Thr Leu Thr Ile Ser Ser Leu Gln Ser
 65                  70                  75                  80
Glu Asp Phe Ala Phe Tyr Tyr Cys Gln Gln Tyr Asn Asn Trp Pro Phe
                 85                  90                  95
Thr Phe Gly Pro Gly Thr Lys Val Asp Val Lys Arg
                100                 105
```

<210> SEQ ID NO 25
<211> LENGTH: 120
<212> TYPE: PRT
<213> ORGANISM: Homo sapiens

<400> SEQUENCE: 25

Gln Val Gln Leu Leu Glu Ser Gly Pro Gly Leu Val Lys Pro Ser Glu
1               5                   10                  15

Thr Pro Ser Leu Thr Cys Thr Val Ser Gly Gly Ser Ile Arg Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Met Ser Lys Asn Gln Phe Ser Leu
65                  70                  75                  80

Lys Leu Ser Ser Val Thr Ala Ala Asp Thr Ala Met Tyr Tyr Cys Ala
                85                  90                  95

Arg Val Tyr Gly Gly Ser Gly Ser Tyr Asp Phe Asp Tyr Trp Gly Gln
            100                 105                 110

Gly Thr Leu Val Thr Val Ser Ser
        115                 120

<210> SEQ ID NO 26
<211> LENGTH: 111
<212> TYPE: PRT
<213> ORGANISM: Homo sapiens

<400> SEQUENCE: 26

Asp Ile Val Leu Thr Gln Ser Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln Leu Pro Gly Lys Ala Pro Lys Leu
        35                  40                  45

Met Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Phe Ala Gly Ser
                85                  90                  95

Asn Asn His Val Val Phe Gly Gly Gly Thr Lys Leu Thr Val Leu
            100                 105                 110

<210> SEQ ID NO 27
<211> LENGTH: 111
<212> TYPE: PRT
<213> ORGANISM: Homo sapiens

<400> SEQUENCE: 27

Asp Ile Val Leu Thr Gln Ser Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln Leu Pro Gly Lys Ala Pro Lys Leu
        35                  40                  45

Met Ile Tyr Glu Val Thr Lys Arg Pro Ser Gly Val Pro Asp Arg Phe
    50                  55                  60

```
Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Phe Ala Gly Ser
                 85                  90                  95

Asn Asn His Val Val Phe Gly Gly Gly Thr Lys Leu Thr Val Leu
            100                 105                 110

<210> SEQ ID NO 28
<211> LENGTH: 108
<212> TYPE: PRT
<213> ORGANISM: Homo sapiens

<400> SEQUENCE: 28

Asp Ile Glu Met Thr Gln Ser Pro Ser Val Ser Val Ser Pro Gly Gln
1               5                   10                  15

Thr Ala Arg Ile Thr Cys Ser Gly Glu Pro Leu Ala Lys Gln Tyr Ala
            20                  25                  30

Tyr Trp Tyr Gln Gln Lys Ser Gly Gln Ala Pro Val Val Val Ile Tyr
        35                  40                  45

Lys Asp Thr Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr His Cys Glu Ser Gly Asp Ser Ser Gly Thr Tyr
                 85                  90                  95

Pro Val Phe Gly Gly Gly Thr Lys Leu Thr Val Leu
            100                 105

<210> SEQ ID NO 29
<211> LENGTH: 117
<212> TYPE: PRT
<213> ORGANISM: Homo sapiens

<400> SEQUENCE: 29

Gln Val Gln Leu Gln Glu Ser Gly Gly Gly Leu Val Gln Pro Gly Gly
1               5                   10                  15

Ser Leu Lys Leu Ser Cys Ala Ala Ser Gly Phe Ile Phe Ser Gly Ser
            20                  25                  30

Thr Met His Trp Val Arg Gln Ala Ser Gly Lys Gly Leu Glu Trp Val
        35                  40                  45

Gly Arg Ile Arg Ser Lys Thr Asn Asn Tyr Ala Thr Ala Tyr Ala Ala
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Ile Ser Leu Pro Gly Gly Tyr Ser Ser Gly Gln Gly Thr Leu
            100                 105                 110

Val Thr Val Ser Ser
            115

<210> SEQ ID NO 30
<211> LENGTH: 108
<212> TYPE: PRT
<213> ORGANISM: Homo sapiens
```

<400> SEQUENCE: 30

Asp Ile Met Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Thr
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Glu Ile Pro Glu Arg Phe Ser Ala Phe
    50                  55                  60

Thr Ser Trp Thr Thr Ala Thr Leu Thr Ile Thr Gly Ala Gln Val Gly
65                  70                  75                  80

Asp Glu Ala Asp Tyr Tyr Cys Tyr Ser Thr Asp Ile Thr Gly Asp Ile
                85                  90                  95

Gly Val Phe Gly Gly Gly Thr Lys Leu Thr Val Leu
            100                 105

<210> SEQ ID NO 31
<211> LENGTH: 124
<212> TYPE: PRT
<213> ORGANISM: Homo sapiens

<400> SEQUENCE: 31

Gln Val Gln Leu Val Gln Ser Gly Gly Gly Leu Val Gln Pro Gly Gly
1               5                   10                  15

Ser Leu Lys Val Ser Cys Val Gly Ser Gly Phe Thr Phe Ser Ala Ser
            20                  25                  30

Thr Ile His Trp Val Arg Gln Ala Ser Gly Lys Gly Leu Glu Trp Val
        35                  40                  45

Gly Arg Ile Arg Ser Lys Ala Asn Asn Tyr Ala Thr Val Ser Ala Ala
    50                  55                  60

Ser Leu Lys Gly Arg Phe Thr Ile Ser Arg Asp Asp Ser Lys Asn Thr
65                  70                  75                  80

Ala Tyr Leu Gln Val Asn Ser Leu Lys Ile Glu Asp Thr Ala Ile Tyr
                85                  90                  95

Tyr Cys Thr Arg Pro Thr Ala Cys Gly Asp Arg Val Cys Trp His Gly
            100                 105                 110

Ala Trp Gly Gln Gly Thr Gln Val Thr Val Ser Pro
        115                 120

<210> SEQ ID NO 32
<211> LENGTH: 110
<212> TYPE: PRT
<213> ORGANISM: Homo sapiens

<400> SEQUENCE: 32

Asp Ile Val Leu Thr Gln Ser Pro Ser Ala Ser Gly Thr Pro Gly Gln
1               5                   10                  15

Arg Val Thr Ile Ser Cys Ser Gly Ser Arg Ser Asn Leu Gly Asn Asn
            20                  25                  30

Asn Val Asn Trp Tyr Gln Gln Leu Pro Gly Thr Ala Pro Lys Leu Leu
        35                  40                  45

Ile Phe Asp Asn Asn Glu Arg Pro Ser Gly Val Pro Gly Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
            85                  90                  95

Asn Gly Trp Val Phe Gly Gly Gly Thr Lys Val Thr Val Leu
            100                 105                 110

<210> SEQ ID NO 33
<211> LENGTH: 124
<212> TYPE: PRT
<213> ORGANISM: Homo sapiens

<400> SEQUENCE: 33

Gln Val Gln Leu Val Glu Ser Gly Gly Gly Leu Ala Gln Pro Gly Gly
1               5                   10                  15

Ser Leu Arg Leu Ser Cys Ala Ala Ser Gly Phe Ile Phe Asn Thr Tyr
            20                  25                  30

Ala Met Gly Trp Val Arg Gln Ala Pro Gly Lys Gly Leu Glu Trp Val
        35                  40                  45

Ser Thr Val Ser Ala Pro Gly Ala Gly Thr Tyr Tyr Thr Asp Ser Val
    50                  55                  60

Lys Gly Arg Phe Ile Ile Ser Arg Asp Asn Ser Lys Asn Ile Leu Tyr
65                  70                  75                  80

Leu Gln Met Asn Arg Leu Arg Val Glu Asp Thr Ala Val Tyr Tyr Cys
                85                  90                  95

Ala Arg Asp Gln Gly Gly Pro Ala Val Ala Gly Ala Arg Ile Phe Asp
            100                 105                 110

Tyr Trp Gly Gln Gly Ala Leu Val Thr Val Ser Ser
        115                 120

<210> SEQ ID NO 34
<211> LENGTH: 112
<212> TYPE: PRT
<213> ORGANISM: Homo sapiens

<400> SEQUENCE: 34

Asp Ile Val Leu Thr Gln Ser Pro Leu Ser Leu Ser Val Thr Pro Gly
1               5                   10                  15

Gln Pro Ala Ser Ile Ser Cys Lys Ser Ser Gln Ser Leu Leu Arg Ser
            20                  25                  30

Asp Gly Lys Thr Tyr Leu Cys Trp Tyr Leu Gln Lys Pro Gly Gln Pro
        35                  40                  45

Pro Gln Leu Leu Ile Tyr Glu Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Arg Thr Phe Gly Gln Gly Thr Lys Val Glu Ile Lys Arg
            100                 105                 110

<210> SEQ ID NO 35
<211> LENGTH: 357
<212> TYPE: DNA
<213> ORGANISM: Homo sapiens

<400> SEQUENCE: 35
caggtgcagc tggtggagtc cggcccagga ctggtgaagc cttcggagac cctgtccctc       60
acctgcaggg tctctggtga ctccaatcgg ccttcctact ggagctggat caggcaggcc     120

```
ccagggaagg caatggagtg ataggttat gtctatgaca gtggggtcac catctacaat    180
ccctccctca agggtcgagt cacaatatca ctagacacgt cgaagacgcg gttctccctg   240
aaactgacct ctgtgatcgc tgcggacacg gccgtatatt attgtgcgcg agaacgtttt   300
gatcggacat cgtataagag ttggtggggc cagggaacgc aggtcaccgt ctcctca      357
```

<210> SEQ ID NO 36
<211> LENGTH: 324
<212> TYPE: DNA
<213> ORGANISM: Homo sapiens

<400> SEQUENCE: 36

```
gatatcgtgc tgactcaggc cccaggcact ctgtctttgt ctccagggga cagagccacc    60
ctctcctgta gggccagtca gcgtcttggc ggcacgtcct tagcctggta ccagcacaga   120
tctggccagg ctcccaggct catcctctac ggaacttcaa acagggccac tgacccccct   180
gacaggttta gtggcagtgg gtctgggaca gacttcgttc tcaccatcag ttccctggag   240
cctgaagatt ttgcagtgta ttactgtcag caatatggca gcccaccgta cacttttggc   300
caggggacca ctctggacat caaa                                          324
```

<210> SEQ ID NO 37
<211> LENGTH: 366
<212> TYPE: DNA
<213> ORGANISM: Homo sapiens

<400> SEQUENCE: 37

```
caggtgcagc tggtgcagtc tgggggaacc ttggtccagc cggggggggtc cctgagactc   60 tcctgtgcag cctctggatt caccttagt tactactcga tgagctgggt ccgccaggct   120
ccagggaagg ggctggagtg ggtggccaac ataaagcacg atggaactga gagaaattat   180
gtggactctg tgaagggccg attcaccatc tccagagaca cagcgagaa gtctctttac   240 ctgcaaatga acagcctgag agccgaggac acggctgtgt attactgtgc gaagtattat   300
tatggtgccg ggactaatta tcccccttaag tactggggcc agggaacccg ggtcaccgtc   360
tcctca                                                              366
```

<210> SEQ ID NO 38
<211> LENGTH: 324
<212> TYPE: DNA
<213> ORGANISM: Homo sapiens

<400> SEQUENCE: 38

```
gatatcctga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagctcct gatctatgct gcatccagtt tacaaagtgg ggtcccatca   180
aggttcagcg gcagtggatc tggcacagat ttcactctca ccatcagcag cctgcagcct   240
gaagattttg caacttatta ctgtctacaa gattacaatt acccgctcac ttttcggcgga   300 gggaccaagg tggagatcaa acga                                          324
```

<210> SEQ ID NO 39
<211> LENGTH: 348
<212> TYPE: DNA
<213> ORGANISM: Homo sapiens

<400> SEQUENCE: 39

```
caggtgcagc tgctcgagtc aggcccaggc ctggttaggc cctcggacac cctgtccctc    60
acctgcactt tttccgctga cctcagcacc aacgcctatt ggacctggat ccggcagccc   120
ccaggaaagg gactggagtg gattggctat atgtctcata gtgggggaag ggattacaat   180
ccctccttca accggcgagt caccatttca gtggacacgt cgaagaacca ggttttcttg   240
aggctgacgt cagtgacctc tgcggacacg gccgtctatt tctgtgtgag agaagtcggc   300
agttactacg actactgggg ccagggaatc ctggtcaccg tctcctca               348
```

<210> SEQ ID NO 40
<211> LENGTH: 324
<212> TYPE: DNA
<213> ORGANISM: Homo sapiens

<400> SEQUENCE: 40

```
gatatcgaga tgacccagtc tccatcctct ttgtctgcat ctgtcggaga cagaatcacc    60
atcacttgtc gggcgagtca gggtattagc acctggttag cctggtatca gcagaaaccg   120
ggaaagccc ctaagtccct gatctttttct acgtccagcc tgcatagtgg ggtcccctca   180
aagttcagcg gcagtgggtc tgggacagac ttcactctca ccatcaccaa cctgcagcct   240
gaagattttg caacttatta ctgccaacag aaatgggaga ccccttatag ttttggccag   300
gggaccaagc tggacatgat acga                                         324
```

<210> SEQ ID NO 41
<211> LENGTH: 348
<212> TYPE: DNA
<213> ORGANISM: Homo sapiens

<400> SEQUENCE: 41

```
caggtgcagc tggtggagtc tggaactgag gtgaagaacc ctggagcctc agtgaaggtc    60
tcctgcacgg cctctggtta caaatttgac gaatatggtg tcagttgggt gcgacagtcc   120
cctggacaag gacttgagtg gatgggatgg atcagtgttt ataatggcaa gacaaactat   180
agccagaact tcagggcag actcaccctg accacagaga catccaccga cacagcctac   240
atggagctta cgagcctcag acctgacgac acggccgtct attactgtgc gacagacaaa   300
aactggttcg accccggg cccgggaacc ctggtcaccg tctcctca               348
```

<210> SEQ ID NO 42
<211> LENGTH: 321
<212> TYPE: DNA
<213> ORGANISM: Homo sapiens

<400> SEQUENCE: 42

```
gatatcgtga tgacccagtc tccctccgcg tccgggtctc ctggacagtc aatcaccatc    60
tcctgcactg gaaccaacac tgattataat tatgtttcct ggtaccagca ccaccccggc   120
aaagcccca agtcattat ttatgacgtc aaaaagcggc cctcggggt ccctagtcgc     180
ttctctggct ccaggtctgg caacacggcc accctgaccg tctctgggct ccagactgag   240
gatgaggctg attattattg tgtctcatat gcagacaaca atcattatgt cttcggaagt   300
gggaccaagg tcaccgtcct g                                             321
```

<210> SEQ ID NO 43
<211> LENGTH: 384
<212> TYPE: DNA
<213> ORGANISM: Homo sapiens

<400> SEQUENCE: 43

```
caggtgcagc tggtggagtc cggggggaggc gtggtccagc ctggagggtc cctgagagtc    60
tcctgtgcag cctctgcgtt cagtttcagg gattatggca tacactgggt ccgccaggct   120
ccaggcaagg ggctgcaatg ggtggcggtt atttcacatg atggaggtaa gaaattctat   180
gcagactccg tgaggggccg attcaccatc tccagagaca attccgagaa cacactgtat   240
ctccaaatga acagcctgag atctgacgac acggctgtct attactgtgc gaggctcgtt   300
gccagttgca gtggttccac ctgcacaacg caacctgctg cctttgacat ttggggccca   360
gggacattgg tcaccgtctc ttca                                          384
```

<210> SEQ ID NO 44
<211> LENGTH: 324
<212> TYPE: DNA
<213> ORGANISM: Homo sapiens

<400> SEQUENCE: 44

```
gatatcatgc tgactcagcc gccctcggtg tcagtgtccc caggacaaac ggccaggatc    60
acctgctctg gagatgcatt gccaaaaaaa tatacttatt ggtatcagca gaagtcaggc   120
caggcccctg ttctgctcat ctatgaggac aggaaacgac cctccgagat ccctgagaga   180
ttctctgcct tcacctcatg gacgacggcc accttgacta tcactggggc caggtgaga   240
gatgaagctg actactactg ttattcaaca gacatcagtg gtgatatagg agtgttcggc   300
ggagggacca agctgaccgt ccta                                          324
```

<210> SEQ ID NO 45
<211> LENGTH: 333
<212> TYPE: DNA
<213> ORGANISM: Homo sapiens

<400> SEQUENCE: 45

```
gatatcgtgc tgactcagtc ggcctccgtg tctgggtctc ctggacagtc gatcaccatc    60
tcctgcactg gaaccagcag tgacgttggt ggatataact atgtctcctg gtaccaacaa   120
cacccaggca aagcccccaa actcatgatt tatgatgtca ctactcggcc ttcaggggtt   180
tctgatcgct tctctggctc caagtctggc aacacggcct ccctgaccat ctctgggctg   240
caggctgagg acgaggctga ttattattgc agctcatatt caagcggctc cacacctgct   300
ctgtttgggg ggggcaccca gctgaccgtc ctc                                333
```

<210> SEQ ID NO 46
<211> LENGTH: 333
<212> TYPE: DNA
<213> ORGANISM: Homo sapiens

<400> SEQUENCE: 46

```
gatatcgtgc tgactcagtc ggcctccgtg tctgggtctc ctggacagtc gatcaccatc    60
tcctgcactg gaaccagcag tgacgttggt ggatataact atgtctcctg gtaccaacaa   120
cacccaggca aagcccccaa actcatgatt tatgatgtca ctactcggcc ttcaggggtt   180
tctgatcgct tctctggctc caagtctggc aacacggcct ccctgaccat ctctgggctg   240
caggctgagg acgaggctga ttattattgc agctcatatt caagcggctc cacacctgct   300
ctgtttgggg ggggcaccca gctgaccgtc ctc                                333
```

<210> SEQ ID NO 47
<211> LENGTH: 366
<212> TYPE: DNA
<213> ORGANISM: Homo sapiens

<400> SEQUENCE: 47

```
caggtgcagc tggtgcagtc tggggagggc ctggtcaagc ctgggggtc cctgagactc      60
tcctgtggag cctctggatt taacctcagt agttatagca tgaactgggt ccgccaggct     120
ccagggaagg ggctggagtg ggtctcatcc attagtagta gaagtagtta catatactat    180
gcagactcag tgcagggccg attcaccatc tccagagaca acgccaagaa ctcactgtat    240
ctgcaaatga acagcctgag agccgaggac acggctatat attactgtgc gagagtatct    300
ccgtccacct attattatta tggtatggac gtctggggcc aagggaccac ggtcaccgtc    360
tcctca                                                                366
```

<210> SEQ ID NO 48
<211> LENGTH: 324
<212> TYPE: DNA
<213> ORGANISM: Homo sapiens

<400> SEQUENCE: 48

```
gatatcgtac tcactcagcc gtcctcggtg tcagtgtccc caggacagac ggccaggatc      60
acctgctctg gagatgaatt gccaaagcaa tatgcttatt ggtaccagca gaagccaggc    120
caggcccctg tgttggtaat atataaagac aatgagaggc cctcagggat ccctgagcga    180
ttctctggct ccagctcagg gacaacagtc acgttgacca tcagtggagt ccaggcagaa    240
gacgaggctg actattactg tcaatcagca gacagtagtg gtacttatgt ggtgttcggc    300
ggagggacca agctgaccgt ccta                                            324
```

<210> SEQ ID NO 49
<211> LENGTH: 408
<212> TYPE: DNA
<213> ORGANISM: Homo sapiens

<400> SEQUENCE: 49

```
caggtgcagc tggtggagtc tggggctgag gtgaagaagc ctggggcctt agtgaaggtc      60
tcctgcaagg cttctggata caccttcagc ggctactata tgcactgggt gcgacaggcc    120
cctggacaag ggcttgagtg gatgggatgg atcaaccctta agagtggtgg cacaaagtat    180
gcacagaagt tcagggccg gtcaccatg accagggaca cgtccatcag cacagcctac    240
atggagttga gcaggctaag atctgacgac acggccgtgt atttctgtgc gagaggcgga    300
ccttcaaatt tggaacgatt tttgagagg ttacaaccccc gctacagtta cgacgacaag    360
tatgctatgg acgtctgggg ccaagggacc acggtcaccg tctcctca                 408
```

<210> SEQ ID NO 50
<211> LENGTH: 328
<212> TYPE: DNA
<213> ORGANISM: Homo sapiens

<400> SEQUENCE: 50

```
gatatcgtga tgacccagtc tccaggcacc ctgtctttgt ctccaggggc aagagccacc      60
ctctcctgca gggccagtca gagtgttagc agcatctatt tagcctggta ccagcagaaa    120
cctggccagg ctcccaggct cctcatcttt ggtgcatcca gcagggccac tggcatccca    180
gacaggttca gtggcagtgg gtctgggaca gacttcactc tcaccatcag cagactggag    240
```

```
cctgaagatt ttgcagtgta ttactgtcag cagtatggta gctcaccgta cacttttggc    300
caggggacca agctggagat caaacgaa                                        328

<210> SEQ ID NO 51
<211> LENGTH: 372
<212> TYPE: DNA
<213> ORGANISM: Homo sapiens

<400> SEQUENCE: 51
caggtgcagc tggtgcagtc tggaacagaa gtgaaaaagc cggggagtc tctgaagatc      60 tcctgtgagg gttctcgata caactttgcc aggtactgga tcggctgggt gcgccagatg    120
cccggaaaag gcctggactg gatggggatc atctatcctg gtgactccga taccagatac    180
agcccgtcct ccaaggcca ggtcagcatc tcagccgaca gtccatcag taccgcctac      240 ctgcagtgga acagcctgaa ggcctcggac accgccatgt attattgtgc gagacttggg    300
agcgagcttg gagtggtctc tgattattac tttgactcct ggggccaggg aaccctggtc    360
accgtctcct ca                                                         372

<210> SEQ ID NO 52
<211> LENGTH: 342
<212> TYPE: DNA
<213> ORGANISM: Homo sapiens

<400> SEQUENCE: 52
gatatcgtgt tgactcagtc tccagactcc ctggctgtgt ctctgggcga gagggccacc     60
atcaactgca gtccagcca gagtgtttta gacaggtcca acaataagaa ctgtgtagct    120
tggtaccagc agaaaccggg acagcctcct aaactgctca tttaccgggc tgctacccgg    180
gaatccgggg tccctgatcg attcagtggc agcgggtctg ggacagactt cagtctcacc    240
atcagcagcc tgcaggctga agatgtggca gtttatttct gtcagcaata ttatagtatt    300
ccgaacactt ttggccaggg gaccaagctg gagatcaaac ga                       342

<210> SEQ ID NO 53
<211> LENGTH: 360
<212> TYPE: DNA
<213> ORGANISM: Homo sapiens

<400> SEQUENCE: 53
caggtgcagc tggtggagtc tgggggaggc ttggtcaagg ctggagggtc cctgagactc     60
tcctgtgtag cctctggatt caccttcagc gactactaca tgtcctggat tcgccaggct    120
ccagggaagg ggctggagtg gatttcattt attagtagta gtggtgatac cataattttac   180 gcagactctg tgaagggccg attcaccgtc tccagggaca cgccaagaa ctcactgtat     240 cttcaaatga acagcctgaa agtcgaggac acggccgtgt attactgtgc gaggaagggg    300
gtgtccgacg aggaactact gcgcttctgg ggccagggaa ccctggtcac cgtctcctca    360

<210> SEQ ID NO 54
<211> LENGTH: 324
<212> TYPE: DNA
<213> ORGANISM: Homo sapiens

<400> SEQUENCE: 54
gatatcgtgc tgactcagga ccccctcggtg tcagtgtccc caggacaaac ggccaggatc     60
acctgctctg gagatgcatt gccaaaaaaa tatgcttatt ggtaccagca gaagtcaggc    120
caggcccctg tgctggtcat ctatgaggac accaaacgac cctccgggat ccctgagaga    180
```

```
ttctctggct ccagctcagg gacagtggcc accttgacta tcagtggggc ccaggtggag      240
gatgaagctg actactattg ttactcaaca gacagcagcg gtaatcagag ggtattcggc      300
ggagggacca agctgaccgt ccta                                             324

<210> SEQ ID NO 55
<211> LENGTH: 348
<212> TYPE: DNA
<213> ORGANISM: Homo sapiens

<400> SEQUENCE: 55
caggtgcagc tggtggagtc tggaactgag gtgaagaacc ctggagcctc agtgaaggtc       60
tcctgcacgg cctctggtta caaatttgac gaatatggtg tcagttgggt gcgacagtcc      120
cctggacaag gacttgagtg gatgggatgg atcagtgttt ataatggcaa gacaaactat      180
agccagaact ttcagggcag actcaccctg accacagaga catccaccga cacagcctac      240
atggagctta cgagcctcag acctgacgac acggccgtct attactgtgc tacagacaaa      300
aactggttcg acccctgggg cccgggaacc ctggtcaccg tctcctca                   348

<210> SEQ ID NO 56
<211> LENGTH: 348
<212> TYPE: DNA
<213> ORGANISM: Homo sapiens

<400> SEQUENCE: 56
caggtgcagc tggtggaaag cggcaccgaa gtgaagaacc caggcgccag cgtgaaggtg       60
tcctgtacag ccagcggcta caagttcgac gagtacggcg tgtcctgggt gcgccagtct      120
cctggacagg gcctggaatg gatgggctgg atcagcgtgt acaacggcaa gaccaactac      180
agccagaact tccagggccg gctgaccctg accaccgaga caagcaccga caccgcctac      240
atggaactga ccagcctgag gcccgacgat accgccgtgt actactgcgc caccgacaag      300
aattggttcg acccctgggg ccctggcacc ctcgtgacag tgtctagc                   348

<210> SEQ ID NO 57
<211> LENGTH: 321
<212> TYPE: DNA
<213> ORGANISM: Homo sapiens

<400> SEQUENCE: 57
gatatcgtgt tgactcagtc tccctccgcg tccgggtctc ctggacagtc aatcaccatc       60
tcctgcactg gaaccaacac tgattataat tatgtttcct ggtaccagca ccaccccggc      120
aaagccccca agtcattat ttatgacgtc aaaaagcggc cctcggggt ccctagtcgc      180 ttctctggct ccaggtctgg caacacggcc accctgaccg tctctgggct ccagactgag      240
gatgaggctg attattattg tgtctcatat gcagacaaca atcattatgt cttcggaagt      300
gggaccaagg tcaccgtcct g                                                321

<210> SEQ ID NO 58
<211> LENGTH: 321
<212> TYPE: DNA
<213> ORGANISM: Homo sapiens

<400> SEQUENCE: 58
gatatcgtgc tgacacagag ccctagcgcc agcggctctc ctggccagag catcaccatc       60
agctgcaccg gcaccaacac cgactacaac tacgtgtcct ggtatcagca ccaccccggc      120
aaggccccca agtgatcat ctacgacgtg aagaaacggc ccagcggcgt gcccagcaga      180
```

```
ttcagcggaa gcagaagcgg caacaccgcc accctgacag tgtctggcct gcagacagag      240
gacgaggccg actactactg tgtgtcctac gccgacaaca accactacgt gttcggcagc      300
ggcaccaaag tgaccgtgct g                                                321

<210> SEQ ID NO 59
<211> LENGTH: 339
<212> TYPE: DNA
<213> ORGANISM: Homo sapiens

<400> SEQUENCE: 59
caggtgcagc tggtggagtc tggagcagag gtgaaaaagc ccggggagtc tctgaagatc       60
tcctgtaagg gctctggata caactttacc agttactgga tcggctgggt gcgccagatg      120
cccgggaaag gcctggagtg gatgggagtc atctatcctg atgactctga taccagatac      180
agcccgtcat tcaaaggcca agtcaccata tcagccgaca gtccatcagc accgccttc       240 ctgcagtgga gcagtctaaa ggcctcggac accgccgtgt atcactgtgc gagaccccg       300 gactcctggg gccagggaac cctggtcacc gtctcctca                             339

<210> SEQ ID NO 60
<211> LENGTH: 324
<212> TYPE: DNA
<213> ORGANISM: Homo sapiens

<400> SEQUENCE: 60
gatatcgtga tgacgcagtc tccggccacc ctgtctgtgt ctccagggga aagagccacc       60
ctctcctgca gggccagtca gagtgttagc agcaacttag cctggtacca gcagaaacct      120
ggcttggctc ccagactcct catcgtgggt gcatccaaca gggccactgg tatcccagcc      180
aggttcagtg gcagtgggtc tgggacagag ttcactctca ccatcagcag cctgcagtct      240
gaagattttg catttttatta ctgtcagcag tataataact ggccattcac tttcggccct      300
gggaccaaag tggatgtcaa acga                                             324

<210> SEQ ID NO 61
<211> LENGTH: 360
<212> TYPE: DNA
<213> ORGANISM: Homo sapiens

<400> SEQUENCE: 61
caggtgcagc tgctcgagtc aggcccagga ctggtgaagc cttcggagac cccgtccctc       60
acctgcactg tctctggtgg ctccatcagg agttactact ggagctggat ccggcagccc      120
ccagggaagg gactggagtg gattggatat atctattaca gtgggagcac caactacaac      180
ccctccctca agagtcgagt caccatatca gtagacatgt ccaagaacca gttctccctg      240
aagctgagct ctgtgaccgc cgcagacacg gccatgtatt actgtgcgag agtctacgga      300
ggttcgggga gttacgactt tgattactgg ggccagggaa ccctggtcac cgtctcctca      360

<210> SEQ ID NO 62
<211> LENGTH: 333
<212> TYPE: DNA
<213> ORGANISM: Homo sapiens

<400> SEQUENCE: 62
gatatcgtgt tgacccagtc tcctccgcg tccgggtctc ctggacagtc agtcaccatc        60
tcctgcactg gaaccagcag tgacgttggt ggttataact atgtctcctg gtaccaacag      120
ctcccaggca agcccccaa actcatgatt tatgaggtca ctaagcggcc ctcaggggtc       180
```

```
cctgatcgct tctctggctc caagtctggc aacacggcct ccctgaccgt ctctgggctc    240
caggctgagg atgaggctga ttattactgc agctcatttg caggcagcaa caaccatgtg    300
gtattcggcg agggaccaa gctgaccgtc cta                                  333

<210> SEQ ID NO 63
<211> LENGTH: 390
<212> TYPE: DNA
<213> ORGANISM: Homo sapiens

<400> SEQUENCE: 63
caggtgcagc tgaccttgag ggagtctggt cctacgctgg tgaaacccac acagaccctc     60
acgctgacct gcaccttctc tgggttctca ctcagcacta atggagtggg tgtgggctgg    120
atccgtcagc ccccaggaaa ggccctggag tggcttgcaa tcatttattg ggatgatgat    180
aagcgctaca gtccatctct gaaaagcagg ctcaccatca ccaaggacac ctccaaaaac    240
caggtggtcc ttacactgac caacatggac cctgtggaca caggcacata ttactgtgca    300 cacatttag gcgcgtcgaa ttattggact ggttatttga ggtactactt tgactactgg    360
ggccagggaa ccctggtcac cgtctccaca                                     390

<210> SEQ ID NO 64
<211> LENGTH: 324
<212> TYPE: DNA
<213> ORGANISM: Homo sapiens

<400> SEQUENCE: 64
gatatcgaga tgacccagtc tccctcggtg tcagtgtccc caggacagac ggccaggatc     60
acctgctctg gagaaccatt ggcaaagcaa tatgcttatt ggtatcagca gaagtcaggc    120
caggcccctg tggtggtgat atataaagac actgagaggc cctcaggat ccctgagcga    180 ttctctggct ccagctcagg gacaacagtc acgttgacca tcagtggagt ccaggcagaa    240
gacgaggctg actatcactg tgaatcagga gacagcagtg gtacttatcc ggtattcggc    300
ggagggacca agctgaccgt ccta                                           324

<210> SEQ ID NO 65
<211> LENGTH: 351
<212> TYPE: DNA
<213> ORGANISM: Homo sapiens

<400> SEQUENCE: 65
caggtgcagc tgcaggagtc ggggggaggc ttggtccagc ctgggggtc cctgaaactc     60 tcctgtgcag cctctgggtt catcttcagt ggctctacta tgcactgggt ccgccaggct    120
tccgggaaag gctggagtg ggttggccgt atcagaagca aaactaacaa ttacgcgaca    180
gcatatgctg cgtcggtgaa aggcaggttc accatctcca gagatgattc aaagaacacg    240
gcgtatctgc aaatgaacag cctgaaaacc gaggacacgg ccgtgtatta ttgtattagc    300
ttacctggcg ggtatagcag tggacaggga accctggtca ccgtctcctc a            351

<210> SEQ ID NO 66
<211> LENGTH: 324
<212> TYPE: DNA
<213> ORGANISM: Homo sapiens

<400> SEQUENCE: 66
gatatcatgc tgactcagcc accctcggtg tcagtgtccc caggacaaac ggccaggatc     60
acctgctctg gagatgcatt gccaaaaaaa tatacttatt ggtatcagca gaagtcaggc    120
```

```
caggcccctg ttttggtcat ctatgaggac agcaaacgac cctccgagat ccctgagaga    180
ttctctgcct tcacctcatg gacgacggcc accttgacta taactggggc ccaggtggga    240
gatgaagctg actactactg ttattcaaca gacatcactg gtgatatagg agtgttcggc    300
ggagggacca agctgaccgt cctg                                           324

<210> SEQ ID NO 67
<211> LENGTH: 372
<212> TYPE: DNA
<213> ORGANISM: Homo sapiens

<400> SEQUENCE: 67
caggtgcagc tggtgcagtc tggggggaggc ttggtccagc ctggggggtc cctgaaagtc    60
tcctgtgtag ctctggatt cacgttcagt gcctctacta tacactgggt ccgccaggcc    120
tccgggaaag gctggagtg ggttggccgt atcagaagca aagctaacaa ttacgcgaca    180
gtatctgctg cgtcgctgaa aggcaggttc accatctcca gagatgattc aaagaacacg    240
gcgtatctcc aagtgaacag cctgaaaatc gaggacacgg ccatttatta ctgtactaga    300
cctacggcct gcggtgaccg cgtctgctgg cacggggctt ggggccaggg aacccaggtc    360
accgtctccc ca                                                        372

<210> SEQ ID NO 68
<211> LENGTH: 324
<212> TYPE: DNA
<213> ORGANISM: Homo sapiens

<400> SEQUENCE: 68
gatatcatgc tgactcagcc accctcggtg tcagtgtccc caggacaaac ggccaggatc    60
acctgctctg gagatgcatt gccaaaaaaa tatacttatt ggtatcagca gaagtcaggc    120
caggcccctg ttttggtcat ctatgaggac agcaaacgac cctccgagat ccctgagaga    180
ttctctgcct tcacctcatg gacgacggcc accttgacta taactggggc ccaggtggga    240
gatgaagctg actactactg ttattcaaca gacatcactg gtgatatagg agtgttcggc    300
ggagggacca agctgaccgt cctg                                           324

<210> SEQ ID NO 69
<211> LENGTH: 372
<212> TYPE: DNA
<213> ORGANISM: Homo sapiens

<400> SEQUENCE: 69
caggtgcagc tggtggagtc tggggggaggc ttggcacagc ctggggggtc cctgagactc    60
tcctgtgcag cctctggatt catctttaac acctatgcca tgggctgggt ccgccaggct    120
ccagggaagg gctggagtg gtctcaact gttagtgctc tggtgctgg cacatactac    180 acagactccg tgaagggccg attcatcatc tccagagaca attccaagaa catactgtat    240
ctgcaaatga acaggctgag agtcgaggac acggccgtct attactgtgc gagggatcag    300 gggggggccag cagtggctgg tgcaaggatc tttgactact ggggccaggg agccctggtc    360
accgtctcct ca                                                        372

<210> SEQ ID NO 70
<211> LENGTH: 337
<212> TYPE: DNA
<213> ORGANISM: Homo sapiens
```

<400> SEQUENCE: 70

```
gatatcgtgt tgactcagtc tccactctct ctgtccgtca cccctggaca gccggcctcc    60
atctcctgca agtctagtca gagcctcctg cgtagtgatg gaaaaacata tttgtgctgg   120
tacctgcaga agccaggcca gcctccacag ctcctgatct atgaagtttc caaccgggtc   180
tctggagtgc cagacaggtt cagtggcagc gggtcaggga cagatttcac actgaaaatc   240
agccgggtgg aggctgagga tgttggggtt tattactgca tgcaaagtat acagcttcgg   300
acgttcggcc aagggaccaa ggtggaaatc aaacgaa                            337
```

<210> SEQ ID NO 71
<211> LENGTH: 19
<212> TYPE: PRT
<213> ORGANISM: Artificial Sequence
<220> FEATURE:
<223> OTHER INFORMATION: Synthetic

<400> SEQUENCE: 71

```
Ser Gly Ser Gly Ala Ala Arg Lys Gly Arg Asn Pro Gln Thr Gly Lys
1               5                   10                  15

Glu Ile Asp
```

<210> SEQ ID NO 72
<211> LENGTH: 19
<212> TYPE: PRT
<213> ORGANISM: Artificial Sequence
<220> FEATURE:
<223> OTHER INFORMATION: Synthetic

<400> SEQUENCE: 72

```
Ser Gly Ser Gly Lys Gly Arg Asn Pro Gln Thr Gly Lys Glu Ile Asp
1               5                   10                  15

Ile Pro Ala
```

<210> SEQ ID NO 73
<211> LENGTH: 19
<212> TYPE: PRT
<213> ORGANISM: Artificial Sequence
<220> FEATURE:
<223> OTHER INFORMATION: Synthetic

<400> SEQUENCE: 73

```
Ser Gly Ser Gly Arg Glu Arg Ala Ala Arg Lys Gly Arg Asn Pro Gln
1               5                   10                  15

Thr Gly Lys
```

<210> SEQ ID NO 74
<211> LENGTH: 13
<212> TYPE: PRT
<213> ORGANISM: Artificial Sequence
<220> FEATURE:
<223> OTHER INFORMATION: Synthetic

<400> SEQUENCE: 74

```
Lys Gly Arg Asn Pro Gln Thr Gly Lys Glu Ile Asp Ile
1               5                   10
```

<210> SEQ ID NO 75
<211> LENGTH: 19
<212> TYPE: PRT
<213> ORGANISM: Artificial Sequence
<220> FEATURE:
<223> OTHER INFORMATION: Synthetic

<400> SEQUENCE: 75

Ser Gly Ser Gly Val Pro Ala Phe Lys Ala Gly Lys Ala Leu Lys Asp
1               5                   10                  15

Ala Val Lys

<210> SEQ ID NO 76
<211> LENGTH: 19
<212> TYPE: PRT
<213> ORGANISM: Artificial Sequence
<220> FEATURE:
<223> OTHER INFORMATION: Synthetic

<400> SEQUENCE: 76

Ser Gly Ser Gly Ser Leu Ala Lys Gly Glu Lys Val Gln Leu Ile Gly
1               5                   10                  15

Phe Gly Asn

<210> SEQ ID NO 77
<211> LENGTH: 19
<212> TYPE: PRT
<213> ORGANISM: Artificial Sequence
<220> FEATURE:
<223> OTHER INFORMATION: Synthetic

<400> SEQUENCE: 77

Ser Gly Ser Gly Lys Gly Glu Lys Val Gln Leu Ile Gly Phe Gly Asn
1               5                   10                  15

Phe Glu Val

<210> SEQ ID NO 78
<211> LENGTH: 19
<212> TYPE: PRT
<213> ORGANISM: Artificial Sequence
<220> FEATURE:
<223> OTHER INFORMATION: Synthetic

<400> SEQUENCE: 78

Ser Gly Ser Gly Lys Val Gln Leu Ile Gly Phe Gly Asn Phe Glu Val
1               5                   10                  15

Arg Glu Arg

<210> SEQ ID NO 79
<211> LENGTH: 19
<212> TYPE: PRT
<213> ORGANISM: Artificial Sequence
<220> FEATURE:
<223> OTHER INFORMATION: Synthetic

<400> SEQUENCE: 79

Ser Gly Ser Gly Thr Lys Lys Glu Ala Gly Ser Ala Val Asp Ala Val
1               5                   10                  15

Phe Glu Ser

<210> SEQ ID NO 80
<211> LENGTH: 19
<212> TYPE: PRT
<213> ORGANISM: Artificial Sequence
<220> FEATURE:
<223> OTHER INFORMATION: Synthetic

<400> SEQUENCE: 80

Ala Ala Arg Lys Gly Arg Asn Pro Gln Thr Gly Glu Lys Glu Ile Asp
1               5                   10                  15

Ile Pro Ala

<210> SEQ ID NO 81
<211> LENGTH: 90
<212> TYPE: PRT
<213> ORGANISM: Staphylococcus aureus

<400> SEQUENCE: 81

Met Asn Lys Thr Asp Leu Ile Asn Ala Val Ala Glu Gln Ala Asp Leu
1               5                   10                  15

Thr Lys Lys Glu Ala Gly Ser Ala Val Asp Ala Val Phe Glu Ala Ile
                20                  25                  30

Gln Asn Ser Leu Ala Lys Gly Glu Lys Val Gln Leu Ile Gly Phe Gly
            35                  40                  45

Asn Phe Glu Val Arg Glu Arg Ala Ala Arg Lys Gly Arg Asn Pro Gln
        50                  55                  60

Thr Gly Lys Glu Ile Asp Ile Pro Ala Ser Lys Val Pro Ala Phe Lys
65                  70                  75                  80

Ala Gly Lys Ala Leu Lys Asp Ala Val Lys
                85                  90

<210> SEQ ID NO 82
<211> LENGTH: 91
<212> TYPE: PRT
<213> ORGANISM: Streptoccoccus pneumoniae

<400> SEQUENCE: 82

Met Ala Asn Lys Gln Asp Leu Ile Ala Lys Val Ala Glu Ala Thr Glu
1               5                   10                  15

Leu Thr Lys Lys Asp Ser Ala Ala Ala Val Glu Ala Val Phe Ala Ala
                20                  25                  30

Val Ala Asp Tyr Leu Ala Ala Gly Glu Lys Val Gln Leu Ile Gly Phe
            35                  40                  45

Gly Asn Phe Glu Val Arg Glu Arg Ala Glu Arg Lys Gly Arg Asn Pro
        50                  55                  60

Gln Thr Gly Lys Glu Ile Thr Ile Ala Ala Ser Lys Val Pro Ala Phe
65                  70                  75                  80

Lys Ala Gly Lys Ala Leu Lys Asp Ala Val Lys
                85                  90

<210> SEQ ID NO 83
<211> LENGTH: 108
<212> TYPE: PRT
<213> ORGANISM: Borrelia burgdorferi

<400> SEQUENCE: 83

Met Ser Phe Ser Arg Arg Pro Lys Val Thr Lys Ser Asp Ile Val Asp
1               5                   10                  15

Gln Ile Ala Leu Asn Ile Lys Asn Asn Leu Lys Leu Glu Lys Lys
                20                  25                  30

Tyr Ile Arg Leu Val Ile Asp Ala Phe Phe Glu Glu Leu Lys Ser Asn
            35                  40                  45

Leu Cys Ser Asn Asn Val Ile Glu Phe Arg Ser Phe Gly Thr Phe Glu
        50                  55                  60

Val Arg Lys Arg Lys Gly Arg Leu Asn Ala Arg Asn Pro Gln Thr Gly
65                  70                  75                  80

Glu Tyr Val Lys Val Leu Asp His His Val Ala Tyr Phe Arg Pro Gly
                85                  90                  95

Lys Asp Leu Lys Glu Arg Val Trp Gly Ile Lys Gly
            100                 105

<210> SEQ ID NO 84
<211> LENGTH: 98
<212> TYPE: PRT
<213> ORGANISM: Acinetobacter baumanii

<400> SEQUENCE: 84

Met Thr Ala Leu Thr Lys Ala Asp Met Ala Asp His Leu Ser Glu Leu
1               5                   10                  15

Thr Ser Leu Asn Arg Arg Glu Ala Lys Gln Met Val Glu Leu Phe Phe
                20                  25                  30

Asp Glu Ile Ser Gln Ala Leu Ile Ala Gly Glu Gln Val Lys Leu Ser
            35                  40                  45

Gly Phe Gly Asn Phe Glu Leu Arg Asp Lys Arg Glu Arg Pro Gly Arg
    50                  55                  60

Asn Pro Lys Thr Gly Glu Glu Ile Pro Ile Ser Ala Arg Arg Val Val
65                  70                  75                  80

Thr Phe Arg Ala Gly Gln Lys Phe Arg Gln Arg Val Gly Asn Glu Gln
                85                  90                  95

Ile Asp

<210> SEQ ID NO 85
<211> LENGTH: 105
<212> TYPE: PRT
<213> ORGANISM: Burkholderia pseudomallei

<400> SEQUENCE: 85

Met Thr Lys Ser Glu Leu Val Ala Gln Leu Ala Ser Arg Phe Pro Gln
1               5                   10                  15

Leu Val Leu Lys Asp Ala Asp Phe Ala Val Lys Thr Met Leu Asp Ala
                20                  25                  30

Met Ser Asp Ala Leu Ser Lys Gly His Arg Ile Glu Ile Arg Gly Phe
            35                  40                  45

Gly Ser Phe Gly Leu Asn Arg Arg Pro Ala Arg Val Gly Arg Asn Pro
    50                  55                  60

Lys Ser Gly Glu Lys Val Gln Val Pro Glu Lys His Val Pro His Phe
65                  70                  75                  80

Lys Pro Gly Lys Glu Leu Arg Glu Arg Val Asp Gly Arg Ala Gly Glu
                85                  90                  95

Pro Leu Lys Asn Asp Glu Pro Glu Asp
            100                 105

<210> SEQ ID NO 86
<211> LENGTH: 99
<212> TYPE: PRT
<213> ORGANISM: Enterobacter aerogenes

<400> SEQUENCE: 86

Met Ala Leu Thr Lys Ala Glu Met Ser Glu Tyr Leu Phe Asp Lys Leu
1               5                   10                  15

Gly Leu Ser Lys Arg Asp Ala Lys Glu Leu Val Glu Leu Phe Phe Glu
                20                  25                  30

```
Glu Ile Arg Arg Ala Leu Glu Asn Gly Glu Gln Val Lys Leu Ser Gly
            35                  40                  45

Phe Gly Asn Phe Asp Leu Arg Asp Lys Asn Gln Arg Pro Gly Arg Asn
        50                  55                  60

Pro Lys Thr Gly Glu Asp Ile Pro Ile Thr Ala Arg Arg Val Val Thr
65                  70                  75                  80

Phe Arg Pro Gly Gln Lys Leu Lys Ser Arg Val Glu Asn Ala Ser Pro
                85                  90                  95

Arg Glu Lys

<210> SEQ ID NO 87
<211> LENGTH: 99
<212> TYPE: PRT
<213> ORGANISM: Enterobacter cloacae

<400> SEQUENCE: 87

Met Ala Leu Thr Lys Ala Glu Met Ser Glu Tyr Leu Phe Asp Lys Leu
1               5                   10                  15

Gly Leu Ser Lys Arg Asp Ala Lys Glu Leu Val Glu Leu Phe Phe Glu
            20                  25                  30

Glu Ile Arg Arg Ala Leu Glu Asn Gly Glu Gln Val Lys Leu Ser Gly
            35                  40                  45

Phe Gly Asn Phe Asp Leu Arg Asp Lys Asn Gln Arg Pro Gly Arg Asn
        50                  55                  60

Pro Lys Thr Gly Glu Asp Ile Pro Ile Thr Ala Arg Arg Val Val Thr
65                  70                  75                  80

Phe Arg Pro Gly Gln Lys Leu Lys Ser Arg Val Glu Asn Ala Thr Pro
                85                  90                  95

Lys Ala Glu

<210> SEQ ID NO 88
<211> LENGTH: 99
<212> TYPE: PRT
<213> ORGANISM: Escherichia coli

<400> SEQUENCE: 88

Met Ala Leu Thr Lys Ala Glu Met Ser Glu Tyr Leu Phe Asp Lys Leu
1               5                   10                  15

Gly Leu Ser Lys Arg Asp Ala Lys Glu Leu Val Glu Leu Phe Phe Glu
            20                  25                  30

Glu Ile Arg Arg Ala Leu Glu Asn Gly Glu Gln Val Lys Leu Ser Gly
            35                  40                  45

Phe Gly Asn Phe Asp Leu Arg Asp Lys Asn Gln Arg Pro Gly Arg Asn
        50                  55                  60

Pro Lys Thr Gly Glu Asp Ile Pro Ile Thr Ala Arg Arg Val Val Thr
65                  70                  75                  80

Phe Arg Pro Gly Gln Lys Leu Lys Ser Arg Val Glu Asn Ala Ser Pro
                85                  90                  95

Lys Asp Glu

<210> SEQ ID NO 89
<211> LENGTH: 96
<212> TYPE: PRT
<213> ORGANISM: Haemophilus influenzae
```

<400> SEQUENCE: 89

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
            20                  25                  30

Glu Glu Ile Arg Leu Ser Leu Glu Ser Gly Gln Asp Val Lys Leu Ser
            35                  40                  45

Gly Phe Gly Asn Phe Glu Leu Arg Asp Lys Ser Ser Arg Pro Gly Arg
50                      55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 90
<211> LENGTH: 99
<212> TYPE: PRT
<213> ORGANISM: Klebsiella pheumoniae

<400> SEQUENCE: 90

Met Ala Leu Thr Lys Ala Glu Met Ser Glu Tyr Leu Phe Asp Lys Leu
1               5                   10                  15

Gly Leu Ser Lys Arg Asp Ala Lys Glu Leu Val Glu Leu Phe Phe Glu
            20                  25                  30

Glu Ile Arg Arg Ala Leu Glu Asn Gly Glu Gln Val Lys Leu Ser Gly
            35                  40                  45

Phe Gly Asn Phe Asp Leu Arg Asp Lys Asn Gln Arg Pro Gly Arg Asn
50                      55                  60

Pro Lys Thr Gly Glu Asp Ile Pro Ile Thr Ala Arg Arg Val Val Thr
65                  70                  75                  80

Phe Arg Pro Gly Gln Lys Leu Lys Ser Arg Val Glu Asn Ala Ser Leu
                85                  90                  95

Lys Asp Lys

<210> SEQ ID NO 91
<211> LENGTH: 100
<212> TYPE: PRT
<213> ORGANISM: Pseudomonas aeruginosa

<400> SEQUENCE: 91

Met Gly Ala Leu Thr Lys Ala Glu Ile Ala Glu Arg Leu Tyr Glu Glu
1               5                   10                  15

Leu Gly Leu Asn Lys Arg Glu Ala Lys Glu Leu Val Glu Leu Phe Phe
            20                  25                  30

Glu Glu Ile Arg Gln Ala Leu Glu Gln Asn Gly Gln Val Lys Leu Ser
            35                  40                  45

Gly Phe Gly Asn Phe Asp Leu Arg Asp Lys Arg Gln Arg Pro Gly Arg
50                      55                  60

Asn Pro Lys Thr Gly Glu Glu Ile Pro Ile Thr Ala Arg Arg Val Val
65                  70                  75                  80

Thr Phe Arg Pro Gly Gln Lys Leu Lys Ala Arg Val Glu Ala Tyr Ala
                85                  90                  95

Gly Thr Lys Ser
            100